(12) United States Patent
Mazin et al.

(10) Patent No.: US 9,216,177 B2
(45) Date of Patent: Dec. 22, 2015

(54) SMALL MOLECULAR INHIBITORS OF RAD51 RECOMBINASE AND METHODS THEREOF

(75) Inventors: Alexander V. Mazin, Philadelphia, PA (US); Fei Huang, Beijing (CN)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/001,806

(22) PCT Filed: Feb. 15, 2012

(86) PCT No.: PCT/US2012/025267
§ 371 (c)(1),
(2), (4) Date: Nov. 8, 2013

(65) Prior Publication Data
US 2014/0080849 A1    Mar. 20, 2014

Related U.S. Application Data

(60) Provisional application No. 61/447,410, filed on Feb. 28, 2011.

(51) Int. Cl.
| | |
|---|---|
| *A61K 31/506* | (2006.01) |
| *A61K 31/517* | (2006.01) |
| *A61K 45/06* | (2006.01) |
| *C07D 401/06* | (2006.01) |
| *A61K 31/365* | (2006.01) |
| *A61N 5/10* | (2006.01) |

(52) U.S. Cl.
CPC .............. *A61K 31/506* (2013.01); *A61K 31/365* (2013.01); *A61K 31/517* (2013.01); *A61K 45/06* (2013.01); *C07D 401/06* (2013.01); *A61N 2005/1098* (2013.01)

(58) Field of Classification Search
None
See application file for complete search history.

(56) References Cited

U.S. PATENT DOCUMENTS

| | | |
|---|---|---|
| 3,748,325 A | 7/1973 | Somasekhara et al. |
| 6,303,615 B1 | 10/2001 | Elliott et al. |
| 6,380,204 B1 | 4/2002 | Chenard et al. |
| 2003/0171387 A1 | 9/2003 | Sun et al. |
| 2007/0179164 A1 | 8/2007 | Chong et al. |

FOREIGN PATENT DOCUMENTS

| | | |
|---|---|---|
| JP | H07-069882 | 3/1995 |
| WO | 2009126310 A2 | 10/2009 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface).*
Jordan, V. C. (Nature Reviews: Drug Discovery, 2, 2003, 205-213).*
International Search Report and Written Opinion for International Application No. PCT/US2012/025267 dated May 31, 2012.
Burlando, B. et al., "Antiproliferative Effects on Tumor Cells and Promotion of Keratinocyte Wound Healing by Different Lichen Compounds," Planta Med, vol. 75, pp. 607-613, 2009.
Hirayama, T. et al., "Anti-Tumor Activities of Some Lichen Products and Their Degradation Products," Journal of the Pharmaceutical Society of Japan, vol. 100, No. 7, pp. 755-759, 1980.
Gohil, V.M. et al., "Nutrient-Sensitized Screening for Drugs that Shift Energy Metabolism from Mitochondrial Respiration to Glycolysis," Nature Biotechnology, vol. 28, No. 3, pp. 249-255, 2010.
Theoclitou, M-E. et al., "Solid Phase Synthesis of Styrylquinazolinones,"Tetrahedron Letters, vol. 41, pp. 2051-2054, 2000.

* cited by examiner

*Primary Examiner* — Jeffrey S Lundgren
*Assistant Examiner* — William Lee
(74) *Attorney, Agent, or Firm* — Saul Ewing LLP; Kathryn Doyle; Domingos J. Silva

(57) ABSTRACT

The invention includes compositions comprising a selective small-molecule inhibitor of RAD51 recombinase and a pharmaceutically acceptable carrier. The invention further includes methods of treating or preventing cancer in a subject, comprising the step of administering to the subject the compositions contemplated within the invention.

7 Claims, 37 Drawing Sheets

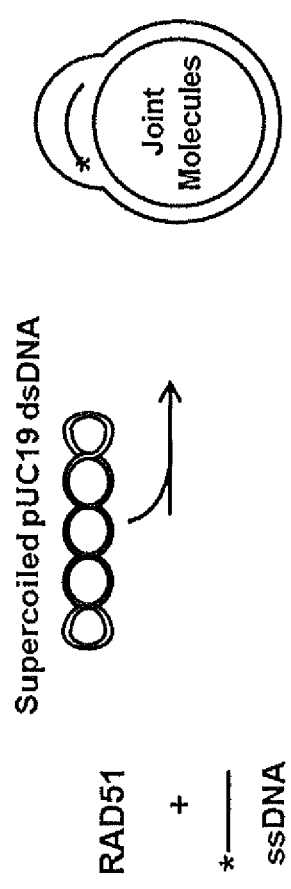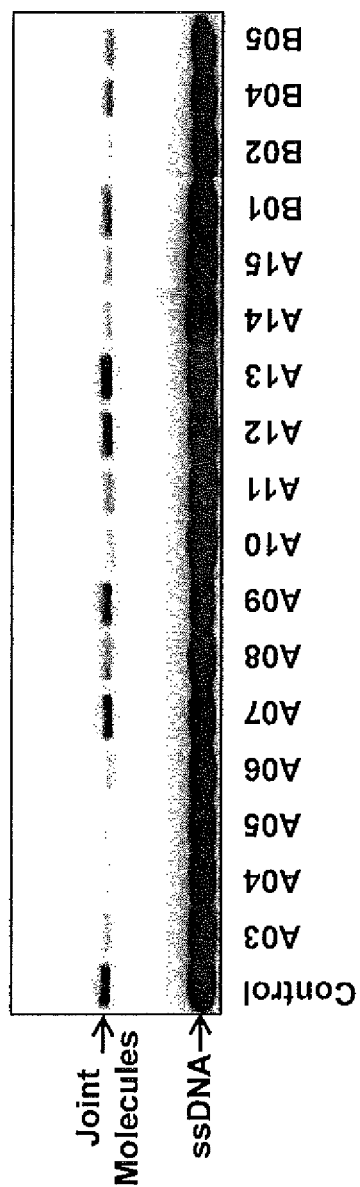
Fig. 3A
Fig. 3B

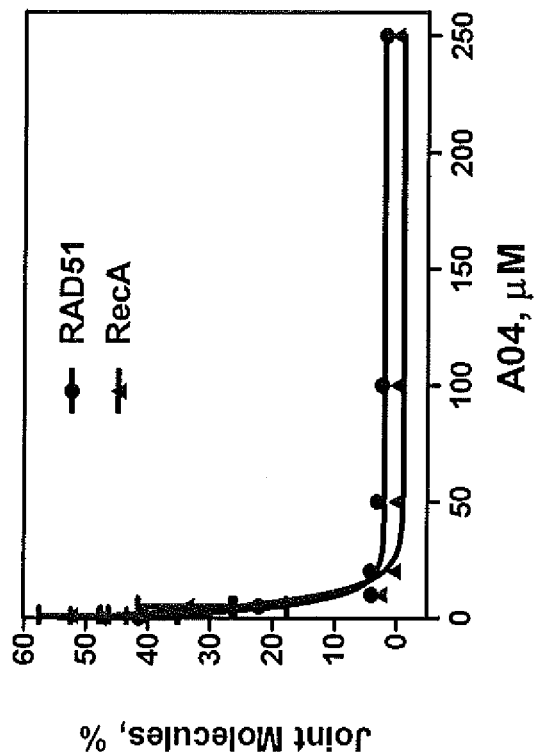
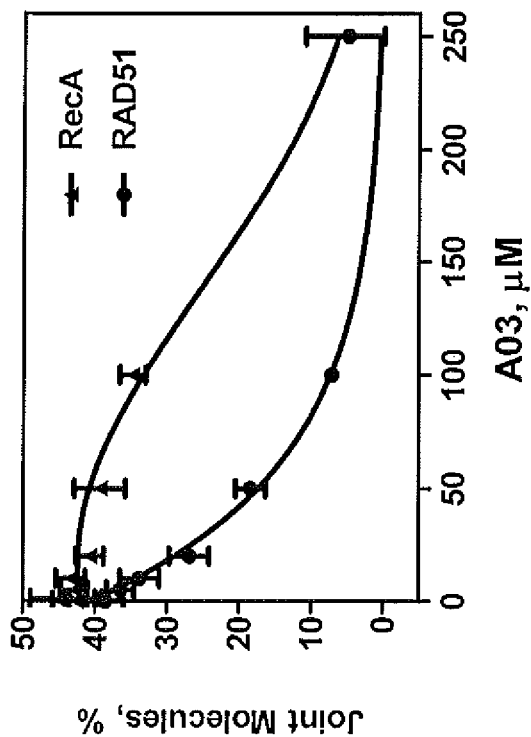

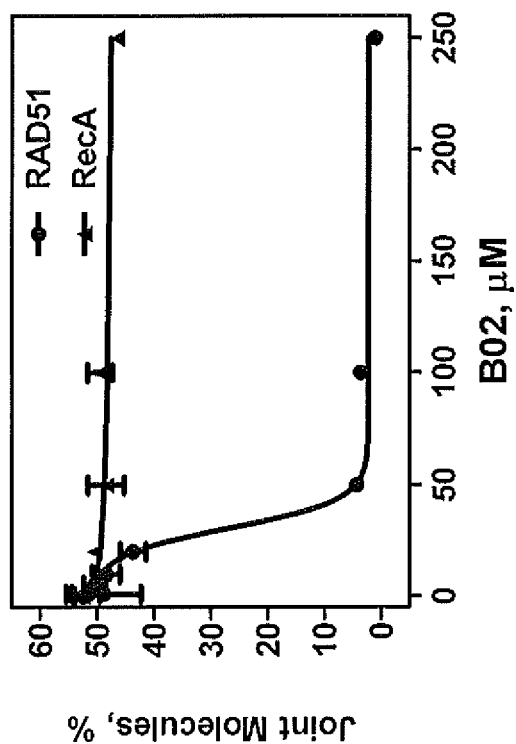
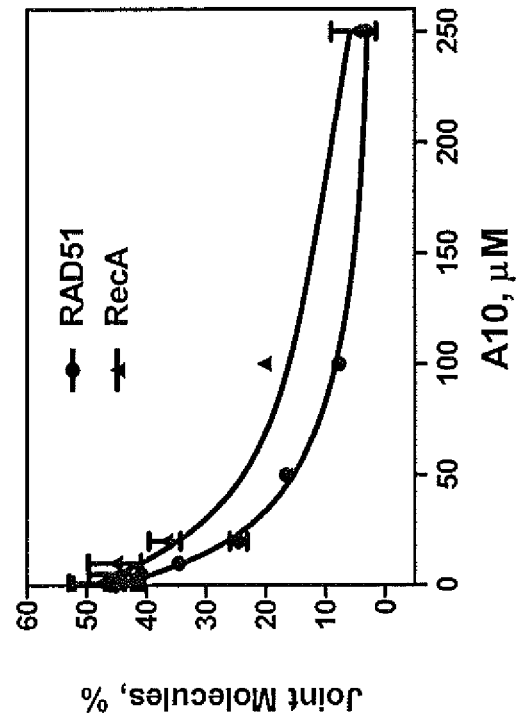

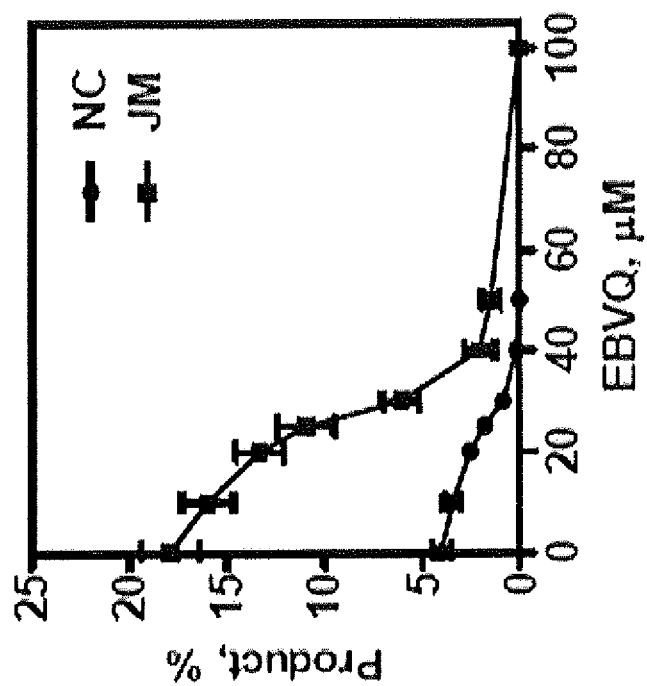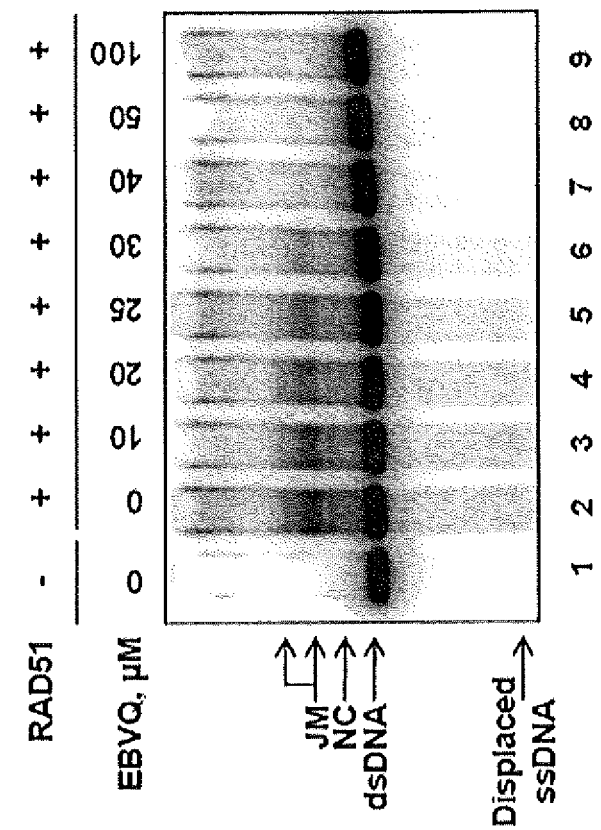
Fig. 10B
Fig. 10C

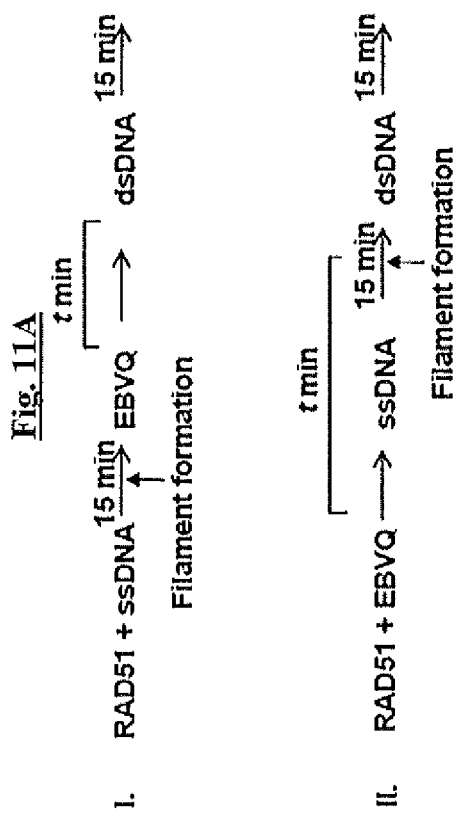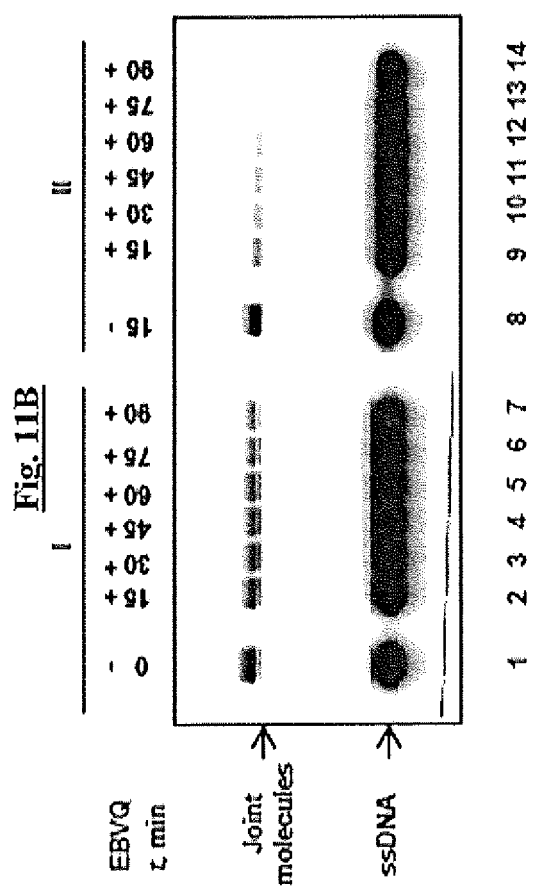

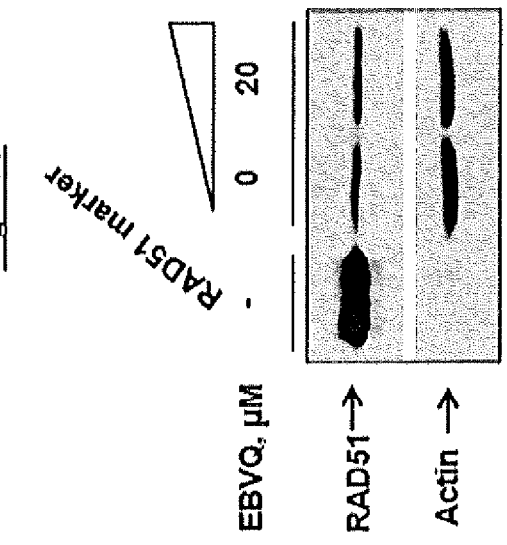
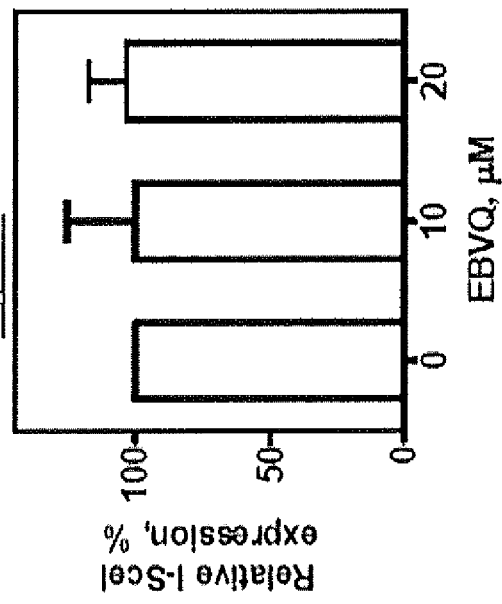
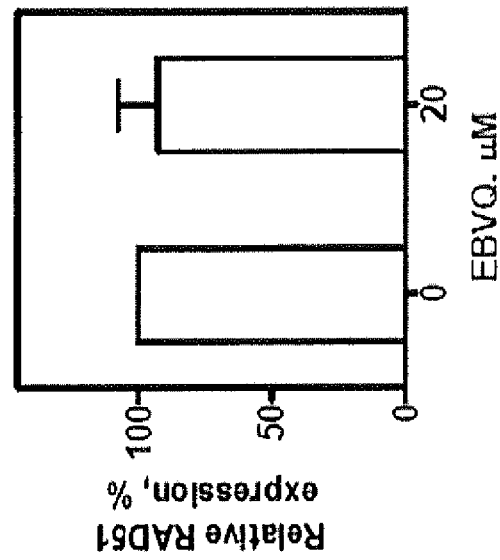
Fig. 16B
Fig. 16C
Fig. 16D

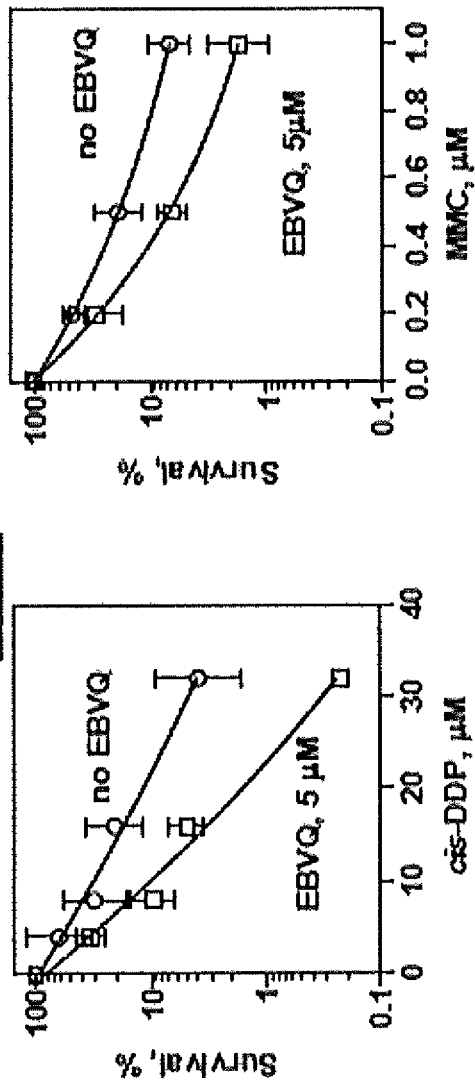
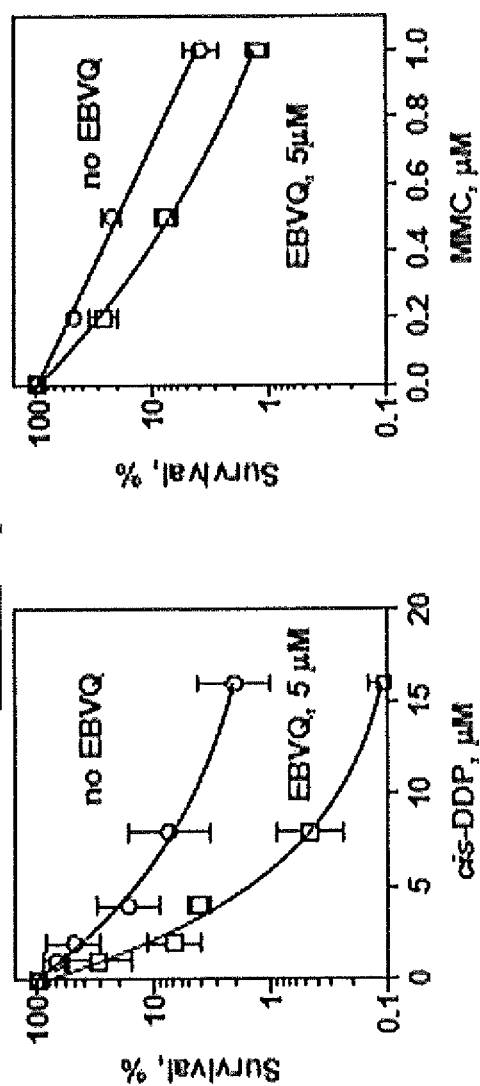
Fig. 17A: MEF
Fig. 17B: Tp53⁻/⁻ MEF

Joint molecule formation

Branch migration

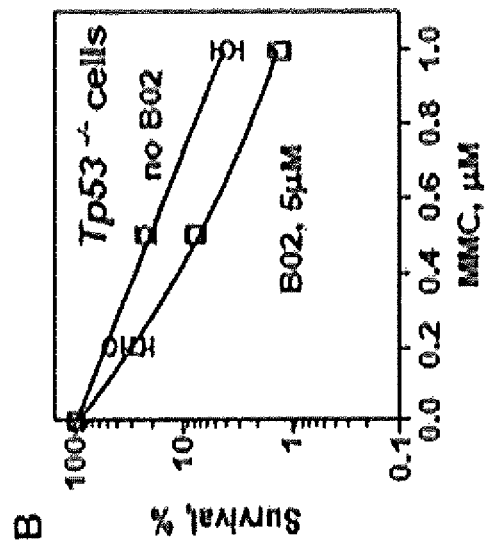
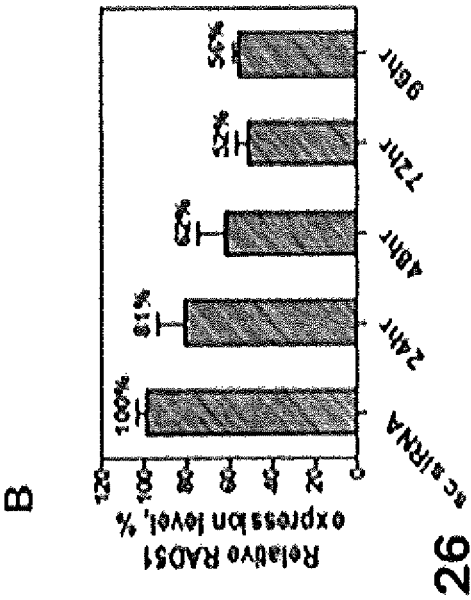
Fig. 25
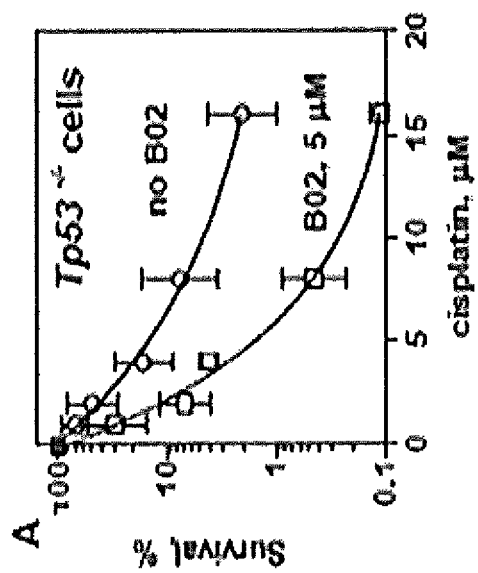
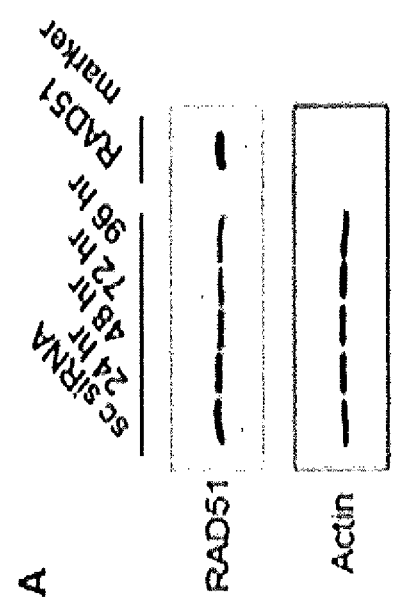
Fig. 26

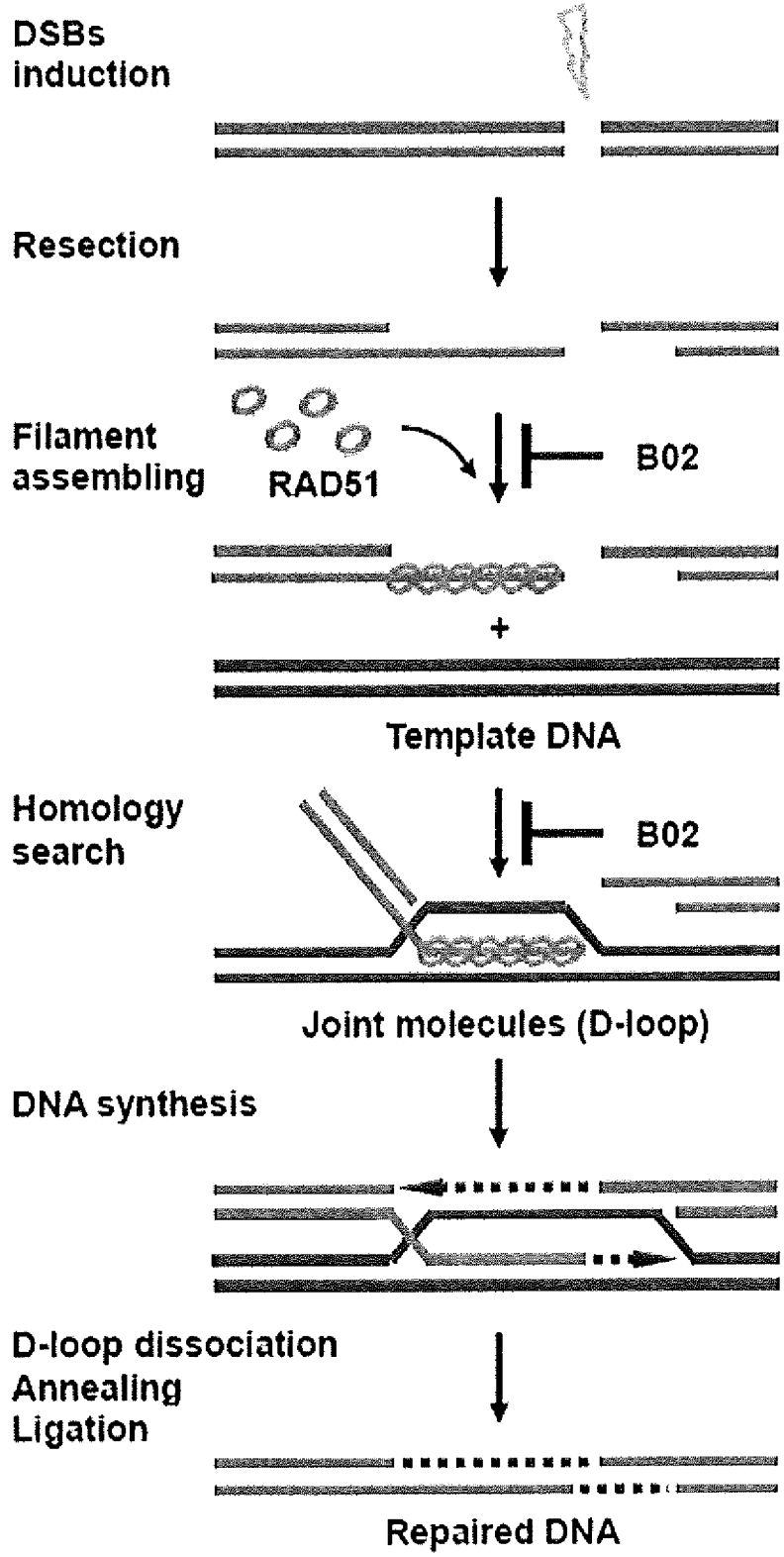

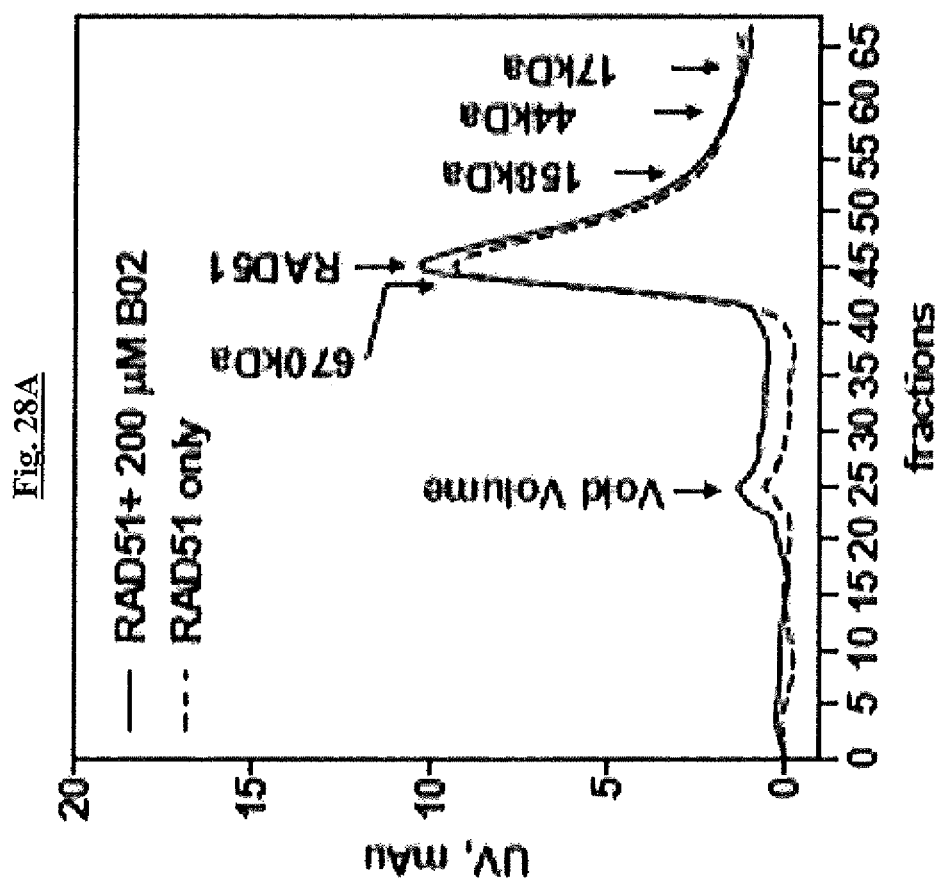

SEQUENCE LISTING

```
<160> NUMBER OF SEQ ID NOS: 10

<210> SEQ ID NO 1
<211> LENGTH: 339
<212> TYPE: PRT
<213> ORGANISM: Artificial Sequence
<220> FEATURE:
<223> OTHER INFORMATION: Chemically synthesized

<400> SEQUENCE: 1

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
```

```
                    85                  90                  95
Ser Glu Ile Ile Gln Ile Thr Thr Gly Ser Lys Glu Leu Asp Lys Leu
                100                 105                 110

Leu Gln Gly Gly Ile Glu Thr Gly Ser Ile Thr Glu Met Phe Gly Glu
            115                 120                 125

Phe Arg Thr Gly Lys Thr Gln Ile Cys His Thr Leu Ala Val Thr Cys
130                 135                 140

Gln Leu Pro Ile Asp Arg Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Tyr Gln Ala Ser
        195                 200                 205

Ala Met Met Val Glu Ser Arg Tyr Ala Leu Leu Ile Val Asp Ser Ala
210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
290                 295                 300

Gly Arg Gly Glu Thr Arg Ile Cys Lys Ile Tyr Asp Ser Pro Cys Leu
                305                 310                 315                 320

Pro Glu Ala Glu Ala Met Phe Ala Ile Asn Ala Asp Gly Val Gly Asp
            325                 330                 335

Ala Lys Asp

<210> SEQ ID NO 2
<211> LENGTH: 48
<212> TYPE: DNA
<213> ORGANISM: Artificial Sequence
<220> FEATURE:
<223> OTHER INFORMATION: Chemically synthesized

<400> SEQUENCE: 2
gcaattaagc tctaagccat ccgcaaaaat gacctcttat caaaagga          48

<210> SEQ ID NO 3
<211> LENGTH: 47
<212> TYPE: DNA
<213> ORGANISM: Artificial Sequence
<220> FEATURE:
<223> OTHER INFORMATION: Chemically synthesized

<400> SEQUENCE: 3
caattaagct ctaagccatc cgcaaaaatg acctcttatc aaaagga             47

<210> SEQ ID NO 4
<211> LENGTH: 47
<212> TYPE: DNA
<213> ORGANISM: Artificial Sequence
<220> FEATURE:
```

<223> OTHER INFORMATION: Chemically synthesized

<400> SEQUENCE: 4 tcctttgat aagaggtcat ttttgcggat ggcttagagc ttaattg            47

<210> SEQ ID NO 5
<211> LENGTH: 48
<212> TYPE: DNA
<213> ORGANISM: Artificial Sequence
<220> FEATURE:
<223> OTHER INFORMATION: Chemically synthesized

<400> SEQUENCE: 5
gttcagtcag tgctcgatat gcggtgtgaa ttacggctca gttgccta          48

<210> SEQ ID NO 6
<211> LENGTH: 90
<212> TYPE: DNA
<213> ORGANISM: Artificial Sequence
<220> FEATURE:
<223> OTHER INFORMATION: Chemically synthesized

<400> SEQUENCE: 6
cgggtgtcgg ggctggctta actatgcggc atcagagcag attgtactga gagtgcacca       60
tatgcggtgt gaaataccgc acagatgcgt                                        90

<210> SEQ ID NO 7
<211> LENGTH: 94
<212> TYPE: DNA
<213> ORGANISM: Artificial Sequence
<220> FEATURE:
<223> OTHER INFORMATION: Chemically synthesized

<400> SEQUENCE: 7
ctttagctgc atatttacaa catgttgacc tacagcacca gattcagcaa ttaagctcta       60
agccatccgc aaaaatgacc tcttatcaaa agga                                   94

<210> SEQ ID NO 8
<211> LENGTH: 93
<212> TYPE: DNA
<213> ORGANISM: Artificial Sequence
<220> FEATURE:
<223> OTHER INFORMATION: Chemically synthesized

<400> SEQUENCE: 8 tcctttgat aagaggtcat ttttgcggat ggcttagagc ttaattgctg aatctggtgc        60 tgttttttt tttttttttt ttttttttt ttt                                      93

<210> SEQ ID NO 9
<211> LENGTH: 94
<212> TYPE: DNA
<213> ORGANISM: Artificial Sequence
<220> FEATURE:
<223> OTHER INFORMATION: Chemically synthesized

<400> SEQUENCE: 9 tcctttgat aagaggtcat ttttgcggat ggcttagagc ttaattgcta aatctggtgc        60
tgtaggtcaa catgttgtaa atatgcagct aaag                                   94

<210> SEQ ID NO 10
<211> LENGTH: 63
<212> TYPE: DNA
<213> ORGANISM: Artificial Sequence

```
<220> FEATURE:
<223> OTHER INFORMATION: Chemically synthesized

<400> SEQUENCE: 10
acagcaccag atttagcaat taagctctaa gccatccgca aaaatgacct cttatcaaaa    60
gga                                                                  63
```

SMALL MOLECULAR INHIBITORS OF RAD51 RECOMBINASE AND METHODS THEREOF

CROSS-REFERENCE TO RELATED APPLICATIONS

The present application is a 35 U.S.C. §371 national phase application of, and claims priority to, International Application No. PCT/US12/25267, filed Feb. 15, 2012, and published under PCT Article 21(2) in English, which claims priority under 35 U.S.C. §119(e) to U.S. Provisional Application No. 61/447,410, filed on Feb. 28, 2011, all of which applications are hereby incorporated by reference in their entireties herein.

STATEMENT REGARDING FEDERALLY SPONSORED RESEARCH OR DEVELOPMENT

This invention was made with government support under grant numbers CA100839 and MH084119 awarded by the National Institutes of Health. The government has certain rights in the invention.

BACKGROUND OF THE INVENTION

As a high-fidelity recombination that is evolutionarily conserved from bacteria to mammals, homologous recombination plays an essential role in maintaining genome integrity. Homologous recombination plays a critical role in the repair of DNA double-strand breaks and interstrand crosslinks, the most harmful types of DNA lesions (Helleday et al., 2007, "DNA double-strand break repair: Prom mechanistic understanding to cancer treatment", DNA Repair (Amst); Krogh & Symington, 2004, Annu. Rev. Genet, 38:233-71; San Filippo et al., 2008, Ann. Rev. Biochem, 77:229-57). Mutations in homologous recombination genes may cause cancer and genetic abnormalities related syndromes, such as Down's, Werner's and Klinefelter's syndromes (Hoeijmakers, 2001, Nature 411:366-74; Helleday el al, 2007, DNA Repair 6:923-35).

RAD51 recombinase (human sequence, SEQ ID NO:1), an ortholog of *E. coli* RecA, is a key protein in homologous recombination in mammalian cells, RAD51 promotes the repair of double-strand breaks, the most harmful type of DNA lesion. Double-strand breaks are induced by various chemical agents and ionizing radiation, and are also formed during the repair of interstrand crosslinks, Once double-strand breaks are formed, (hey are processed first by exonucleases to generate extensive ssDNA tails (Cejka et al., 2010, Nature 467:112-16; Mimitou & Symington, 2009, "DNA end resection: many nucleases make light work", DNA Repair (Amst) 8:983-95), Then RAD51 protein binds these ssDNA tails forming helical nucleoprotein filaments that promote in search for homologous dsDNA sequences (Kowalczykowski, 2008, Nature 453:463-66), Once homologous dsDNA sequences are found, RAD51 promotes DNA strand exchange between the ssDNA that resides within the filament and homologous dsDNA, i.e., an invasion of ssDNA into homologous DNA duplex that results in the displacement of the identical ssDNA from the duplex and formation of a joint molecule. Joint molecules, key intermediates of DSB repair, provide both the template and the primer for DNA repair synthesis that is required for double-strand break repair (Paques & Haber, 1999, Microbiol. Mol. Biol. Rev. 63:349-404).

By promoting DNA strand exchange, RAD51 plays a key role in homologous recombination. The protein is evolutionarily conserved from bacteriophages to mammals. In all organisms RAD51 orthologs play an important role in DNA repair and homologous recombination (Krough & Symington, 2004, Annu. Rev. Genet. 38:233-71; Helleday et al., 2007, DNA Repair 6:923-35; Huang et al., 1996, Proc. Natl. Acad. Sci. USA 93:4827-32; Tsuzuki et al., 1996, Proc. Natl. Acad. Sci. USA 93, 6236-40). However, only in higher eukaryotes does Rad51 become essential for cell viability. The knockout of the murine RAD51 gene caused embryonic lethality of homozygoes (San Filippo et al., 2008, Ann. Rev. Biochem. 77:229-57). Murine embryonic fibroblasts became prematurely senescent in tissue culture and did not proliferate for more than a few generations. Rad51 inactivation is detrimental for proliferation of the chicken DT-40 cells, as well (Li et al., 2009, Biochemistry 48:6805-10).

RAD51 was found to be overexpressed in many tumors, including familial BRCAI-deficient breast tumors (Raderschall et al., 2002, Cancer Res 62:219-25; Xia et al., 1997, Mol. Cell. Biol. 17:7151-58; Maacke et al., 2000, Intl. J. Cancer 88:907-13). Overexpression of RAD51 is thought to rescue homologous recombination by compensating for the lack of functional BRCAI or other DNA repair proteins. Because RAD51 overexpression may contribute to chemoresistance and radioresistance of human cancers (Ito et al., 2005, J. Gene Med. 7:1044-52), this protein represents an important target for anti-cancer therapy. Identification and use of RAD51 inhibitors may lead to development of novel combination anticancer therapies. Since homologous recombination plays an important role in the repair of double-strand breaks and interstrand crosslinks, efficiency of traditional anticancer therapies, which widely use ionizing radiation and other double-strand-breaking and intrastrand-crosslinking agents, may be increased by inhibiting homologous recombination in cancer cells by virtue of inhibiting the action of RAD51. Furthermore, inhibitors that block specific activities of RAD51, like DNA strand exchange or ATP hydrolysis, may be useful in the investigation of the cellular functions of this protein. Recently, small molecules inhibitors were employed in several studies to investigate the activity of RAD51 in homologous recombination (Li et al., 2009, Biochemistry 48:6805-10; Ishida et al., 2009, Nucl. Acids Res. 37:3367-76). However, so far no specific inhibitors of RAD51 have been disclosed in the art.

There is a need in the art to identify novel small molecule inhibitors of human RAD51 recombinase. The present invention fulfills this need.

BRIEF SUMMARY OF THE INVENTION

The invention includes a pharmaceutical composition comprising a pharmaceutically acceptable carrier and a compound of Formula (1):

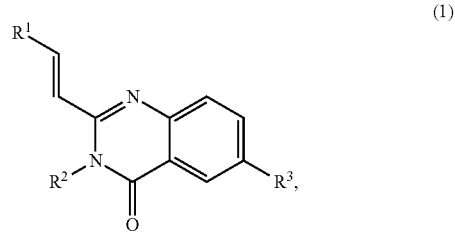

wherein $R^1$ and $R^2$ are independently selected from the group consisting of H, $C_1$-$C_6$ alkyl, $C_1$-$C_6$ substituted alkyl, phenyl, substituted phenyl, heteroaryl, substituted heteroaryl, heterocyclyl, substituted heterocyclyl, —($C_1$-$C_6$)alkylene-phenyl, —($C_1$-$C_6$) alkylene-substituted phenyl, —($C_1$-$C_6$)alkylene-heteroaryl, and —($C_1$-$C_6$)alkylene-substituted heteroaryl; $R^3$ is H, $C_1$-$C_6$ alkyl, O($C_1$-$C_6$ alkyl), F, Cl, Br or I; or a salt thereof.

In one embodiment, $R^1$ is phenyl, substituted phenyl, heteroaryl, or substituted heteroaryl. In another embodiment, $R^1$ is selected from the group consisting of phenyl, o-tolyl, m-tolyl, p-tolyl, o-methoxyphenyl, m-methoxyphenyl, p-methoxyphenyl, o-halophenyl, m-halophenyl, p-halophenyl, o-nitrophenyl, m-nitrophenyl, p-nitrophenyl, 2-pyridinyl, 3-pyridinyl, and 4-pyridinyl.

In one embodiment, $R^2$ is $C_1$-$C_6$ alkyl, phenyl, substituted phenyl, heteroaryl, substituted heteroaryl, —($C_1$-$C_6$)alkylene-phenyl, —($C_1$-$C_6$)alkylene-substituted phenyl, —($C_1$-$C_6$)alkylene-heteroaryl, or —($C_1$-$C_6$)alkylene-substituted heteroaryl. In another embodiment, $R^2$ is $C_1$-$C_6$ alkyl, phenyl, substituted phenyl, heteroaryl, substituted heteroaryl, —($C_1$-$C_6$)alkylene-phenyl, or —($C_1$-$C_6$)alkylene-substituted phenyl. In yet another embodiment, $R^2$ is methyl, ethyl, n-propyl, isopropyl, phenyl, o-tolyl, m-tolyl, p-tolyl, benzyl or substituted benzyl.

In one embodiment, $R^3$ is H, $C_1$-$C_6$ alkyl, —O($C_1$-$C_6$ alkyl), F or Cl. In another embodiment, $R^3$ is H, methyl, ethyl, methoxy or ethoxy. In yet another embodiment, $R^3$ is H.

In one embodiment, the compound is selected from the group consisting of:

(E)-3-benzyl-2-(2-(pyridin-3-yl)vinyl)quinazolin-4(3H)-one (1a)

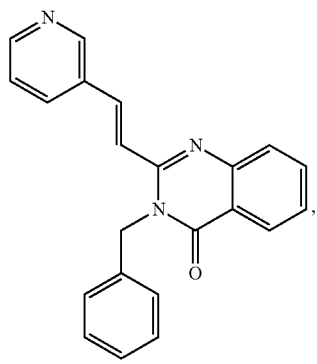

(E)-3-ethyl-2-(2-(pyridin-3-yl)vinyl)quinazolin-4(3H)-one (1b)

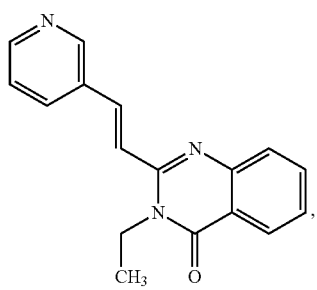

(E)-2-(2-(pyridin-3-yl)vinyl)-3-(m-tolyl)quinazolin-4(3H)-one (1c)

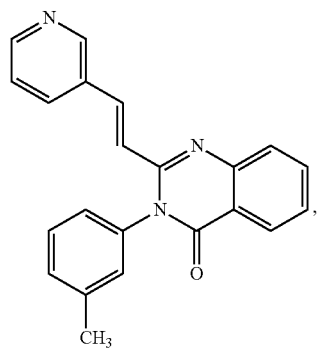

mixtures thereof and salts thereof.

In one embodiment, the composition further comprises a chemotherpeutic agent. In another embodiment, the agent is selected from the group consisting of an alkylating agent, antimetabolite, anthracycline, plant alkaloid, plant terpenoid, topoisomerase inhibitor, antineoplastic agent, and combinations thereof.

The invention also includes a method of treating or preventing cancer in a subject in need thereof. The method comprises administering to the subject a pharmaceutical composition comprising a pharmaceutically acceptable carrier and a pharmaceutically effective amount of a compound selecting from the group consisting of Formula (1), Formula (2), Formula (3), a salt thereof, and combinations thereof:

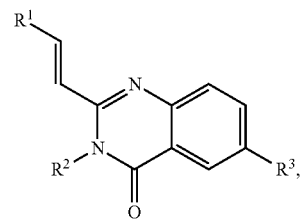

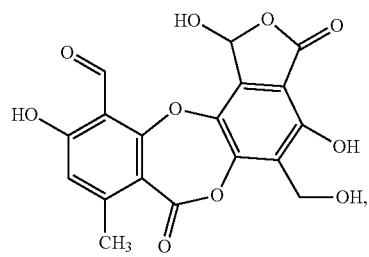

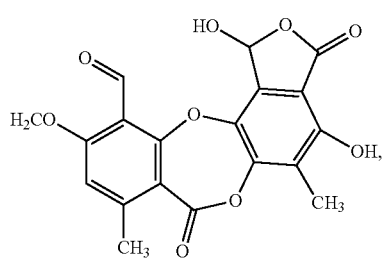

wherein in (1): $R^1$ and $R^2$ are independently selected from the group consisting of H, $C_1$-$C_6$ alkyl, $C_1$-$C_6$ substituted alkyl, phenyl, substituted phenyl, heteroaryl, substituted heteroaryl, heterocyclyl, substituted heterocyclyl, —($C_1$-$C_6$)alkylene-phenyl, —(C$_1$-C$_6$)alkylene-substituted phenyl, —(C$_1$-C$_6$) alkylene-heteroaryl, and —(C$_1$-C$_6$)alkylene-substituted heteroaryl; R$^3$ is H, C$_1$-C$_6$ alkyl, O(C$_1$-C$_6$ alkyl), F, Cl, Br or I; or a salt therof. The method further comprises administering to the subject a treatment selected from the group consisting (i) radiation therapy, and (ii) a pharmaceutical composition comprising a pharmaceutically effective amount of a chemotherapeutic agent; whereby treating or preventing the cancer in the subject.

In one embodiment, the compound is selected from the group consisting of (E)-3-benzyl-2-(2-(pyridin-3-yl)vinyl) quinazolin-4(3H)-one (1a), (E)-3-ethyl-2-(2-(pyridin-3-yl) vinyl)quinazolin-4(3H)-one (1b), (E)-2-(2-(pyridin-3-yl)vinyl)-3-(m-tolyl)quinazolin-4(3H)-one (1c), 1,4,10-trihydroxy-5-(hydroxymethyl)-8-methyl-3,7-dioxo-3,7-dihydro-1H-benzo[6,7][1,4]dioxepino[2,3-e]isobenzofuran-11-carbaldehyde (2), 1,4-dihydroxy-10-methoxy-5,8-dimethyl-3,7-dioxo-3,7-dihydro-1H-benzo[6,7][1,4] dioxepino[2,3-e]isobenzofuran-11-carbaldehyde (3), a salt thereof, and mixtures thereof.

In one embodiment, the administering to the subject of the compound is performed at least 24 hours prior to the administering to the subject the radiation therapy or the chemotherapeutic agent. In another embodiment, the administering to the subject of the compound is performed at least 12 hours prior to the administering to the subject the radiation therapy or the chemotherapeutic agent. In yet another embodiment, the administering to the subject the radiation therapy or the chemotherapeutic agent. In yet another embodiment, the administering to the subject of the compound is performed at least 3 hours prior to the administering to the subject the radiation therapy or the chemotherapeutic agent. In yet another embodiment, the administering to the subject of the compound is performed at least 1 hour prior to administering to the subject the radiation therapy or the chemotherapeutic agent.

In one embodiment, the composition comprising the compound is co-administered to the subject with the radiation therapy or the composition comprising the chemotherapeutic agent. In another embodiment, the compound and the chemotherapeutic agent are co-formulated in a pharmaceutical composition. In yet another embodiment, the subject is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A illustrates the reaction scheme. The terms "FLU" and "BHQ1" denote fluorescein and black hole quencher 1, respectively. Broken-line and solid-line arrows denote fluorescein emission at 521 nm before and after DNA strand exchange, respectively. The excitation wavelength was 490 nm. FIG. 1B is a graph that illustrates the kinetics of DNA strand exchange promoted by RAD51. The fluorescence intensity was expressed in arbitrary units (AU). "Homologous DNA" and "Heterologous DNA" denote reactions with homologous (SEQ ID NO: 2, 48-mer) and heterologous ssDNA (SEQ ID NO:5, 48-mer), respectively.

FIG. 2, comprising

FIG. 3, comprising FIGS. 3A-3E, illustrates the secondary screening of the RAD51 inhibitors using the D-loop assay. FIG. 3A is a scheme illustrating the D-loop formation promoted by RAD51. The asterisk denotes the $^{32}$P label. FIG. 3B is a reproduction of an electrophoresis gel that illustrates the analysis of 17 compounds selected by HTS. RAD51 (1 μM) was incubated with a 90-mer ssDNA (3 μM) (SEQ ID NO:6) to form the filament followed by addition of indicated compounds (100 μM). Joint molecule (D-loop) formation was initiated by addition of pUC19 supercoiled dsDNA (50 μM). The DNA products were analyzed by electrophoresis in a 1% agatose gel. The control was carried out under identical conditions except that no tested compounds on the yield of joint molecules. The extent of D-loop formation in the absence of inhibitors, 40.3%, was expressed as 100% of D-loop formation efficiency. Experiments were repeated at least three times: error bars represent standard deviation (standard deviation). FIG. 3D comprises reproductions of electrophoresis gels that illustrate the effect of Compound B02 concentration on the DNA strand exchange activity of RAD51 and RecA. After incubation of RAD51 (0.3 μM) or RecA (0.3 μM) with Compound B02 in indicated concentrations for 30 min, 0.9 μM ssDNA (SEQ ID NO:6, 90 mer) was added to form RAD51 nucleoprotein filament for 15 min. The D-loop formation was initiated by addition supercoiled pUC19 dsDNA (15 μM). The control reactions containing no proteins are shown in lane 1 and 10. In FIG. 3E, the yield of joint molecules (D-loops) was plotted as a graph. The extents of D-loop formation in the absence of Compound B02, 32% and 33.7% for RAD51 and RecA, respectively, were expressed as 100% of D-loop formation efficiency. Experiments were repeated at least three times; error bars represent S.E.M. (standard error of the mean).

FIG. 5, comprising FIGS. 5A-5D, is a series of graphs illustrating the specificity of RAD51 inhibition by Compounds A03, A04, A10, and Bo2. RAD51 (1 μM) or RecA (1 μM) was incubated with a 90-mer ssDNA (3 μM) (SEQ ID NO:6) for 15 min (for RAD51) or 5 min (for RecA) to form the nucleoprotein filament. Then, tested compounds in indicated concentrations were added and incubation continued for 30 min. The D-loop formation was initiated by addition of pUC19 supercoiled dsDNA (50 μM) and continued for 15 min (for RAD51) or 3 min (for RecA). The DNA products were analyzed by electrophoresis in a 1% agarose gel. The yield of joint molecules (D-loops) was plotted as a graph. Experiments were repeated at least three times; error bars represent standard deviation.

FIG. 6, comprising FIG. 6A is a scheme that illustrates a scheme of branch migration promoted by RAD54. The asterisk denotes the $^{32}$P label. FIGS. 6B and 6C: branch migration was initiated by adding RAD54 (100 nM) to the mixtures containing PX-junctions (33 nM, molecules) and the small molecule inhibitors (in indicated concentrations). DNA products were analyzed by electrophoresis in 8% polyacrylamide gels. For each inhibitor concentration, the extent of branch migration was determined after 5 min of reaction (linear phase). The results are presented as graphs in FIGS. 6B and 6C. Experiments were repeated at least three times; error bars represent standard deviation.

FIG. 7, comprising FIG. 7A illustrates the structures of Compound B02 and its derivatives. FIG. 7B is a reproduction of an electrophoresis gel that illustrates the effect of indicated B02 derivatives on D-loop formation by RAD51, RAD51 (1 µM) was incubated with a 90-mer ssDNA (3 µM) (SEQ ID NO:6) for 15 min followed by addition of indicated compounds (50 µM). After a 30-min incubation, the D-loop formation was initiated by addition of 50 µM supercoiled pUC19 dsDNA. The DNA products were analyzed by electrophoresis in a 1% agarose gel. The control reaction was performed under the identical conditions, except that no tested compounds were added. FIG. 7C is a graph that illustrates the yield of joint molecules (D-loops). Experiments were repeated at least three times; error bars represent standard deviation.

FIG. 8, comprising FIG. 8A is a reproduction of an electrophoresis gel illustrating the effect of C3a on the DNA strand exchange activity of RAD51 and RecA. The nucleoprotein filaments were formed by incubating RAD51 (1 µM) or RecA (1 µM) with ssDNA (3 µM), then C3a was added in indicated concentrations and incubation continued for 30 min. D-loop formation was initiated by adding pUC19 supercoiled dsDNA (50 µM). The DNA products were analyzed by electrophoresis in a 1% agarose gel. The data from FIG. 8A was plotted as a graph in FIG. 8B. The yield of D-loop formation in the absence of C3a was expressed as 100%; the actual yield was 45.1% and 34.2%, for RecA and RAD51, respectively. FIG. 8C illustrates the effect of C3b on the DNA strand exchange activity of RAD51 and RecA. The reactions were carried out as in FIG. 8A; the data are plotted as a graph. The yield of D-loop formation in the absence of C3b was expressed as 100%; the actual yield was 48.1% and 31.6%, for RecA and RAD51, respectively. Experiments were repeated at least three times; error bars represent standard deviation.

FIG. 10, comprising FIGS. 10A-10C, illustrates the inhibition by Compound B02 of the three strand exchange promoted by RAD51 protein. FIG. 10A is a schematic representation of DNA strand exchange between φX174 circular ssDNA and linear φX174 dsDNA (linearized by ApaL1 restriction endonuclease). FIG. 10B is a reproduction of an electrophoresis gel illustrating the effect of the Compound B02 concentration on the efficiency of three strand exchange assay promoted by RAD51, RAD51 was incubated with indicated concentration of Compound B02 (lane 2-9) for 30 min; then φX174 circular ssDNA and RPA were added in turn, each addition was followed by a 5-min incubation; the strand exchange was initiated by addition of linear φX174 dsDNA. The DNA products were analyzed by electrophoresis in a 1% agarose gel. FIG. 10C is a graph illustrating data from FIG. 10B. Experiments were repeated at least three times; error bars represent standard error of the mean.

FIG. 11, comprising FIGS. 11A-11C, illustrates the finding that the order of Compound B02 addition affects the efficiency of D-loop formation promoted by RAD51, FIG. 11A is a reproduction of an electrophoresis gel illustrating the effect of the order of addition of Compound B02. The numbers above the arrows indicate time of incubation. (I) Compound B02 (20 µM) was added after the RAD51-ssDNA filament formation; (II) Compound B02 (20 µM) was added RAD51 before addition of ssDNA. FIG. 11B is a graph illustrating the analysis of joint molecules by electrophoresis in a 1% agarose gel. FIG. 11C is a graph in which the relative inhibition of joint molecule formation by Compound B02 is expressed as the ration of the joint molecules formed by RAD51 after Compound B02 treatment to those formed by RAD51 without Compound B02 treatment. "l" denotes the time period between the addition of Compound B02 and dsDNA. Experiments were repeated at least three times; error bars represent standard error of the mean.

FIG. 12, comprising FIG. 12A is a reproduction of an electrophoresis gel in which RAD51 (1 µM) was incubated with $^{32}$P-labeled ssDNA (SEQ ID NO:6, 90 mer) (2.5 µM, nt) in buffer containing indicated NaCl concentration either in the absence (lanes 2-7) or presence (lanes 8-13) of Compound B02 (25 µM). RAD51-ssDNA complexes were analyzed by electrophoresis in a 10% polyacrylamide gel. The results in FIG. 12A were shown as a graph in FIG. 12B. Lane 1 show migration of free ssDNA. Experiments were repeated at least three times; error bars represent standard error of the mean.

FIG. 14, comprising FIG. 14A is a scheme illustrating dsDNA coaggregation. FIG. 14B is a graph illustrating inhibition of the coaggregation of dsDNA and RAD51-ssDNA filament by Compound B02. To form the RAD51-ssDNA filaments, RAD51 (1 µM) and ssDNA (SEQ ID NO:7, 94 mer) (3 µM, nt) were incubated for 15 min. After filament formation, NaCl was added in indicated concentrations and coaggregation was initiated immediately by addition of $^{32}$P-labeled linear pUC19 dsDNA (linearized by BamHI restriction endonuclease) (25 µM, nt). Experiments were represented at least three times; error bars represent standard error of the mean.

FIG. 15, comprising FIG. 15A is a scheme illustrating the process of measuring the frequency of homologous recombination in human cells using the DRGFP reporter system. FIG. 15B is a set of panels (panels 1-6) illustrating the effect of Compound B02 on the repair of I-SceI-induced DSBs in 293 HEK cells carrying the chromosomally located DR-GFP reporter, as determined using flow cytometry. Green fluorescence (GRN-Hlog, indicated as "G" in the figure) was plotted against red fluorescence (RED-Hlog, indicated as "R" in the figure) for the sample of 10,000 cells. The GTP-positive population is denoted by the elliptical MI marker. Cells with I-SceI-induced DSBs were either untreated (panel 2) or treated with Compound B02 5 µM (panel 3), 10 µM (panel 4), or 20 µM (panel 5). As a negative control, parental uninduced and untreated cells are shown in panel 1. As a positive control, parental cells that were transfected with pMX-GFP plasmid encoding GFP protein are shown in panel 6. FIG. 15C is a graph illustrating the correlation of GFP positive cells as a function of Compound B02 concentration. To determine the effect of Compound B02 on the efficiency of formation of GFP-positive cells (transfection plus GFP expression) 293 HEK cells were treated with Compound B02 in 5 µM, 10 µM, and 20 µM concentration and then transfected with pMX-GFP-plasmid. Data are shown as a graph (denoted as "pMX-GFP", efficiency of formation of GFP-positive cells in the cells without Compound B02 treatment was expressed as 100% formations efficiency) along with the data from FIG. 15B (panels 2-5) that demonstrate the effect of Compound B02 on the formation GFPpositive cells resulted from DSB-induced homologous recombination (denoted "I-SecI", formation of GFP-positive cells in no Compound B02 treatment cells was expressed as 100%). Experiments were repeated at least three times; error bars represent standard deviation.

FIG. 16, comprising FIGS. 16A-16D, illustrates that finding that treatment with Compound B02 does not affect the expression levels of I-SceI and RAD51 in human cells. As illustrated in FIG. 16A, 293 HEK cells carrying the DR-GFP reporter were treated with Compound B02 in indicated concentrations or left untreated for 1 hr; and then pCbASec plasmid expressing I-SecI was transfected into the cells by GenDrill™ transfection reagent. After incubation, during which Compound B02 was present, until cell confluence (~64 h) cells were lysed and the expression level of I-SceI restriction endonuclease containing the HA antigen was determined by western blotting using HA-Tag antibodies. Actin that was probed with specific antibodies was used as a quantity standard. The data from FIG. 16A is illustrated as a graph in FIG. 16B. As illustrated in FIG. 16C, log-phase 293 HEK cells carrying the DR-GFP were incubated either in the absence or presence of Compound B02 (20 µM) until cells reached confluence (~24 h), the level of RAD51 expression was analyzed by western blotting using specific antibodies against RAD51 . Purified RAD51 protein (56 ng) was used as a standard. The data from FIG. 16C is illustrated as a graph in FIG. 16D. Experiments were repeated at least three times; error bars represent standard deviation.

FIG. 17, comprising FIGS. 17A-17C, illustrates the finding that Compound B02 increases the sensitivity of MEF cells to DNA damaging agents. MEF (FIG. 17A) or Tp53-/- MEF (FIG. 17B) cells were treated with myomycin C (MMC) or cis-dichlorodiamine platinum (II) (cisDDP) for 1 h in the absence or presence of Compound B02 (5 µM). In FIG. 17C, MEF and Tp53 -/- MEF cells were treated with Compound B02 in indicated concentrations. Experiments were repeated at least three times; error bars represent standard deviation.

FIGS. 19A-19F, illustrates the finding that Compound B02 interacts with RAD51 and inhibits its activities. FIG. 19A depicts the structure of Compound B02. FIG. 19B depicts the scheme of the DNA strand exchange and branch migration assays. The asterisk denotes the $^{32}$P label. FIG. 18C depicts the effect of Compound B02 (10 to 100 µM) on the DNA strand exchange activity of RAD51, FIG. 19D is a graph illustrating the yield of RAD51- and RecA-generated joint molecules (JM). FIG. 19E depicts the effect of Compound B02 (10 to 100 µM) on the branch migration activity of RAD51. Lanes 1 and 11 represent JMs before and after 8 h-incubation in the absence RAD51, respectively. FIG. 19F is a graph illustrating the yield of the RAD51- and RecA-generated nicked circle (NC) product. The extent of JM and NC formation in the absence of Compound B02 was expressed as 100%; the actual extent was 32% and 15% of JM (relative to linear dsDNA) and 21% and 63% of nicked circles for RAD51 and RecA (relative to JM-substrate), respectively. Controls containing no RAD51 are shown in lane 1. Experiments were repeated at least three times; error bars represent standard deviation (S.D.).

FIG. 20, comprising FIG. 20A illustrates the scheme of the DNA strand exchange and branch migration assays. The asterisk denotes the $^{32}$P label. FIG. 20B illustrates the effect of Compound B02 on the DNA strand exchange activity of RecA. FIG. 20C illustrates the effect of Compound B02 on the DNA branch migration activity of Rec A. Initial DNA substrates are shown in lane 1. Experiments were repeated at least three times; representative gels are shown.

FIGS. 22A-22D, illustrates the measurement of Compound B02 binding to RAD51 using SPR. The SPR analysis was performed on a GLH high-capacity sensor chip (Blu-Rad, Hercules, Calif.) with a high density of immobilized RAD51 (14,000 RU) (FIG. 22A and 22B) or RecA (9,000 RU) (FIGS. 22C and 22D). Compound B02 at concentrations of 6.25, 12.5, 25, and 50 µM in buffer S without ATP (FIGS. 22A and 22C) or with ATP (100 µM) (FIGS. 22B and 22D) was injected to the chip. A chip with the immobilized HIV-INL4-3 capsid protein served as a reference. Colored lines indicate experimental data, whereas black lines indicate fitting to the simple 1:1 binding model using the ProteOn Manager Software version 3.0 (Bio-Rad). When Compound B02 was injected over RAD51 in buffer S containing ATP (100 µM), the data did not fit to the simple binding model, probably due to a heterogeneity in the nucleotide binding states of the immobilized RAD51. For Compound B02 binding to RAD51 in the absence of ATP, kinetic values are as follows: ka=4.5(±0.3)×10$^3$M$^-$1s$^{-1}$; kd= 2.5(±0.3)×10$^{-2}$s$^-$1; Kd=5.6 µM. Experiments were repeated at least three times; numbers in parentheses represent S.D.

FIG. 23, comprising FIG. 23A illustrates HEK cells which were exposed to 0.5 Gy of IR in either the presence (50 µM)or absence of B02. RAD51 foci were visualized by immunostaining using RAD51 antibodies. Nuclei were counterstained with DAPI. Bars indicate 20 µm. FIG. 23B illustrates the fraction of foci-positive cells (the cells with ≥1 focus), which was determined by counting at least 150 cells in each experiment. FIG. 23C illustrates the determination of the mean of foci number per nucleus in focipositive cells by counting at least 50 cells in each experiment. Experiments were repeated three times; error bars represent S.D.

FIG. 24, comprising FIGS. 24A and 24B illustrate the survival of MEF treated with cisplatin or MMC for 1 h in the absence or presence of B02 (5 µM). FIG. 24C illustrates the effect of B02 on survival of MEF and Tp53−/− MEF, FIG. 24D illustrates the effect of B02 (0 to 10 µM) and RAD51 siRNA on HEK cells' sensitivity to cisplatin. HEK cells were transfected with RAD51 siRNA and incubated 40 h before treatment with cisplatin at indicated concentrations and B02 (5 µM). FIG. 24E illustrates the effect of B02 incubation time with HEK on cell sensitivity to cisplatin. HEK cells were treated with B02 (5 µM) for 1 h followed by addition of cisplatin (16 µM) and incubation for 1 h. Then cisplatin was removed and cells were incubated with B02 (5 µM) for the indicated times followed by media replacement and additional incubation for 7-10 days. FIG. 24F illustrates the effect of AZD2281 (0.01 µM) and B02 (5 µM) on MEF sensitivity to MMS. Experiments were repeated at least three times; error bars represent S.D.

FIG. 25, comprising FIGS. 25A-25B, illustrates the finding that Compound B02 increases the sensitivity of Tp53$^{-/-}$ MEF to cisplatin and MMC. Tp53$^{-/-}$ MEF were treated with cisplatin (FIG. 25A) or MMC (FIG. 25B) for 1 h in the absence or presence of B02 (5 µM). Experiments were repeated at least three times; error bars represent S.D.

FIG. 26, comprising FIGS. 26A-26B, illustrates the effect of RAD51 siRNA on the expression level of RAD51. FIG. 26A illustrates the RAD51 expression levels 24, 48, 72, and 96 h after SiRNA transfection determined by Western blotting. The RAD51 protein level 48 h after transfection of HEK cells with scrambled siRNA (denoted as "sc siRNA") was expressed as 100%. Purified RAD 51 (3.2 ng) was used as a marker. FIG. 26B is a graphical depiction of the results of FIG. 26A.

FIG. 27 illustrates the finding that Compound B02 inhibits HR by disrupting RAD51 binding to DNA. During the repair of DNA double-strand breaks, RAD51 binds to ssDNA forming the nucleoprotein filament. The filament searches for homologous dsDNA sequence to form joint molecules. The homologous DNA then is used as a template for DNA polymerase. Dissociation of the joint molecules and re-annealing of DNA ends lead to the restoration of the DNA structure. Compound B02 inhibits HR by disrupting formation of the RAD51-ssDNA filament and interaction of the filament with dsDNA during the search for homology.

FIG. 28, comprising FIGS. 28A-28B, illustrates the finding that Compound B02 does not affect RAD51 oligomerization. FIG. 28A illustrates the elution profiles of RAD51 (13.5 µM) that was either untreated (dashed curve) or treated (solid curve) with B02 (200 µM) for 10 min at 37° C. prior to chromatography on a Superose 6 10/300 GL column (GE Healthcare). 0.3-ml fractions were collected. The void volume (7.5 ml) and the protein markers (thyroglobulin, 670 kDa; γ-globulin, 158 kDa; ovalbumin, 44 kDa; myoglobin, 17 kDa) are indicated. FIG. 28B illustrates the fractions analyzed by 12% SDS-PAGE. Prestained molecular weight markers and a RAD51 marker are shown in lanes 1 and 14, respectively.

DETAILED DESCRIPTION OF THE INVENTION

Figure 1B:
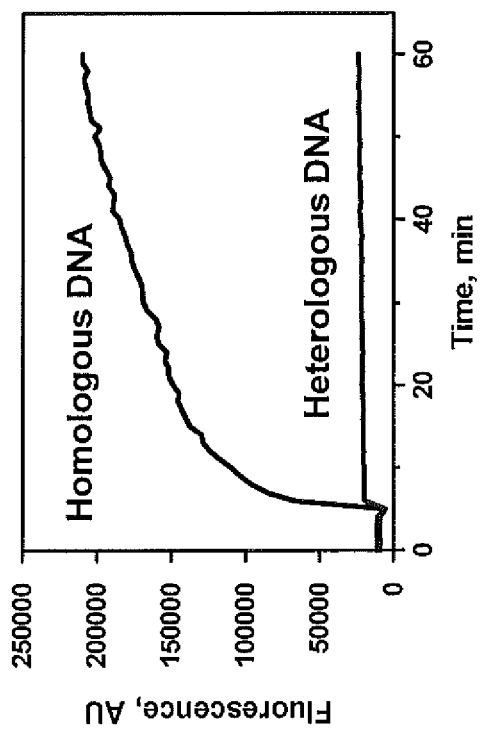
FIGS. 1A-1B, illustrates the process of measuring RAD51-promoted DNA strand exchange using the FRET-based assay.

This invention includes the unexpected identification of novel selective small-molecule RAD51 inhibitors and their utility in the treatment of cancer. In order to identify selective RAD51 inhibitors, an efficient high throughput screening (HTS) of chemical compound libraries was performed using an assay based on fluorescence resonance energy transfer (FRET). Compounds found to inhibit RAD51 DNA strand exchange activity were further analyzed by the D-loop assay (a secondary non-fluorescent DNA strand exchange assay), and potent RAD51 inhibitors were then identified.

Due to their unique mechanism, the compounds contemplated within the invention are useful in overcoming the chemoresistance and radioresistance of human cancers. In one aspect, treatment of a subject with compounds contemplated within the invention enhances cell sensitivity to radiation treatments or chemotherapeutic agents, such as DNA cross-linking agents, cisplatin and mitomycin C. In another aspect, a subject treated with compounds contemplated within the invention along with a chemotherapeutic agent and/or radiation enjoys greater overall efficacy in the cancer treatment and/or prevention, as compared to the efficacy observed with the same dose of chemotherapeutic agent and/or radiation alone. In yet another aspect, a subject treated with compounds contemplated within the invention may be treated with lower doses of the chemotherapeutic agent and/or radiation of choice, and still experience similar efficacy in cancer treatment and/or prevention, as compared to the standard dose of chemotherapeutic agent and/or radiation. This has the advantage of reducing complications due to toxicity from radiation therapy or chemotherapy, and reducing recovery times for the subject.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemisty, analytical chemistry and organic chemistry and those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element. The term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "chemotherapeutic agent" or "chemotherapeutic agent" refers to a chemical compound, chemical conjugate, peptide, protein, antibody and the like that finds use in treating, preventing, or reducing the symptoms of cancer.

As used herein, the term "BHQ1" or "black hold quencher 1" refers to the following moiety or a derivative (here, BHQ1 is illustrated as bound to a 5'-oligo through a phosphate bond):

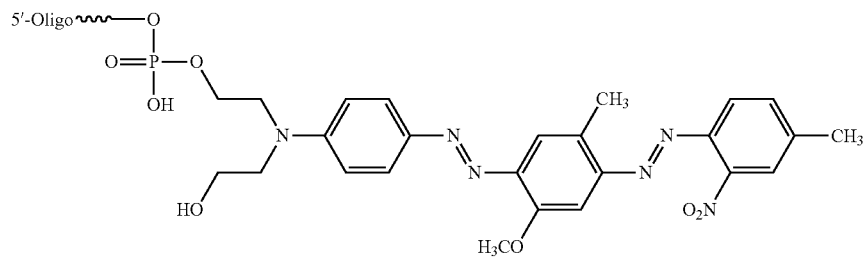

As used herein, the term "EBVQ", Compound B02 or Compound Ia are interchangeable and refer to (E)-3-benzyl-2-(2-(pyridin-3-yl)vinyl)quinazolin-4(3H)-one or a salt thereof.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, protein variants, modified proteins, derivatives, analogs, and fusion proteins, among others. The proteins include natural proteins, recombinant proteins, synthetic proteins, or a combination thereof. A protein may be a receptor or a non-receptor.

As used herein, amino acids are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", 3$^{rd}$ Ed., W. H. Freeman and Co., New York.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "fragment," as applied to a protein or peptide, refers to a subsequence of a larger protein or peptide. A "fragment" of a protein or peptide may be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "DNA" as used herein is defined as deoxyribonucleic acid.

The term "RNA" as used herein is defined as ribonucleic acid.

The term "recombinant DNA" as used herein is defined as DNA produced by joining pieces of DNA from different sources.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleotides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropymethyl.

As used herein, the term "substituted alkyl" means alkyl, as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_{1-C4}$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O) OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quatomized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$OH, CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-$(C_1-C_3)$alkyl" means a functional group wherein a one to three carbon alkylene chain is attached to an aryl group, e.g., —CH$_2$CH$_2$-phenyl. Preferred is aryl-CH$_2$— and aryl-CH(CH$_3$)—. The term "substituted aryl-$(C_1-C_3)$alkyl" means an aryl-$(C_1-C_3)$alkyl functional group in which the aryl group is substituted. Preferred is substituted aryl(CH$_2$)—. Similarly, the term "heteroaryl-$(C_1C_3)$alkyl" means a functional group wherein a one to three carbon alkylene chain is attached to a heteroaryl group, e.g., —CH₂CH₂-pyridyl. Preferred is heteroaryl-(CH₂)—. The term "substituted heteroaryl-(C₁-C₃)alkyl" means a heteroaryl-(C₁C₃)alkyl functional group in which the heteroaryl group is substituted. Preferred is substituted heteroaryl-(CH₂)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzoluryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sufolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-trizolyl, 1,2,4-triazolyl, 1,3,4-triazolyl, tetrazolyl, 1,2,3-thiodiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particulary 3-, 4-, 5-, 6- and 7-benzofuryl), 2,3-dihydrobenzofuryl, 1,2-benzisoxazolyl, benzothienyl (particulary 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-(C₁-C₃)alkyl and hetercyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessibly position. In one embodiment, the substituents vary in number between one and four. In another embodiment, the substituents vary in number between one and three. In yet another embodiment, the substituents vary in number between one and two. In yet another embodiment, the substituents vary in independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy group, acetamido, and nitro. As used herein, where a substituent is an alkyl or alkoxy group, the carbon chain may be branched, straight or cyclic, with straight being preferred.

By the term "specifically binds," as used herein, is meant a molecule, such as an antibody or a small molecule, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measureable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, acrosol, parenteral, ophthalmic, pulmonary and topical administration.

"Pharmaceutically acceptable" refers to those properties and/or substances which are acceptable to the patient from a pharacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil corn oil and soybean oil; glycols, such as propylene glycol; polyols, such as glycerins, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, aralipathic, heterocyclic, carboxylic and sulfonic classes or organic acids, examples of which include formic, acetic, propionic, succinic, glycolic, gluconic, lactic, malic, tartaric, citric, ascorbic, gluouronic, maleic, fumaric, pyruvic, aspartic, glutamic, benzoic, anthranilic, 4-hydroxybenzioc, phenylacetic, mandelic, embomic (pamoic), methanesulfonic, ethanesulfonic, benzenesulfonic, pantothenic, trifluoromethanesulfonic, 2-hydroxyethanesulfonic, p-toluenesulfonic, sulfanille, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethyenediamine, meglumine (N-methyl-glucamine) and procaine. All of these salts may be prepared by conventional means from the corresponding free base compound by reacting, for example, the appropriate acid or base with the corresponding free base.

An "individual", "patient" or "subject", as that term is used therein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis. A therapeutic effect is obtained by suppression, remission, or eradication of UVR-induced skin damage.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition ant the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publications or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds Useful Within the Invention

In one aspect, the compound useful within the compositions and methods of the invention is the compound of Formula (1):

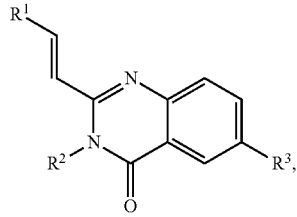

(1)

wherein:
$R^1$ and $R^2$ independently H, $C_1$-$C_6$ alkyl, $C_1$-$C_6$ substituted alkyl, phenyl, substituted phenyl, heteroaryl, substituted heteroaryl, heterocycyl, substituted heterocyclyl, —($C_1$-$C_6$) alkylene-phenyl, —($C_1$-$C_6$)alkylene-substituted phenyl, —($C_1$-$C_6$)alkylene-heteroaryl, or —($C_1$-$C_6$)alkylene-substituted heteroaryl;
$R^3$ is H, $C_1$-$C_6$ alkyl, O—($C_1$-$C_6$ alkyl), F, Cl, Br or I; or a salt thereof.

In one embodiment, $R^1$ is H, methyl, phenyl, substituted phenyl, heteroaryl, substituted heteroaryl, —($C_1$-$C_6$)alkylene-phenyl, —($C_1$-$C_6$)alkylene-substituted phenyl, —($C_1$-$C_6$)alkylene-heteroaryl, or —($C_1$-$C_6$)alkylene-substituted heteroaryl. In another embodiment, $R^1$ is phenyl, substituted phenyl, heteroaryl, or substituted heteroaryl. In yet another embodiment, $R^1$ is phenyl, o-tolyl, m-tolyl, p-tolyl, o-methoxyphenyl, m-methoxyphenyl, p-methoxyphenyl, o-halophenyl, m-halophenyl, p-halophenyl, o-nitrophenyl, m-nitrophenyl, p-nitrophenyl, 2-pyridinyl, 3-pyridinyl, or 4-pyridinyl.

In one embodiment, $R^2$ is H, $C_1$-$C_6$ alkyl, phenyl, substituted phenyl, heteroaryl, substituted heteronryl, —($C_1$-$C_6$)alkylene-phenyl, —($C_1$-$C_6$)alkylene-substituted phenyl, —($C_1$-$C_6$)alkylene-heteroaryl, or —($C_1$-$C_6$)alkylene-substituted heteroaryl. In another embodiment, $R^2$ is $C_1$-$C_6$ alkyl, phenyl, substituted phenyl, heteroaryl, substituted heteroaryl, —($C_1$-$C_6$)alkylene-phenyl, or —($C_1$-$C_6$)alkylene-substituted phenyl. In yet another embodiment, $R^2$ is methyl, ethyl, n-propyl, isopropyl, phenyl, o-tolyl, m-tolyl, p-tolyl, benzyl or substituted benzyl.

In one embodiment, $R^3$ is H, $C_1$-$C_6$ alkyl, O($C_1$-$C_6$ alkyl), F or Cl. In another embodiment, $R^3$ is H, $C_1$-$C_6$ alkyl, or O($C_1$-$C_6$ alkyl). In yet another embodiment, $R^3$ is H, methyl, ethyl, methoxy or ethoxy. In yet another embodiment, $R^3$ is H.

In one embodiment, the compound of Formula (1) is selected from the group consisting of:

(E)-3-benzyl-2-(2-(pyridin-3-yl)vinyl)quinazolin-4(3H)-one (1a)

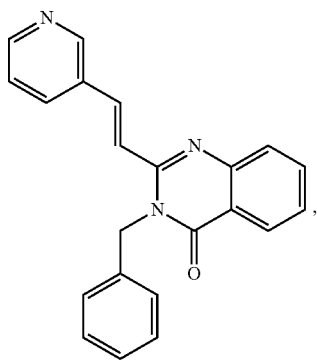

(E)-3-ethyl-2-(2-(pyridin-3-yl)vinyl)quinazolin-4(3H)-one (1b)

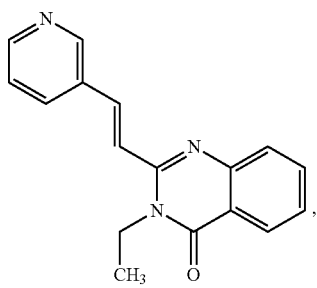

(E)-2-(2-(pyridin-3-yl)vinyl)-3-(m-tolyl)quinazolin-4(3H)-one (1c)

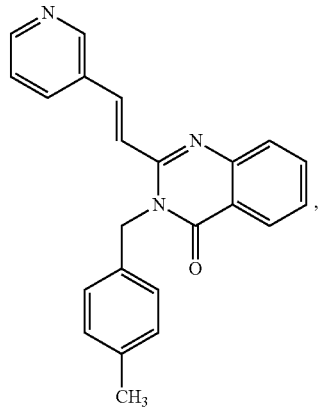

mixtures thereof and salts thereof.

In another aspect, the compound useful within the compositions and methods of the invention is salazinic acid, also known as 1,4,10-trihydroxy-5-(hydroxymethyl)-8-methyl-3,7-dihydro-1H-benzo[6,7][1,4]dioxepino[2,3-e]isobenzofuran-11-carbaldehyde, which has formula (2):

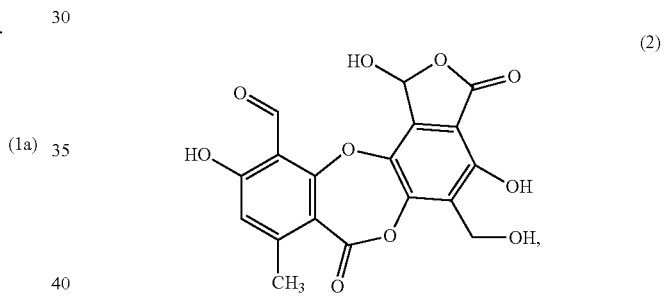

or a salt therof.

In yet another aspect, the compound useful within the compositions and methods of the invention is stictic acid, also known as scopularic acid or 1,4-dihydroxy-10-methoxy-5,8-dimethyl-3,7-dioxo-3,7-dihydro-1H-benzo[6,7][1,4]dioxepino[2,3-e]isobenzofuran-11-carbaldehyde, which has formula (3):

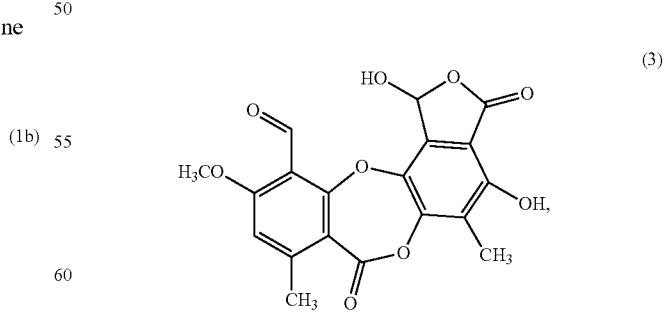

or a salt thereof.

Compounds useful within the methods of the invention may be synthesized using techniques well-known in the art of organic synthesis or obtained from commercial sources.

Compositions of the Invention

In one aspect, the invention includes a pharmaceutical composition comprising a compound of Formula (1) and a pharmaceutically acceptable carrier. In one embodiment, the pharmaceutical composition further comprises a chemotherapeutic agent. In another embodiment, the agent is selected from the group consisting of an alkylating agent, antimetabolite, anthracycline, plant alkaloid, plant terpenoid, topoisomerase inhibitor, and antineoplastic.

In another aspect, the invention includes a pharmaceutical composition comprising a compound of Formula (2), a chemotherapeutic agent, and a pharmaceutically acceptable carrier.

In another aspect, the invention includes a pharmaceutical composition comprising a compound of Formula (3), a chemotherapeutic agent, and a pharmaceutically acceptable carrier.

Salts of the Compounds of the Invention

The compounds described herein may form salts with acids or bases, and such salts are included in the present invention. In one embodiment, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hudroxybutyric, salicyclic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base.

Methods of Invention

The invention includes a method of treating or preventing cancer in a subject in need thereof. The method comprises the step of administering to the subject a pharmaceutical compound comprising a pharmaceutically acceptable carrier and a pharmaceutically effective amount of a compound of Formula (1):

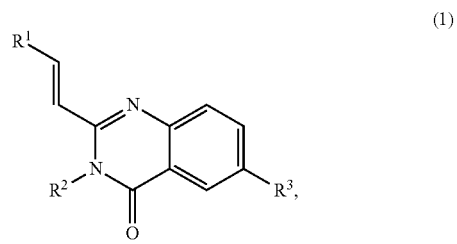

wherein $R^1$ and $R^2$ are independently H, $C_1$-$C_6$ alkyl, $C_1$-$C_6$ substituted alkyl, phenyl, substituted phenyl, heteroaryl, substituted heteroaryl, heterocyclyl, substituted heterocyclyl, —($C_1$-$C_6$)alkylene-phenyl, —($C_1$-$C_6$)alkylene-substituted phenyl, —($C_1$-$C_6$)alkylene-heteroaryl, or —($C_1$-$C_6$)alkylene-substituted heteroaryl;

$R^3$ is H, $C_1$-$C_6$ alkyl, O($C_1$-$C_6$alkyl), F, Cl, Br or I; or a salt thereof. The method further comprises the step of administering to the subject a treatment selected from the group consisting of (i) radiation therapy, and (ii) a pharmaceutical composition comprising a pharmaceutically effective amount of a chemotherapeutic agent, whereby treating or preventing the cancer in the subject.

In one embodiment, the compound of Formula (1) is selected from the group consisting of (E)-3-benzyl-2-(2-(pyridin-3-yl)vinyl)quinazolin-4(3H)-one (1a), (E)-3-ethyl-2-(2-(pyridin-3-yl)vinyl)quinazolin-4(3H)-one (1b), (E)-2-(2-(pyridin-3-yl)vinyl)-3-(m-tolyl)quinazolin-4(3H)-one (1c), mixtures thereof and salts thereof.

In one embodiment, administering of the compound of Formula (1) is performed at least 24 hours prior to administering to the subject the radiation therapy or the chemotherapeutic agent. In another embodiment, administering of the compound of Formula (1) is performed at least 12 hours prior to administering to the the radiation therapy or the chemotherapeutic agent. In yet another embodiment, administering of the compound of Formula (1) is performed at least 6 hours prior to administering to the subject the radiation therapy or the chemotherapeutic agent. In yet another embodiment, administering of the compound of Formula (1) is performed at least 3 hours prior to administering to the subject the radiation therapy or the chemotherapeutic agent. In yet another embodiment, administering of the compound of Formula (1) is performed at least 1 hour prior to administering to the subject the radiation therapy or the chemotherapeutic agent. In yet another embodiment, the composition comprising the compound of Formula (1) is co-administered to the subject with the radiation therapy or the composition comprising the chemotherapeutic agent. In yet another embodiment, the compound of Formula (1) and the chemotherapeutic agent are co-formulated in a pharmaceutical composition. In yet another embodiment, the subject is a human.

The invention also includes a method of treating or preventing cancer in a subject in need thereof. The method comprises the step of administering to the subject a pharmaceutical composition comprising a pharmaceutically acceptable carrier and a pharmaceutically effective amount of a compound of Formula (2):

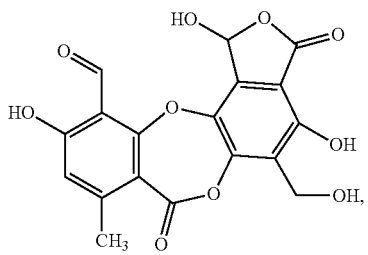

(2)

or a salt thereof. The method further comprises the step of administering to the subject a treatment selected from the group consisting of (i) radiation therapy, and (ii) a pharmaceutical composition comprising a pharmaceutically effective amount of a chemotherapeutic agent; whereby treating or preventing the cancer in the subject.

In one embodiment, administering of the compound of Formula (2) is performed at least 24 hours prior to administering to the subject the radiation therapy or the chemotherapeutic agent. In another embodiment, administering of the compound of Formula (2) is performed at least 12 hours prior to administering to the subject the radiation therapy or the chemotherapeutic agent. In yet another embodiment, administering of the compound of Formula (2) is performed at least 6 hours prior to administering to the subject the radiation therapy or the chemotherapeutic agent. In yet another embodiment, administering of the compound of Formula (2) is performed at least 3 hours prior to administering to the subject the radiation therapy or the chemotherapeutic agent. In yet another embodiment, administering of the compound of Formula (2) is performed at least 1 hour prior to administering to the subject the radiation therapy or the chemotherapeutic agent. In yet another embodiment, the composition comprising the compound of Formula (2) is co-administered to the subject with the radiation therapy or the composition comprising the chemotherapeutic agent. In yet another embodiment, the compound of Formula (2) and the chemotherapeutic agent are co-formulated in a pharmaceutical composition. In yet another embodiment, the subject is a human.

The invention further includes a method of treating or preventing cancer in a subject in need thereof. The method comprises the step of administering to the subject a pharmaceutical composition comprising a pharmaceutically acceptable carrier and a pharmaceutically effective amount of a compound of Formula (3):

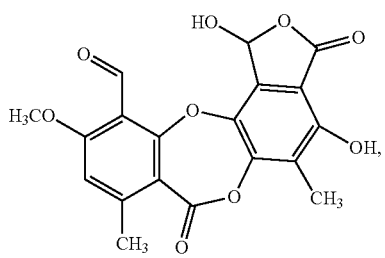

(3)

or a salt thereof. The method further comprises the step of administering to the subject a treatment selected from the group consisting of (i) radiation therapy, and (ii) a pharmaceutical composition comprising a pharmaceutically effective amount of a chemotherapeutic agent; whereby treating or preventing the cancer in the subject.

In one embodiment, administering of the compound of Formula (3) is performed at least 24 hours prior to administering to the subject the radiation therapy or the chemotherapeutic agent. In another embodiment, administering of the compound of Formula (3) is performed at least 12 hours prior to administering to the subject the radiation therapy or the chemotherapeutic agent. In yet another embodiment, administering of the compound of Formula (3) is performed at least 6 hours prior to administering to the subject the radiation therapy or the chemotherapeutic agent. In yet another embodiment, administering of the compound of Formula (3) is performed at least 3 hours prior to administering to the subject the radiation therapy or the chemotherapeutic agent. In yet another embodiment, administering of the compound of Formula (3) is performed at least 1 hour prior to administering to the subject the radiation therapy or the chemotherapeutic agent. In yet another embodiment, the composition comprising the compound of Formula (3) is co-administered to the subject with the radiation therapy or the composition comprising the chemotherapeutic agent. In yet another embodiment, the compound of Formula (3) and the chemotherapeutic agent are co-formulated in a pharmaceutical composition. In yet another embodiment, the subject is a human.

Combination Therapies

The compounds contemplated within the invention or salts thereof may be useful in the methods of present invention in combination with radiation therapy and/or a compound useful for treating cancer (generally referred to as "chemotherapeutic agent"). These additional compounds may comprise compounds of the present invention or compounds (such as commercially available compounds) known to treat, prevent, or reduce the symptoms of cancer. In one embodiment, the combination of a compound contemplated within the invention and a chemotherapeutic agent has additive, complementary or synergistic effects in the treatment of cancer in a subject, or prevention of cancer in a subject. In another embodiment, the combination of a compound contemplated within the invention and radiation therapy has additive, complementary or synergistic effects in the treatment of cancer in a subject, or prevention or cancer in a subject.

Radiation Therapy

In one aspect, a compound contemplated within the invention or a salt thereof may be used in combination with radiation therapy.

Radiation therapy, radiation oncology, or radiotherapy, sometimes abbreviated to XRT, is the medical use of ionizing radiation as part of cancer treatment to control malignant cells. Radiotherapy may be used to curative or adjuvant treatment. It is used as palliative treatment (where cure is not possible and the aim is for local disease control or symptomatic relief) or as therapeutic treatment (where the therapy has survival benefit and it can be curative).

Radiotherapy is used for the treatment of malignant cancer, and may be used as a primary or adjuvant modality. It is also common to combine radiotherapy with surgery, chemotherapy, hormone therapy, immunotherapy or a mixture of the four. Most common cancer types can be treated with radiotherapy in some way. The precise treatment intent (curative, adjuvant, neoadjuvant, therapeutic, or palliative) will depend on the tumor type, location, and stage, as well as the general health of the patient.

Radiation therapy is commonly applied to the cancerous tumor. The radiation fields may also include the draining lymph nodes if they are clinically or radiologically involved with tumor, or if there is thought to be a risk of subclinical malignant spread. Brachytherapy, in which a radiation source is placed inside or next to the area requiring treatment, is another form of radiation therapy that minimizes exposure to healthy tissue during procedures to treat cancers of the breast, prostate and other organs.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery.

Chemotherapeutic Agents

In one aspect of the invention, a compound of the invention or a salt thereof may be used in combination with a chemotherapeutic agent.

In one embodiment, a compound of the invention is co-administered with a chemotherapeutic agent to the subject in need thereof. In another embodiment, a compound of the invention and a chemotherapeutic agent are administered to the subject as part of the same pharmaceutical formulation. In yet another embodiment, a compound of the invention and a chemotherapeutic agent are administered separately to the subject in need thereof.

Most of the approved chemotherapeutic agents may be divided into alkylating agents, antimetabolites, anthracyclines, plant alkaloids and terpenoids, topoisomerase inhibitors, antineoplastics and other antitumour agents. These drugs affect cell division or DNA synthesis and function directly or indirectly.

Some newer chemotherapeutic agents do not directly interfere with DNA synthesis and function. These include monoclonal antibodies and tyrosine kinase inhibitors e.g. imatinib mesylate (Gleevec or Glivec), which directly targets a molecular abnormality in certain types of cancer (chronic myelogenous leukemia, gastrointestinal stromal tumors), and are generally referred to as targeted therapies.

In addition, some drugs that modulate tumor cell behavior without directly attacking those cells, such as hormones, may be used in the treatment of cancer.

Non-limiting examples of chemotherapeutic agents are provided below.

Alkylating Agents:

Alkylating agents alkylate nucleophilic functional groups present in cells. They impair cell function by forming covalent bonds with the amino, carboxyl, sullhydryl, and phosphate groups in biologically important molecules, and in particular by chemically modifying a cell's DNA. Cisplatin, carboplatin, oxaliplatin, mechlorethamine, cyclophosphamide, chlorambucil, and ifosfamide are alkylating agents.

Anti-Metabolites:

Anti-metabolites masquerade as purines (azathioprine, mercaptopurine) or pyrimidines, which are building blocks of DNA. By competing out naturally occurring purines or pyrimidines, anti-metabolites prevent these building blocks from becoming incorporated into DNA during the "S" phase (of the cell cycle), thus stopping normal development and division. Anti-metabolites also affect RNA synthesis. Due to their efficiency, anti-metabolites are the most widely used cytostatics.

Plant Alkaloids and Terpenoids:

These plant alkaloids block cell division by preventing microtubule function. Microtubules are vital for cell division, and, without them, cell division cannot occur. The main examples of plant alkaloids are vinca alkaloids and taxanes.

(a) Vinca Alkaloids

Vinca alkaloids bind to specific sites on tubulin, inhibiting assembly of tubulin into microtubules (M phase of the cell cycle). The vinca alkaloids include vincristine, vinblastine, vinorelbine and vindesine.

(b) Podophyllotoxin

Podophyllotoxin is a plant-derived compound said to help with digestion and used to produce two other cytostatic drugs, etoposide and teniposide. They prevent the cell from entering the GI phase (the start of DNA replication) and the replication of DNA (the S phase). The exact mechanism of its action is unknown. The substance has been primarily obtained from the American Mayapple (*Podophyllum peltatum*). Recently it has been discovered that a rare Himalayan Mayapple (*Podophyllum hexandrum*) contains it in a much greater quantity, but, as the plant is endangered, its supply is limited. Studies have been conducted to isolate the genes involved in the substances's production, so that it could be obtained recombinantly.

(c) Taxanes

The prototype taxane is the natural product paclitaxel, originally known as Taxol and first derived from the bark of the Pacific Yew tree. Ducetaxel is a semi-synthetic analogue of paclitaxel. Taxanes enhance stability of microtubules, preventing the separation of chromosomes during anaphase.

Topoisomerase Inhibitors:

Topoisomerase are essential enzymes that maintain the topology of DNA. Inhibition of type I or type II topoisomerases interferes with both transcription and replication of DNA by upsetting proper DNA supercoiling. Type I topoisomerase inhibitors include camptothecins: irinotecan and topotecan. Type II inhibitors include amsacrine, etoposide, etoposide phosphate, and teniposide. These are semisynthetic derivatives of epipodephylltoxins, alkaloids naturally occurring in the root of American Mayapple (*Podophyllum peltatum*).

Antineoplastics:

These include the immunosuppressant dactinomycin (which is used in kidney transplantations), doxorubicia, epirubicin, bleomycin and others.

Anticancer agents working through different cytotoxic mechanisms may also be combined in "chemotherapy regimens" in order to target a specific type of cancer. Chemotherapy regimens are often identified by acronyms, identifying the agents used in combination. However, the letters used are not consistent across regimens, and in some cases (for example, "BEACOPP"), the same letter combination is used to represent two different treatments. Non-limiting examples of combinations used in clinical settings are listed below, in terms of acronyms, compositions and cancer types:

ABVD: Adriamycin (doxorubicin), bleomycin, vinblastine, dacarbazine—Hodgkins's lymphoma AC: Adriamycin (doxorubicin), cyclophosphamide—Breast cancer BEACOPP: Bleomycin, etoposide, Adriamycin (doxorubicin), cyclophosphamide, Oncovin (vincristine), procarbazine, prednisone—Hodgkin's lymphoma BEP: Bleomycin, etoposide, platinum agent (cisplatin)—Testicular cancer, germ cell tumors CA: Cyclophosphamide, Adriamycin (doxorabicin) (same as AC)—Breast cancer CAF: Cyclophosphamide, Adriamycin (doxorubicin), fluorouracil (5-FU)—Breast cancer CAV: Cyclophosphamide, Adriamycin (doxorubicin), vincristine—Lung cancer CBV: Cyclophosphamide, BCNU (carmustine), VP-16 (etoposide)—Lymphoma ChIVPP/EVA: Chlorambucil, vincristine (Oncovin), procarbazine, prednisone, etoposide, vinblastine, Adriamycin (doxorubicin)—Hodgkin's lymphoma CHOP: Cyclophosphamide, hydroxydoxorabicin (doxorubicin), vincristine (Oncovin), prednisone—Non-Hodgkin lymphoma CHOP-R or R-CHOP: CHOP—rituximab—B cell non-Hodgkin lymphoma COP or CVP: Cyclophosphamide, Oncovin (vincristine), prednisone—Non-Hodgkin lymphoma in patients with history of cardiovascular disease CMP: Cyclophosphamide, methotrexate, fluorouracil (5-FU)—Breast cancer COPP: Cyclophosphamide, Oncovin (vincristine), procarbazine, prednisone—Non-Hodgkin lymphoma EC: Epirubicin, cyclophosphamide—Breast cancer ECF: Epirubicin, cisplatin, fluorouracil (5-FU)—Gastric cancer and oesophageal cancer EP: Etoposide, platinum agent (cisplatin)—Testicular cancer, germ cell tumors EPOCH: Etoposide, prednisone, Oncovin, cyclophosphamide, and hydroxydaunorubicin—Lymphomas FEC: Fluorouracil (5-FU), epirubicin, cyclophosphamide—Breast cancer FL (Also know as Mayo): Fluorouracil (5FU), leucovocin (folinic acid)—Colorectal cancer FOLFOX: Fluorouracil (5-FU), leucovorin (folimic acid), oxaliplatin—Colorectal cancer FOLFIRI: Fluorouracil (5-FU), leucovorin (folimic acid), irinotecan—Colorectal cancer ICE: ifosfamide, carboplatin, etoposide (VP-16)—Aggressive lymphomas, progressive neuroblastoma ICE-R: ICE+rituximab—High-risk progressive or recurrent lymphomas m-BACOD: Methotrexate, bleomycin, Adriamycin (doxorubicin), cyclophosphamide, Oncovin (vincristine), dexamethasone—Non-Hodgkin lymphoma MACOP-B: Methotrexate, leucovorin (folinic acid), Adriamycin (doxorubicin), cyclophosphamide, Oncovin (vincristine), prednisone, bleomycin—Non-Hodgkin lymphoma MOPP: Mechlorethamine, Oncovin (vincristine), procarbazine, prednisone—Hodgkin's lymphoma MVAC: methotrexate, vinblastine, adriamycin, cisplatin—Advanced bladder cancer[2]

PCV: Procarbazine, CCNU (lomustine), vincristine—Brain tumors

ProMACE-MOPP: Methotrexate, Adriamycin (doxorubicin), cyclophosphamide, etoposide+MOPP—Non-Hodgkin lymphoma ProMACE-CytaBOM: Prenisone, doxorubicin (adriamycin), cyclophosphamide, etoposide, cytarabine, bleomycin, Oncovin (vincristine), methotrexate, leucovorin—Non-Hodgkin lymphoma R-FCM: Rituximab, fludarabine, cyclophosphamide, mitoxantrone—B cell non-Hodgkin lymphoma Stanford V: Doxorubicin, mechlorethamine, bleomycin, vinblastine, vincristine, etoposide, prednisone—Hodgkin's lymphoma Thal/Dex: Thalidomide, dexamethasone—Multiple myeloma TIP: Paclitaxel, ifosfamide, platinum agent cisplatin—Testicular cancer, germ cell tumors in salvage therapy VAC: Vincristine, Actinomycin, Cyclophasphamide—Rhabdomyosarcoma VAD: Vincristine, Actinomycin (doxorubicin), dexamethasone—Multiple myeloma VAPEC-B: Vincristine, Actinomycin (doxorubicin), prednisone, etoposide, cyclophosphamide, bleomycin—Hodgkin's lymphoma VIP: Etoposide, ifosfamide, platinum agent cisplatin—Testicular cancer, germ cell tumors A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the media-effect equation (Chou & Talulay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in the pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commerically relevant mammals such as non-human primates, cattle, pigs, horses, sheep, cats, and dogs.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 µg to about 10 mg per kilogram of body weight of the animal. More preferably, the dosage will vary from about 3 µg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a pharmaceutically acceptable carrier or one or more other accessory ingredients, and then, if necessary or desirable, shaping or packaging the product into a desire single- or multi-dose unit.

A pharmaceutical composition of the invention may be prepared, packaged, or solid in bulk, as a single unit does, or as a plurality of single unit doses. As used herein, a "unit does" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mark Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the ease of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combination thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.01% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demalcents, preservatives, buffers, salts, flavorings, coloring agents, and sweetening agents. Oily suspensions may further comprise a thickening agent. Knows suspending agents include, but are not limited to, sorbitol syrup, hydrogenated edible fats, sodium alginate, polyvinylpyrrolidone, gum tragaeanth, gum acacia, and cellulose derivatives such as sodium carboxymethylcellulose, methylcellulose, hydroxyproplmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspension, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilities the controlled-release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carrier out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 0.1 mg to about 1,000 mg, about 0.2 mg to about 950 mg, about 0.4 mg to about 900 mg, about 1 mg to about 850 mg, about 5 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the composition of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of Administration

Routes of administration of any of the compositions of the invention include oral, nasal, rectal, parenteral, sublingual, transdermal, transmucousal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way or example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the composition of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolldone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wad-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrastemal injection, intralumural, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way or a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drub delivery are electroporation, sonophoresis, iontophorsesis, permeation enhancers (cyclodextrins), and liposomes. While the aforementioned methods are also included in the present invention for dermal delivery of the compounds of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% sorbic acid.

The composition preferably includes an antioxidant and a chelating agent which inhibit the degradation of the compound for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g., disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (eg., olive oil/PEG7), biovera oil, wax (eg., jojoba wax), squalene, myristate (eg., isopropyl myristate), triglycerides (eg., captylic triglyceride), Solulan 98, cocoa butter, shea butter, alcohol (eg., behenyl alcohol), stearate (eg., glycerol-monostearate), chelating agents (eg., EDTA), propylene gylcol SEPIGEL (Seppic, Inc., Fairfield, N.J.), silicone and silicone derivatives (eg., dimethicone, cyclomethicone), vitamins (eg., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical compositions of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilities the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulations that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Kits of the Invention

The invention also includes a kit comprising a compound useful within the methods of the invention and an instructional material that describes, for instance, administering the compound to a subject as a prophylactic or therapeutic treatment for cancer as described elsewhere herein. In one embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

Proteins and DNA:

RecA was purchased from USB Inc. (Cleveland, Ohio). Human RAD51 and RAD54 were purified as described (Sigurdsson et al., 2001, J. Biol. Chem. 276:8798-8806; Mazina & Mazin, 2004, J. Biol. Chem. 279:52042-51). The oligonucleotides used in this study were purchased from IDT Inc. (San Diego, Calif.) in a desalted form.

Oligonucleotide and pUC19 DNA substrates were prepared as described (Bugreev et al., 2006, Nature Protocols, published online Sep. 1, 2006; Rossi et al, Methods 51:336-46). ΦX174 ssDNA and dsDNA were purchased from New England Biolabs (Ipswich, Mass.) and Invitrogen (Carlsbad, Calif.), respectively. The DNA concentrations are expressed as moles of nucleotide.

(E)-3-benzyl-2-(2-(pyridin-3-yl)vinyl)quinazolin-4(3H)-one) (Compound B02) was purchased from Ryan Scientific Inc. (Mt. Pleasant, S.C.). Poly [ADP-ribose]polymerase 1 (PARP1) inhibitor AZD2281 (olaparib or 4-[(3-[(4-cyclopropylcarbonyl) piperazin-4-yl]carbonyl)-4-fluorophenyl]methyl(2H)phthalazin-I-one) was purchased from Selleck Chemicals LLC (Houston, Tex.). Cis-dichlorodiamine platinum (II) (cisDDP) and Mitomycin C (MMC) were purchased from Sigma-Aldrich (St. Louis, Mo.). Gapped DNA was prepared by annealing the pBSK (1) XhoI-AlwNI fragment (2065 bp) to pBSK (+) ssDNA and purified as described previously.

Cell Culture:

Mouse embryonic fibroblasts (MEF) and Tp53−/−MEF cells are gifts from Dr. Astrinidis (Rajesh et al., 2010, DNA Repair (Arnst) 9, 458-67; Matthew et al., E. M., 2009, Cell Cycle 8, 4168-75). 293 human embryonic kidney (HEK) cells with intrachromosomally based GFP (DRGFP) reporter system (Pierce et al, 1999, Genes Dev. 13:2633-38), as well as pCBASSce (Pierce et al., 1999, Genes Dev. 13:2633-38) and pMX-GFP (Cell Biolabs, Inc. San Diego, Calif.) plasmids are gifts from Dr. Clifford.

Except otherwise indicated, all cell lines were maintained in Dalbecco's Modified Eagle medium (DMEM) (Sigma-Aldrich, St. Louis, Mo.) supplemented with 10% fetal bovine serum (FBS) (Invitrogen, Carlsbad, Calif.), 100 units/ml penicillin and 100 μg/ml streptomycin (Sigma-Aldrich, St. Louis, Mo.) in the presence of 5% $CO_2$ at 37° C.

Compound Libraries:

The NIH Small Molecule Repository (202,556 compounds) was used for the primary screening for RAD51 inhibitors. All the compounds were dissolved in DMSO (Sigma-Aldrich, St. Louis, Mo.); concentration of stock solutions were 2.5 mM or 5 mM. In the working solutions the DMSO concentration added with the stock of compounds was 2% (v/v), unless indicated otherwise. The compounds for SAR analysis were purchased from Chembridge Co. (San Diego, Calif.).

Fluorescence-Based Strand Exchange Assay:

A fluorescence-based assay was developed to measure the RAD51 DNA strand exchange activity. In this assay, dsDNA substrate was prepared by annealing two complementary ssDNA oligonucleotides Oligo 25-FLU (fluorescein-25-FLU contains the fluorescein group, a donor fluorophore with the excitation maximum at 490 nm and the emission maximum at 521 nm, at the 5'-end. Oligo 26-BHQ1 contains the black hole quencher I (BHQI), a non-fluorescent acceptor, at the 3'-end. To form the nucleoprotein filament, RAD51 (200 nM) was incubated with a 48-mer ssDNA (Oligo 25; SEQ ID NO:2) (600 nM, nt) in DNA strand exchange buffer containing 40 mM Tris-HCl (pH 7.8), 2 mM ATP, 5 mM $CaCl_2$, 1 mM DTT and 100 μg $ml^{-1}$ BSA for 15 min at 37° C. DNA strand exchange was initiated by addition of dsDNA (600 nM, nt) (Oligo 25-FLU: fluorescein-SEQ ID NO:3; Oligo 26-BHQI; SEQ ID NO:4-Black Hole Quencher I). $Ca^{2+}$ strongly stimulates DNA strand exchange activity of RAD51, but not that of the yeast and bacterial RAD51 homologues (Bugree & Mazin, 2004, Proc. Natl. Acad. Sci. 101:9988-93). The reactions were carried out for indicated period of time at 37° C. or 23° C., as indicated. The fluorescence intensity was measured using a Fluoromax3 fluorimeter (Jobin Yvon, Edison, N.J.).

HTS of the NIH SMR for RAD51 Inhibitors:

To form the nucleoprotein filament, RAD51 (300 nM) was incubated with a 48-mer ssDNA (SEQ ID NO:2) (600 nM, nt) in DNA strand exchange buffer containing 40 mM HEPES (pH 7.8), 2 mM ATP, 5 mM $CaCl_2$, 1 mM DTT and 100 μg $ml^{-1}$ BSA for 15 min at 37° C. 10 μl aliquots of the mixtures were added to the plates containing the NIH Small Molecule Repository and further incubated at 23° C. for 30 min. DNA strand exchange reactions were initiated by addition of dsDNA (300 nM, nt) (fluorescein-SEQ ID NO:3 and SEQ ID NO:4-Black Hole Quencher 1) and carried out at 23° C. for 15 min, or otherwise indicated periods of time. Compound concentration was 8.5 μM, unless indicated otherwise, DMSO concentrations in wells was 1.7% (v/v). HTS of chemical compound libraries was performed in 384 or 1536 well plates using a Perkin Elmer Envision 2102 multilabel reader. The compounds with an inhibitory effect of 30% or greater were tested further by measuring the concentration dependence (in a range from 1 nM to 100 μM) of their inhibition of RAD51. The most potent inhibitory compounds were analyzed further using non-fluorescent assays.

D-Loop Assay for RAD51:

The D-loop assay was performed essentially as described previously (Bugreev & Mazin, 2004, Proc. Natl. Acad. Sci. 101:9988-93). To form the nucleoprotein filament, RAD51 protein (1 μM) was incubated with $^{32}$P-labeled 90 mer ssDNA (SEQ ID NO:6) (3 μM, nt) in buffer containing 25 mM Tris-acetate (pH 7.5), 1 mM ATP, 1 mN $CaCl_2$, 100 μg $ml^{-1}$ BSA, 1 mM DTT and 20 mM KCl for 15 min at 37° C. When indicated, chemical compounds in question were added in specified concentrations and incubation was continued for 30 min at 37° C. D-loop formation was initiated by addition of supercoiled pUC19 dsDNA (50 μM, nt) and continued for 15 min. Reactions were stopped by addition of SDS to 1% (w/v) and proteinase K to 880 μg $ml^{-1}$ followed by incubation for 15 min at 37° C. Samples were mixed with 0.1 vol of loading buffer (70%(v/v) glycerol, 0.1% (w/v) bromophenol blue) and analyzed by electrophoresis in 1% (w/v) agarose-TAE (40 mM Tris-acetate, pH 8.0 and 1 mM EDTA) gels. The yield of joint molecules was expressed as a percentage of the total plasmid DNA.

To measure the kinetics of D-loop formation, RAD51 protein (0.3 μM) was incubated with $^{32}$P-labeled ssDNA (SEQ ID NO:6, 90 mer) (0.9 μM, nt) in buffer containing 25 mM Tris-acetate (pH 7.5), 1 mM ATP, 1 mM $CaCl_2$, 100 μg/ml BSA, 1 mM DTT and 20 mM KCl for 15 min at 37° C. after (FIG. 11A, I) or before (FIG. 11A, II) incubation with Compound B02 (20 μM) for indicated time at 37° C. Then the D-loop formation was initiated by addition of 15 μM of supercoiled dsDNA (pUC19). The reaction was deproteinized and analyzed as described above.

D-Loop Assay for RecA:

To form the nucleoprotein filament RecA protein (1 μM) was incubated with 90 mer $^{32}$P-labeled ssDNA (SEQ ID NO:6) (3 μM, nt) in buffer containing 25 mM Tris-acetate (pH 7.5), 1 mM ATP, 10 mM $MgCl_2$, 100 μg $ml^{-1}$ BSA, 1 mM DTT, 3 mM phosphoenolpyruvate and 5 U $ml^{-1}$ pyruvate kinase for 5 min at 37° C. (Mazin et al., 2000, EMBO J. 19:1148-56). When indicated, chemical compounds in specified concentrations were added and incubation was continued for 30 min at 37° C. D-loop formation was initiated by addition of supercoiled pUC19 dsDNA (50 μM, nt) and carried out for 3 min at 37° C. The DNA products were deproteinized and analyzed as described above for the Rad51-promoted reaction.

Three Strand Exchange Assay:

RAD51 (1.0 μM) was incubated with indicated concentrations of Compound B02 in buffer containing 25 mM Tris-acetate (pH 7.5), 250 mM NaCl, 2 mM ATP, 1 mM DTT, 10 mM $MgCl_2$, and 2 mM $CaCl_2$ for 30 min at 37° C. Then φX174 circular ssDNA (4.0 μM) was added to the reaction mix to form the nucleoprotein filaments followed by 5 min incubation, then RPA (0.27 μM) was added followed by another 5 min incubation. Reactions were initiated by addition of $^{32}$P labeled linear φX174 dsDNA (4.0 μM) (DNA form I cleaved by ApaLI endonuclease). The reaction was stopped and DNA was deproteinized by addition of SDS to 1% and proteinase K to 880 μg/ml and incubation for 15 min at 37° C. Samples were mixed with 0.1 vol of loading buffer (70% glycerol, 0.1% bromophenol blue) and analyzed by electrophoresis in 1% agarose-TAE (40 mM Tris acetate, pH 8.0 and 1 mM EDTA) gels; gels were quantified by using a Storm 840 PhosphorImager (Molecular Dynamics).

DNA Branch Migratin Assay for RAD54:

The partial Holliday junction (PX-junction), in which one of the four DNA arms is single-stranded (FIG. 6A), was used as a substrate for the 4-stranded branch migration promoted by RAD54 (Mazina et al., 2007, J. Biol. Chem. 282:21068-80). PX junctions were constructed in such a way (by incorporating a region of heterology) that allowed branch migration only in one direction (Bugreev et al., 2006, Nature 442: 590-93). To produce PX-junctions, tailed DNA (Oligo 170, SEQ ID NO:9, Oligo 171, SEQ ID NO:10) (1.45 µM, molecules) was annealed with $^{32}$P-labeled fork DNA (Oligo 71; SEQ ID NO:7; Oligo 169, SEQ ID NO:8) (1.33 µM, molecules) in branch migration buffer containing 25 mM Tris acetate, pH 7.5, 3 mM magnesium acetate, 2 mM ATP, 1 mM dithiothreitol, 100 µg ml$^{-1}$ bovine serum albumin, 10 U ml$^{-1}$ creatine phosphokinase, 15 mM creatine phosphate for 10 min at 37° C. and then for 10 min at 30° C. Then, branch migration was initiated immediately by addition of the RAD 54 (100 nM) to PX-junctions (33 nM, molecules) in branch migrtion buffer and was carried out at 30° C. Aliquots (10 µl) were withdrawn after 0, 3, 5, 15, 30, and 60 min. The DNA products were deproteinized by treatment with stop buffer (1.4% (w/v) SDS, 960 µg ml$^{-1}$ proteinase K, 7.5% (w/v) glycerol, 0.015% (w/v) bromphenol blue) for 5 min at 22° C. and analyzed by electrophoresis in 8% (w/v) polyacrylamide gels (29:1) in 1×TBE buffer (89 mM Tris borate, pH 8.3, and 1 mM EDTA) at 22° C. The gels were dried on DE81 chromatography paper (Whatman, Kent, UK) and quantified using a Storm 840 PhosphorImager (Molecular Dynamics, Piscataway, N.J.).

Branch Migration Assay:

For RAD51-promoted reaction, RAD51 (1 µM) was incubated with B02 in the indicated concentrations in buffer containing 30 mM Tris HCl, pH 7.5, 10 mM MgCl$_2$, 350 mM NaCl, 2 mM DTT, 2 mM ATP, 8 mM phosphocreatine, and 8 units/ml cretine phosphokinase for 30 min at 37° C. Branch migration was initiated by addition of $^{32}$P-labeled 3'-joint molecule (0.1 nM, molecule) that were produced by RAD51-promoted reaction and was carried out for 8 h. For RecA-promoted reaction, RecA (1 µM) was incubated with B02 in the indicated concentrations in buffer containing 25 mM Tris acetate, pH 7.5, 15 mM magnesium acetate, 2 mM DTT, 2 mM ATP, 10 mM phosphocreatine, and 10 units/ml creatine phosphokinase for 30 min at 37° C. Branch migration was initiated by addition of $^{32}$P-labeled 3'-joint molecules (0.1 nM, molecules) that were produced by RecA-promoted reactin and was carried out for 30 min. The DNA products were deproteinized and analyzed in 1.5% agarose-TAE gels and quantified using a Storm 840 PhosphorImager (GE Healthcare).

Ethidium Bromide Displacement Assay:

Ethidium bromide (0.5 mg ml$^{-1}$) was added to pUC19 supercoiled dsDNA (2 µg ml$^{-1}$) in buffer containing 25 mM Tris acetate, pH 7.5, 20 mM NaCl, and 10 µM EDTA followed by 1 min incubation. The fluorescence of the sample was measured using a FlouroMax-3 fluorimeter at an extension wavelength of 260 nm and an emission wavelength of 546 nm. Then, the small molecule inhibitors were added in increasing concentrations and allowed to equilibrate for 1 min, followed by the fluorescence measurement.

Calculation of IC$_{50}$ Value for RAD51 Inhibitors:

IC$_{50}$ values were calculated using GraphPad Prism V5.0 software and the sigmoidal dose-response function. The data were obtained from three independent repeats of experiments.

DNA Binding Assay:

DNA binding assay was performed as described (Bugreev et al., 2005, J. Biol. Chem. 280:26886-95). Briefly, 1.0 µM RAD51 protein and 25 µM Compound B02 were incubated in buffer containing 25 mM Tris-acetate (pH 7.5), 2 mM ATP, 100 µg/ml BSA, 1 mM DTT and 2 mM CaCl$_2$ for 30 min at 37° C., then $^{32}$P-labeled ssDNA (SEQ ID NO:6, 90 mer) (2.5 µM) and NaCl in indicated concentrations were added to the reaction mixture. After 10 min, reactions was mixed with 0.2 vol of loading buffer and loaded on 10% polyacrylamide gels (135 V, 20 mA) in 0.5×TBE buffer containing 45 mM Tris borate (pH 8.3) and 0.25 mM EDTA. Gels were quantified using a Storm 840 PhosphorImager.

ATPase Assay:

RAD51 (1 µM) was incubated with Compound B02 in indicated concentrations in buffer containing 25 mM Tris-acetate (pH 7.5), 1 mM DTT, 100 µg/ml bovine serum albumin (BSA), 2 mM Mg(OAc)$_2$, 0.1 mM ATP and 10 µCi [γ-$^{32}$P] ATP(6000 Ci/mmole) for 30 min at 37° C. Then ssDNA (#90, SEQ ID NO:6, 90 mer) (3 µM, nt) was combined to the reactions. After 1.5 h, the samples were applied on polyethyleneimine cellulose strips and subjected to thin layer chromatography (PEI-TLC) developed in 1 M formic acid/0.5 M LiCl. The fraction of the inorganic [$^{32}$P] phosphate (Pi) released from [γ-$^{32}$P] ATP was quantified by using a Storm 840 PhosphorImager (Molecular Dynamics).

dsDNA Coaggregation Assay:

To measure the effect of Compound B02 on the dsDNA to the secondary RAD51 binding site, the DNA coaggregation assay was pre-formed as described (Tsang etal., 1985, Biochemistry 24:3226-32). RAD51 protein (1 µM) was incubated with ssDNA (#71, SEQ ID NO:7, 94 mer) (3 µM, nt) in buffer containing 25 mM Tris-HCl, pH 7.5, 1 mM ATP, 100 µg/ml BSA, 1 mM DTT, 20 mM KCl (added with the protein stocks) and 2 mM CaCl$_2$ for 15 min at 37° C. Then Compound B02 (20 µM) was added to the mixture followed by addition of NaCl in indicated concentrations and coaggregation was initiated immediately by addition of $^{32}$P-labeled pUC19 dsDNA (linearized by BamHI restriction endonuclease, 25 µM, nt). After 10 min incubation at 37° C. aliquois (10 µl) were withdrawn from the reaction mixture and coaggregates were collected by centrifugation in 0.5-ml Eppendorf tubes at 15,000×g for 5 min at 21° C. The yield of coaggregates was quantified using a LS 6500 liquid scintillation counter (Beckman). Residual retention of the radioactive DNA on the tube walls, ~2-3% of total radioactivity, was substracted from the measurements.

DR-GFP Assay for Homologous Recombination in Human Cells:

To measure the effect of Compound B02 to the efficiency of DSB- induced homologous recombination in human cells a chromosomally located DR-GFP reporter system in 293 human embryonic kidney (HEK) cells was used (Pierce et al., 1999, Genes Dev. 13:2633-38). 293 HEK cells expressing DR-GFP were grown until the log phase. Then cells were harvested and replated in 6-well plates (TPP, Switzerland) (pre-coated by 0.1% w/v poly-L-Lysine) with the density of 4.5×10$^5$ cells/well; after 24 hr, media were refreshed, then Compound B02 in indicated concentrations was added followed by 1 h incubation at 37° C. Then a 200 µl mixture containing 2 µg of pCBASce supercoiled plasmid DNA encoding I-SceI rare-cutting restriction endonuclease (Richardson et al., 1998, Genes Dev. 12:3831-42) and 6 µl of GenDrill™ transfection reagent (BarnaGen BioScience LLC) in Opti-MEM® I Reduced-Serum (Invitrogen) was added to each well. After 2 days incubation, cells were trypsinized and diluted to density of 200 cells/µl in PBS (10 mM Na$_2$HPO$_4$, 1.76 mM KH$_2$PO$_4$, 137 mM NaCl and 2.7 mM KCl, pH 7.4) for Fluorescence Activated Cell Sorting (FACS) analysis on a Guava EasyCyte Plus System (Millipore, Billerica, Mass).

Effect of Compound B02 on Transfection Efficiency of pMX-GFP Plasmid into 293 HEK Cells and Expression of GFP Protein:

The log-phase 293 HEK cells containing the DR-GFP reporter were incubated with Compound B02 in indicated concentrations for 1 h at 37° C. Transfection was carried out by addition of a 200 µl mixture containing 2 µg of pMX-GFP supercoiled plasmid DNA encoding GFP protein and 6 µl of GenDrill™ transfection reagent (BarnaGen BioScience LLC) in Opti-MEM® I Reduced-Serum (Invitrogen) to each well. After 2 days incubation, cells were trypsinized and diluted to density of 200 cells/µl in PBS buffer for Fluorescence Activated Cell Sorting (FACS) anaylsis on a Guava EasyCyte Plus System (Millipore, Billerica, Mass.).

Detectin of Level of RAD51 and SceI Expression by Western Blotting:

HEK-GFP cells were incubated on 10-cm tissue culture plates in DMEM® until ~70% confluence, then treated with B02 in indicated concentrations for 24 h, trypsinized, resuspended in DMEM+, and precipitated by centrifugation at 1,000×g for 5 min at 4° C. The pellets were washed three times with cold PBS and then resuspended in lysis buffer containing 50 mM HEPES, pH 7.5, 50 mM NaCl, 5 mM EDTA, 1% Triton X-100, 50 mM NaF, and 10 mM Na$_4$P$_2$O$_7$, 1 mM PMSF, and proteinase inhibitor cocktail (Roche Applied Science) for 30 min at 4° C. The cell lysates were centrifuged at 16,000×g, for 15 min at 4° C., and then the supernatants were collected and protein concentrations were determined using the Bradford assay. Aliquots containing 50 µg of total protein were analyzed by 12% SDS-PAGE. After electrophoresis, the proteins were transferred on a polyvinylidene fluoride (PVDF) membrane (Osmonics, Inc) using a Mini Trans-Blot cell (Bio-Rad) at 70 V for 3 h at 4° C., and RAD51 was visualized using anti-RAD51 IgG rabbit polyclonal antibodies (gift of Dr. Etim Golub) (1:5,000 dilution) and horseradish peroxide-conjugated goat antirabbit secondary antibodies (Santa Cruz Biotechnology) (1:1000 dilution) in 1×TBST buffer (10 mM Tris-HCl, pH 8.0, 150 mM NaCl, 0.1% v/v Tween 20) supplemented with 4% nonfat milk.

To determine the expression level of RAD51 log-phase 293 HEK cells carrying the DRGFP were incubated on 10 cm tissue culture plates in DMEM media supplemented with 10% FBS, 100 units/ml penicillin and 100 µg/ml streptomycin containing Compound B02 in indicated concentrations cells reach confluence (~24 h); to determine the expression level of I-SceI restriction endonuclease, log-phase cells were treated by Compound B02 in indicated concentrations for 1 h, and them transfected with pCBASce plasmid DNA followed by incubation on 10 cm tissue culture plates until complete cell confluence (~64 h). Then, both pCBASce-transfected and untransfected cells were trypsinized and resuspended in DMEM supplemented with 10% FBS, 100 units/ml penicillin and 100 µg/ml streptomycin. The suspensions were centrifuged at 1000×g for 5 min at 4° C., the pellets were washed 3 times with cold PBS and then resuspended in lysate buffer containing 50 mM HEPES (pH 7.5), 50 mM NaCl, 5 mM EDTA, 1% Triton X-100, 50 mM NaF, and 10 mM Na$_4$P$_2$O$_7$, 1 mM phenylmethylsulfonyl fluoride (PMSF) and proteinase inhibitor cocktail (Roche Applied Science) for 30 min at 4° C. The cell lysates were centrifuged at 16000×g, for 15 min at 4° C. The supernatants were collected and protein concentrations were determined by the Bradford assay using bovine serum albumin (BSA) as a standard. Equivalent amounts of proteins were loaded on 12% SDS-PAGE gels and after electrophoretic separation were transferred on a PVDF membrane (Osmonics, Inc). For lysates from untransfected cells, RAD51 protein was probed with anti-RAD51 IgG rabbit polyelonal antibodies (kind gift of Dr. Efim Golub, Yale University) and horseradish peroxidase conjugated goat anti-rabbit secondary antibodies (Santa Cruz Biotechnology); for lysates from pCBASec-transfected cells, I-SceI protein containing the HA antigen was probed with HA-Tag (6E2) mouse monoclonal antibodies (Cell Signaling Technology) and horseradish peroxidase-conjugated donkey anti-mouse secondary antibodies (Santa Cruz Biotechnology). Immunoblot signals were detected using Enhanced Chemiluminescence (ECL) reagent (Pierce). To strip the antibodies, the membranes were incubated for 30 min at 50° C. with occasional agitation in a solution containing 2% SDS, 62.5 mM Tris-HCl, pH 6.8, and 100 mM β-mercaptoethanol before reprobing with anti-β-actin antibodies.

Clonogenic Survival Assay:

To test the sensitivity of MEF cells to DNA-damaging agents in the absence or presence of Compound B02 (5 µM), the clonogenic survival assay was used as described (Essers et al., 1997, Cell 89:195-204). Briefly, MEF cells were trypsinized and the appropriate number of cells was replated on 10 cm tissue culture dishes. After overnight culture, cells were incubated for 1 h in media containing Compound B02 (5 µM), followed by addition of mitomycin-C (MMC) or cis-dichlorodiamine platinum (II) (cisDDP) in indicated concentrations and additional incubation for 1 h. Then the cells were washed 3 times with PBS buffer and incubated in media containing Compound B02 (5 µM) for 7-10 days. Cells were fixed and stained using staining (0.05% crystal violet, 50% methanol in PBS); colonies were counted using a Alphalmager 3400 (Alpha Innotech Inc.). The percent of survival was determined as described (Hall & Giccia, 2005, "Radiobiology for the Radiologist", 6$^{th}$ Ed., Philadelphia, Pa.: Lippincott Williams & Wilkins, pp. 30-45). The percent of survival obtained from untreated cells was normalized to 100% survival.

Joint Molecule Formation Assay:

For RAD51-promoted reaction, RAD51 (1 µM) was incubated with B02 in the indicated concentrations in buffer containing 25 mM Tris acetate, pH 7.5, 2 mM ATP, 275 mM NaCl, 1 mM MgCl$_2$, 1 mM CaCl$_2$, 1 mM DTT, and 100 µg/mL BSA for 20 min at 37° C., and the pBSK (+) gapped DNA 4 µM, nt) was added to form nucleoprotein filaments for 15 min. RPA (80 nM) was added to the mixture followed by at 10-min incubation. Joint molecule formation was initiated by addition of 5'-labeled linear pBSK (+) dsDNA (4 µM, nt) (linearized by XhoI) and carried out for 2 h.

For RecA-promoted reaction, RecA (1 µM) was incubated with indicated concentrations of B02 in buffer containing 33 mM Tris HCl, pH 7.5, 3 mM MgCl$_2$, 2 MM DTT, 100 µg/ml BSA, 10 mM phosphocreatine, and 10 units/ml creatinine phosphokinase for 30 min at 37° C., and then pBSK (+) gapped DNA (5 µM, nt) was added to form the nucleoprotein filaments for 10 min. Joint molecule formation was initiated by addition of 3'-labeled linear pBSK (+) dsDNA (4 µM, nt) (linearized by AlwNI) and single-stranded DNA binding protein (SSB) (82.5 nM) protein and carried out for 20 min.

In RAD51 and RecA-promoted reactions, joint molecules were deproteinized by addition of SDS to 1% and proteinase K to 880 µg mL$^{-1}$ and incubation for 15 min at 37° C. 0.1 vol of loading buffer (70% glycerol, 0.1% bromophenol blue) was added and joint molecules were either analyzed by electrophoresis in 1% agarose-TAE (40 mM Tris-acetate, pH 8.0, and 1 mM EDTA) gels and quantified using a Storm 840

PhosphorImager (GE Healthcare); or joint molecules were passed twice through S-400 Spin columns (GE Healthcare) equilibrated with 25 mM Tris-acetate, pH 7.5, at 23° C., and used as substances in branch migration reactions.

Measurement of B02 Binding to RAD51 by SPR:

Experiments were performed using the ProteOn XPR36 SPR array system with ProteOn Manager Software version 3.0 (Bio-Rad). ProteOn GLH sensor chips were preconditioned with two short pulses each (10 s) of 50 mM NaOH, 100 mM HCl, and 0.5% SDS. The system was then equilibrated with PBS-T buffer (20 mM Na-phosphate, 150 mM NaCl, and 0.005% Tween 20, pH 7.4). Individual ligand flow channels were activated for 5 min at 25° C. with a mixture of 1-ethyl-3-[3-dimethylaminopropyl carbodiimide hydrochloride) (0.2 M) and sulfo-N-hydroxysuccinimide (0.05 M). Immediately after chip activation, either RAD51 (6.8 µM in 10 mM sodium acetate, pH 4.5), RecA (2.6 µM in 10 mM sodium acetate, pH 4.5), or HIV-INL4-3 capsid protein (0.5 µM in 10 mM sodium acetate, pH 5.0) was injected across ligand flow channels for 5 min at a flow rate of 30 µl min-1. Excess active ester groups on the sensor surface were capped by a 5-min injection of 1 M ethanolamine-HCl (pH 8.5). This resulted in the coupling of RAD51, RecA, and CA to 14,000, 9,000, and 17,000 RUs (response unit, which is an arbitrary unit that corresponds to 1 pg/mm2), respectively. The standard deviation in the immobilization level from the six spots within each channel was less than 4%. B02 in indicated concentrations in buffer S containing 25 mM Tris-acetate, pH 7.5, 100 µM $CaCl_2$, 3% DMSO, and 100 µM ATP (when indicated) was injected over the control or RAD51 chips at a flow rate of 100 µl min-1, for 2-min association phase, followed by a 15-min dissociation phase at 25° C. using the "one-shot" functionality of the ProteOn. Specific regeneration of the surfaces between injections was not needed owing to the nature of the interaction. Data were analyzed using the ProteOn Manager Software version 3.0 (Bio-Rad). The responses of a buffer injection and responses from the reference flow cell were subtracted to account for nonspecific binding. Experimental data were fitted globally to a simple 1:1 binding model. The average kinetic parameters (association [ka] and dissociation [kd] rates) generated from three data sets were used to define the equilibrium dissociation constant ($K_d$).

Effect of B02 on RAD51 Oligomerization:

RAD51 (50 µg) was incubated in either the presence or absence of B02 (200 µM) in 100 µl buffer E (35 mM Tris-acetate; pH 7.5, 150 mM NaCl, 10% v/v glycerol 1 mM ATP, 1 mM $CaCl_2$, and 14.3 mM β-mercaptoethanol) for 10 min at 37° C. The samples were then centrifuged for 15 min at 16,000×g, 4 C. Supernatants were loaded on a Superose 6 10/300 GL column (GE Healthcare) equilibrated with buffer E and eluted with a flow rate of 0.2 ml/min at 4° C. The gel filtration molecular weight marker kit (29-669 kDa, Sigma) was used for column calibration. The 0.3-ml fractions were collected and analyzed by electrophoresis in a 12% SDS-PAGE gel (100 V, 90 min).

Transfection of HEK Cells with siRNA:

To suppress RAD51 expression, HEK cells were transfected with 100 nM RAD51 siRNA (sc-36361; Santa Cruz Biotechnology). Briefly, cells ($1 \times 10^6$) were seeded in a 3.5-cm tissue culture plate and incubated overnight, then the medium was removed and the cell layer was washed three times with PBS. Transfection was carried out by adding 1 ml transfection solution containing 100 pmol (1.25 µg) siRNA and 10 µl siRNA transfection reagent (sc-29528; Santa Cruz Biotechnology) in Opti-MEM I Reduced-Serum medium (Invitrogen) to each plate. Six to 7 hours after transfection the medium was replaced with fresh DMEM+. Twenty-four, 48, 72, and 96 h after transfection, the RAD51 level was determined using Western blotting. As a specificity control scrambled siRNA (sc-37007; Santa Cruz Biotechnology) was used instead of RAD51 siRNA.

RAD51 Foci Formation:

$2 \times 10^5$ log phase HEK-GFP cells were seeded in 3.5-cm tissue culture plates on glass coverslips protreated with 0.01% poly-L-lysine (Sigma) and grown overnight. The cells were then incubated with B02 (50 µM) or without B02 for 2 h at 37° C. Cells were then exposed to 0.5 Gy IR using a Primus Linear Accelerator (Siemens) at 6 mV, 3 Gy/min followed by a 2-h incubation at 37° C. Cells were washed with phosphate-buffered saline (PBS) (8.1 mM $Na_2HPO_4$, 1.47 mM $KH_2PO_4$, 138 mM NaCl and 2.7 mM KCl, pH 7.4), extracted with PBS containing 0.2% Triton X-100 and 1 mM phenylmethanesulfonylfluoride (PMSF) for 5 min at 4° C., and fixed with PBS supplemented with 3.0% formaldehyde and 2.0% sucrose for 10 min. Cells were permeabilized with PBS containing 0.5% Triton X-100 for 5 min and blocked with PBS containing 3% BSA and 0.05% Tween 20 for 30 min at 23° C. Cells were treated with the polyclonal rabbit RAD51 antibodies (1:500 dilution) (a gift from Dr. Golub, Yale University) in PBS containing 3% BSA and 0.05% Triton X-100 overnight at 4° C., and then with Alexa Fluor 488 donkey antirabbit IgG (H+L) antibodies (1:1000 dilution) (Invitrogen) for 1 h at 23° C. followed by a 5-min staining with 500 ng/ml 4',6-diamidino-2-phenylindole (DAPI) in PBS containing 0.05% Tween 20. Samples were washed in PBS containing 0.05% Tween 20, mounted in VectaShield™ (Vector Laboratories), and sealed with nail polish. The fluorescence images were obtained using an Olympus IX70 inverted microscope and iVision-Mac™ software (BioVision).

Example 1

Fluorescence-Based DNA Strand Exchange Assay

Figure 1A:
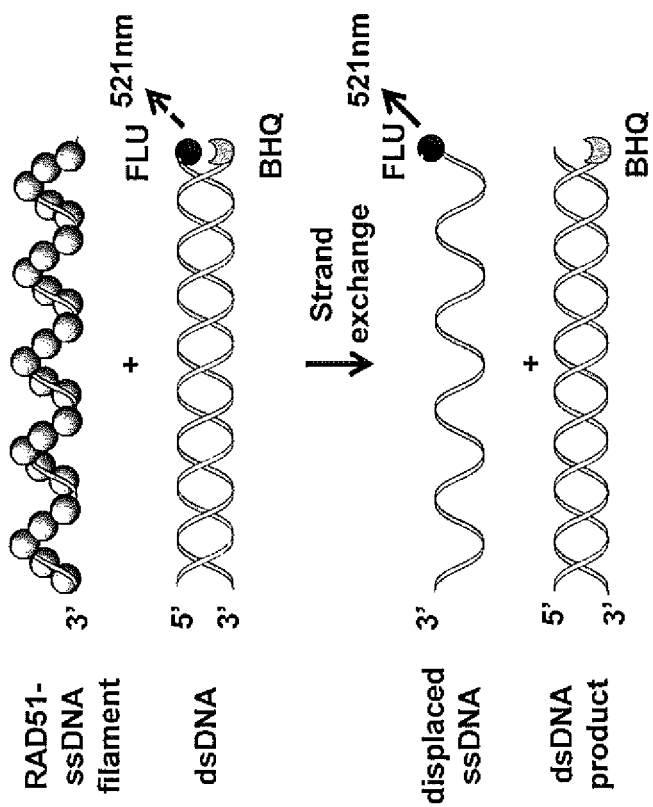

A FRET-based DNA strand exchange assay suitable for HTS of large libraries of chemical compounds was developed. In this assay, RAD51 promotes DNA strand exchange between homologous synthetic ssDNA and dsDNA substrates. The dsDNA carries fluorescein (FLU), a fluorescent donor group, and black hole quencher 1 (BHQ1), a non-fluorescent acceptor group, which were attached to the 5'- and 3'-ends of the complementary ssDNA strands, respectively (FIG. 1A). In this dsDNA substrate, the fluorescence at he FLU group is quenched by BHQ1 through FRET. As a result of RAD51-promoted DNA strand exchange, the FLU-carrying DNA strand is displaced from the dsDNA that carries the BHQ1 and the fluorescence of the FLU group increases (Parkhurst & Parkhurst, 1995, Biochem. 34:293-300; Parkhurst et al., 2001, Biopol. 61:180-200).

Using this assay the kinetics of RAD51-promoted DNA strand exchange was measured. RAD51 was loaded on the homologous ssDNA (SEQ ID NO:2; 48-mer) (denoted as "Homologous DNA") to form the nucleoprotein filament. Then, fluorescently labeled dsDNA (SEQ ID NO:4-Black Hole Quencher 1; and fluorescein-SEQ ID NO:3) was added to the filament to initiate DNA strand exchange. After a 1 h incubation the fluorescence intensity at 521 nm increased approximately 20-fold (FIG. 1B). To ensure that the observed fluorescence increase resulted from DNA strand exchange, a control was run in which the RAD51 filament was assembled on heterologous ssDNA (SEQ ID NO:5, 48-mer) (denoted as "Heterologous DNA"). Since DNA strand exchange does not occur between heterologous DNA molecules (Shibata et al., 1979, Proc. Natl. Acad. Sci. 76:1638-42), no increase in fluorescence was expected. Indeed, in the case of heterologous DNA the intensity of fluorescence remained almost constant during the 1 h of incubation (FIG. 1B). Thus, the results validated the FRET-based assay to measure the DNA strand exchange activity of RAD51.

Example 2

HTS of the NIH Small Molecule Repository

Figure 2A:
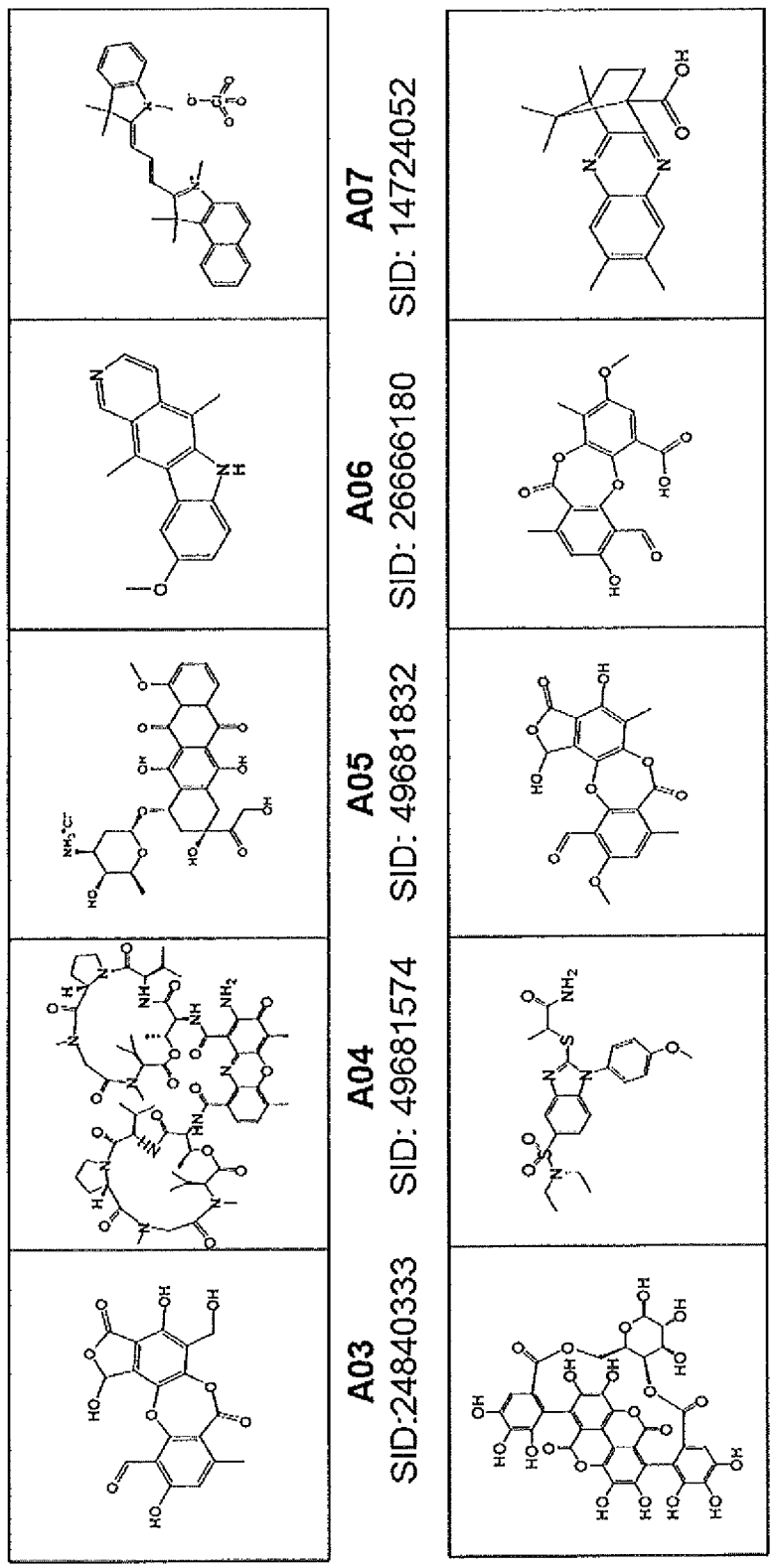
FIGS. 2A-2B, illustrates selected RAD51 inhibitors identified by HTS.
Figure 2B:
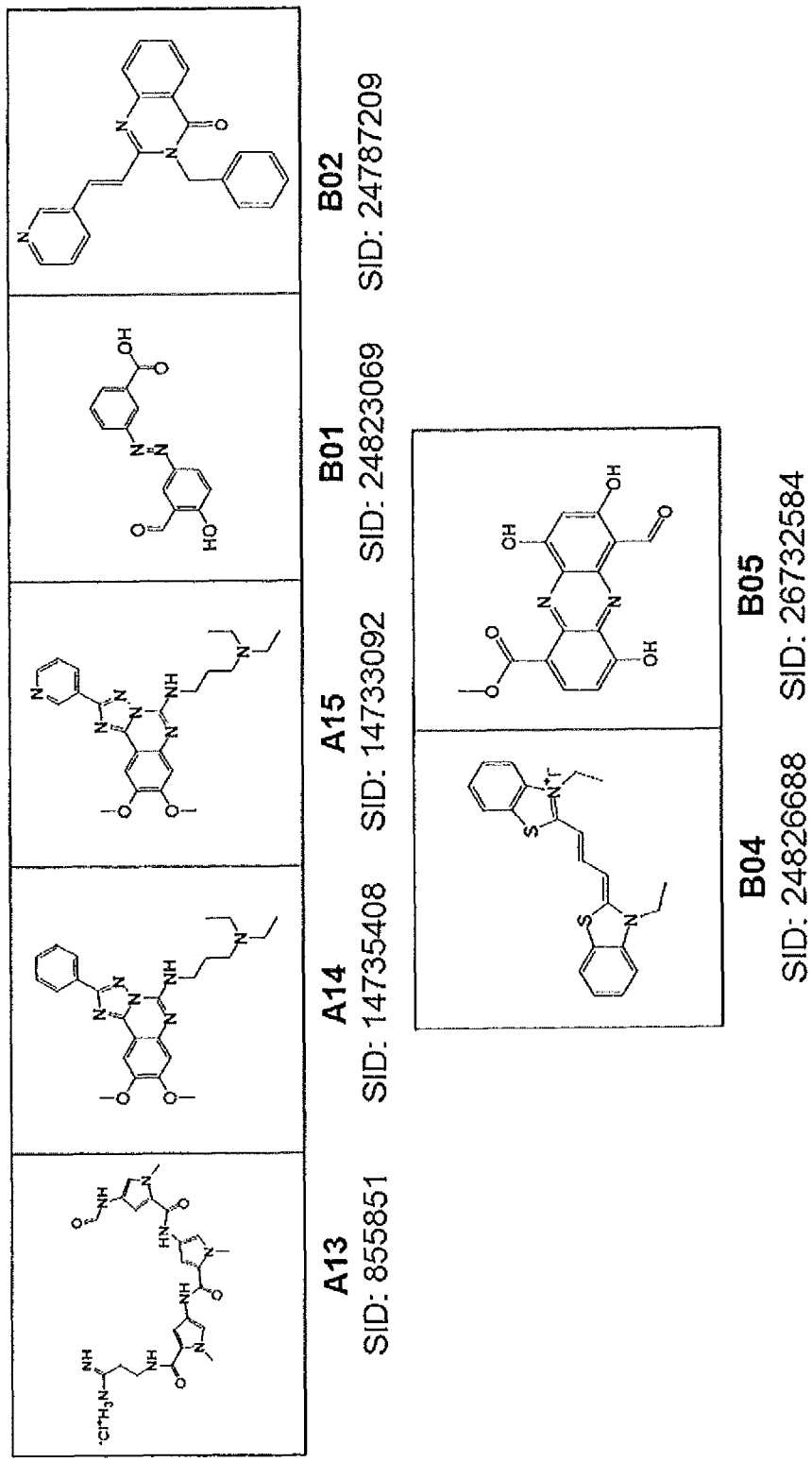

The NIH Small Molecule Repository (202,556 compounds) was screened for RAD51 inhibitors using the FRET-based assay described above. 174 positive hits that showed more than 30% inhibition of the DNA strand exchange activity of RAD51 were detected (hit rate, 0.09%) using a Perkin Elmer Envision 2102 multilabel reader. Measuring the concentration dependence of RAD51 inhibition by these compounds allowed the identification of the seventeen most potent inhibitors as candidates that warranted further analysis (FIG. 2).

Example 3

Analysis of RAD51 Inhibitors Using the D-loop Assay

Figure 3C:
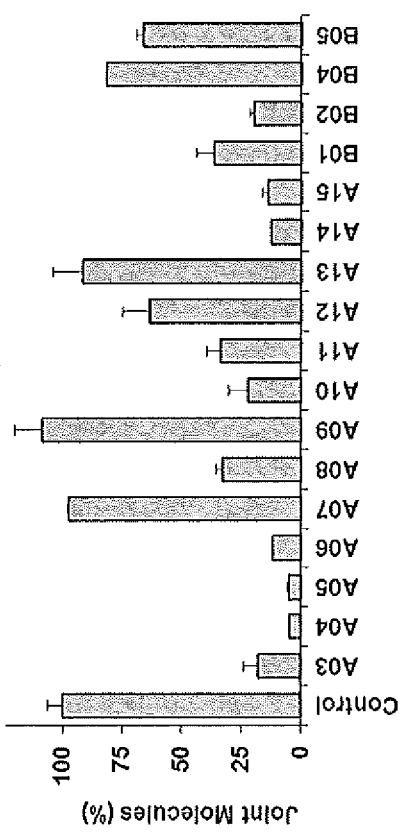
Figure 4:
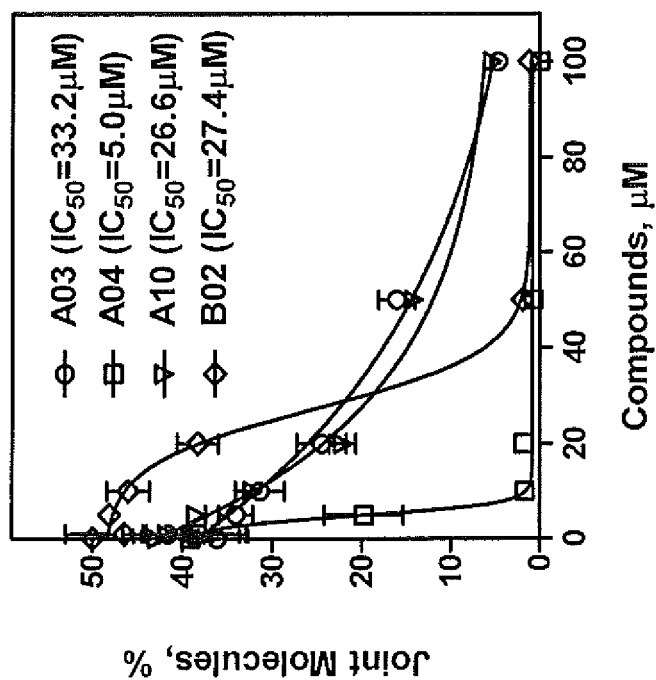
FIG. 4 is a graph illustrating the IC$_{50}$ of RAD51 inhibition by four selected compounds determined in the D-loop assay. RAD51 (1 μM) was incubated with a 90-mer ssDNA (3 μM) (SEQ ID NO:6) to form the filament followed by addition of Compounds A03, A04, A10, and B02 in indicated concentrations. After a 30-min incubation, D-loop formation was initiated by addition of pUC19 supercoiled dsDNA (50 μM). The DNA products were analyzed by electrophoresis in a 1% agarose gel. Experiments were repeated at least three times; error bars represent standard deviation.

To validate the hits identified in the primary FRET-based assay, the seventeen selected compounds (FIG. 2) were further analyzed using the D-loop assay. In the D-loop assay, DNA strand exchange was promoted by RAD51 between homologous $^{32}$P-labeled ssDNA and pUC19 supercoiled plasmid DNA (FIG. 3A). The products of this reaction, joint molecules, also known as D-loops (called after the displaced DNA strand that is formed in joint molecules during DNA strand exchange), were identified by electrophoresis in a 1% agarose gel. First, the inhibitory effect of each of the seventeen compounds on the efficiency of D-loop formation was measured. Eleven of the seventeen compounds inhibited D-loop formation by more than 50% (FIGS. 3B and 3C, Table 1). Thus, 65% of the compounds identified in the primary assay were validated by the secondary assay. In addition, using a fluorescence intercalator (ethidium bromide) displacement assay, Compounds A05, A06, A14, and A15 were found to be DNA binders (data not shown). These compounds along with Compounds A08, A11, and B01, which showed relatively modest inhibition, were not analyzed further. Then, the $IC_{50}$ values for the four most potent remaining inhibitors of the RAD51 DNA strand exchange activity were determined using the D-loop assay. The $IC_{50}$ for Compounds A03, A04, A10, and B02 were 33.2 μM, 5.0 μM, 26.6 μM, and 27.4 μM, respectively (FIG. 4; Table 2).

TABLE 1

Effect of selected compounds (100 μM) on the D-loop formation promoted by RAD51

| Compounds | Joint Molecules (%) | DNA binding[a] |
|---|---|---|
| Control | 30.3 ± 1.9 | |
| A03 | 5.4 ± 1.9 | |
| A04 | 1.4 ± 0.1 | |
| A05 | 1.6 ± 0.2 | + |
| A06 | 3.5 ± 0.1 | + |
| A07 | 29.6 ± 0.1 | |
| A08 | 10.0 ± 0.8 | |
| A09 | 32.9 ± 3.5 | |
| A10 | 6.7 ± 2.5 | |
| A11 | 10.2 ± 1.7 | |
| A12 | 19.2 ± 3.4 | |
| A13 | 27.8 ± 3.8 | + |
| A14 | 3.8 ± 0.1 | + |

TABLE 1-continued

Effect of selected compounds (100 μM) on the D-loop formation promoted by RAD51

| Compounds | Joint Molecules (%) | DNA binding[a] |
|---|---|---|
| A15 | 4.2 ± 0.7 | + |
| B01 | 11.0 ± 2.3 | |
| B02 | 6.0 ± 0.5 | |
| B04 | 24.8 ± 0.1 | |
| B05 | 20.1 ± 0.8 | |

[a]DNA binding was determined by the fluorescent interculator (ethidium bromide) displacement assay.

TABLE 2

$IC_{50}$ values for selected RAD51 inhibitors

| Compound | $IC_{50}$(RAD51) (μM) | $IC_{50}$(RecA) (μM) | $IC_{50}$(RecA)/ $IC_{50}$(RAD51) |
|---|---|---|---|
| A03 | 33.2 | 187.3 | 5.6 |
| A04 | 5.0 | 5.7 | 1.1 |
| A10 | 26.6 | 35.3 | 1.3 |
| B02 | 27.4 | >250 | n/a |
| C3a | 15.3 | >100 | n/a |
| C3b | 27.3 | >100 | n/a |

Example 4

Figure 3D:
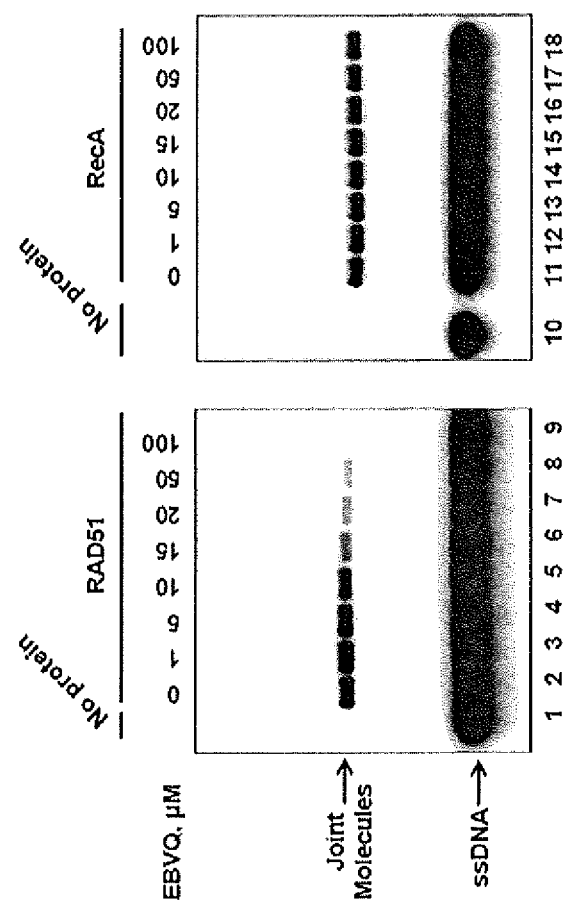
Figure 3E:
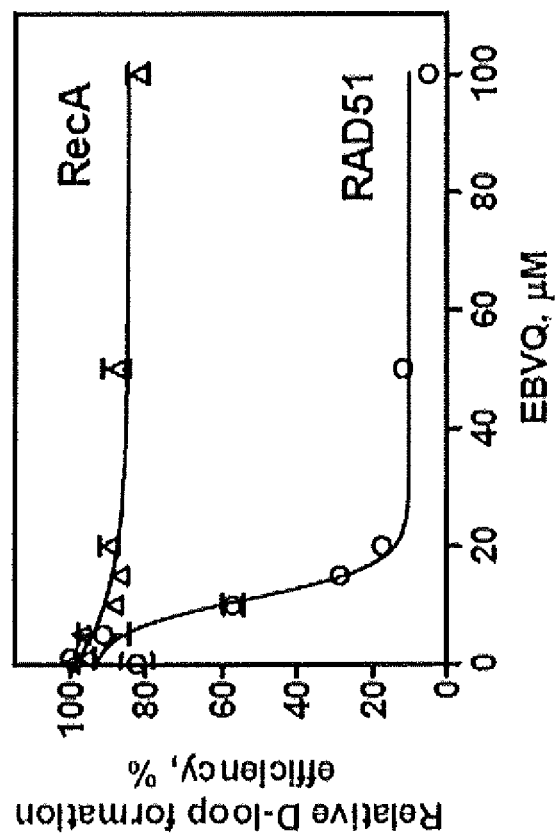

Analysis of a RAD51 Inhibitor Using the Homologous Pairing and Three Strand Exchange Assay The effect of Compound B02 on homologous pairing activity of RAD51 by D-loop assay was analyzed. RAD51 can promote homologous searching and pairing of ssDNA on supercoiled plasmid dsDNA, which contains homologous sequences of ssDNA (FIG. 3A). In this assay, $^{32}$P-labeled ssDNA (SEQ ID NO:6, 90 mer) (0.9 μM, nt) and supercoiled dsDNA (pUC19, 15 μM) was employed as DNA substrates. Compound B02 was found to efficiently inhibit the strand exchange promoted by RAD51 with a concentration-dependent manner (FIG. 3D, lane 1-9). And also interestingly, the Compound B02 did not inhibit D-loop formation of RecA protein, the prokaryotic homolog of RAD51 (FIG. 3D, lane 10-18). $IC_{50}$ for RAD51 is 10.4 μM; while for RecA protein is more than 100 μM (FIG. 3E), which indicates that Compound B02 is a very specific inhibitor for RAD51.

Figure 10A:
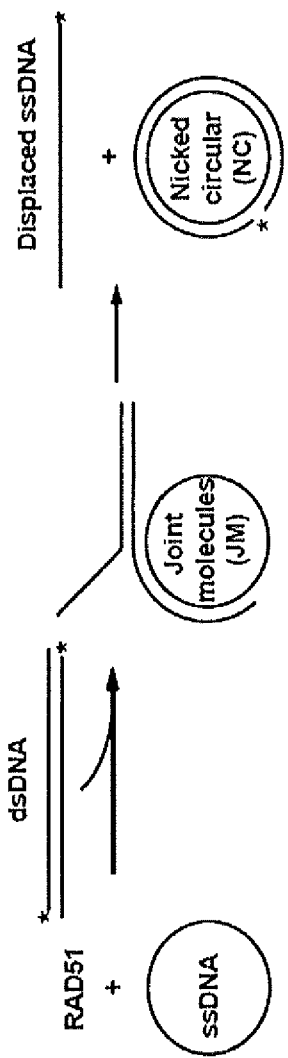

A strong inhibition of Compound B02 on RAD51 was also observed in three strand exchange assay, in which a strand exchange between circular ϕX174 ssDNA and homologous linearized ϕX174 dsDNA (linearized by ApaL1 endonuclease) was promoted by RAD51 (FIG. 10A). Yields of joint molecules (JM) and nicked circular DNA (NC) were compared among the different doses of treatment with Compound B02 (FIG. 10B). The results show that formation of both joint molecules and nicked circular DNA decreased with an increasing of Compound B02 concentration. $IC_{50}$ for the whole product (JM+NC) was 26.03 μM, which was comparable with the value observed in D-Loop assay if 1 μM RAD51 was used (data was not shown). $IC_{50}$ for the JM was 23.3 μM and for NC was 26.7 μM, suggesting that the Compound B02 has the same inhibition to JM and NC formation.

Example 5

Specificity of RAD51 Inhibitors

RAD51 shares structural and functional similarity with RecA from *E. coli*; both proteins promote DNA strand exchange in vitro and share 30% homology. Using the D-loop assay, the effect of the selected RAD51 inhibitors on the DNA strand exchange activity of RecA was evaluated. Compound A03 showed some moderate specificity for RAD51 (FIG. 5A), with the $IC_{50}$ 5,6-fold lower for RAD51 than for RecA (Table 2). Compounds A04 and A10 inhibited RAD51 and RecA with a neatly equal efficiency (FIGS. 5B & 5C; Table 2). Finally, Compound B02 showed the highest specificity for RAD51 (FIG. 5D); the $IC_{50}$ for RAD51 was 27.4 µM, whereas for RecA no significant inhibition of DNA strand exchange was observed up to 250 µM of Compound B02 (Table 2).

Figure 6B:
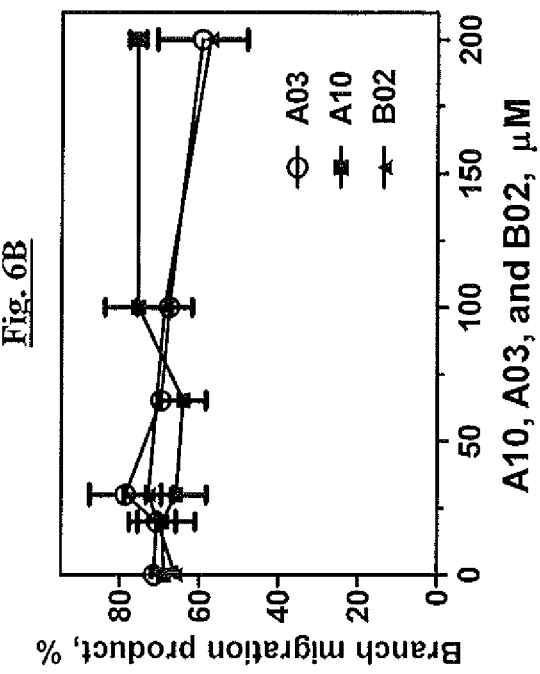
FIGS. 6A-6C, illustrates the effect of Compounds A03, A04, A10 and B02 on branch migration activity of RAD54.
Figure 6C:
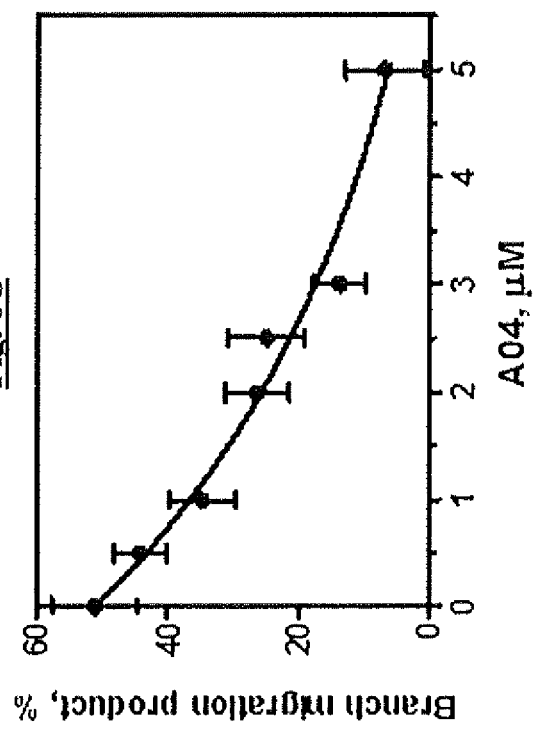
Figure 6A:
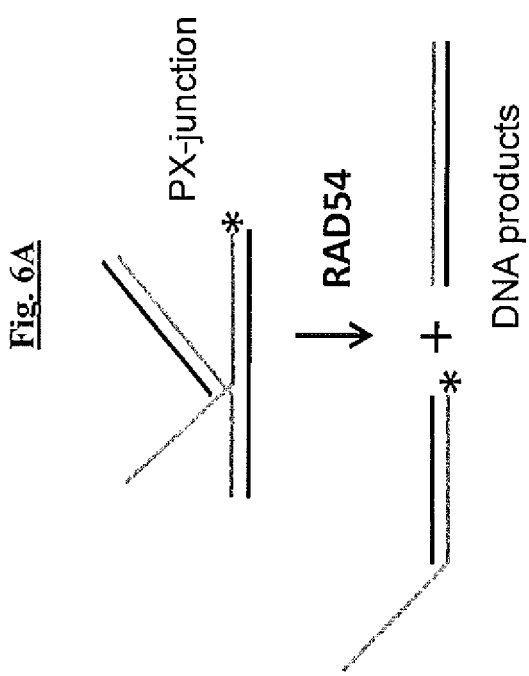

The inhibitory effects of Compound A03, A04, and A10 compounds were evaluated to determine whether they are specific for the proteins of the Rad51/RecA family or have a broader specificity. To address this question the effect of the inhibitors on human RAD54, a Swi2 protein, which does not share structural homology with the proteins of the RecA/RAD51 family, were tested (Mazin et al., 2010, DNA Repair (Arnst) 9:286-302). RAD54 promotes branch migration of Holliday junctions, a process in which one DNA strand is progressively exchanged for another (FIG. 6A). The effect of Compounds A03, A04, and A10 compounds on the RAD54 branch migration activity was tested using a $^{32}$P-labeled oligonucleotide-based cruciform DNA substrate, known as the partial Holliday junction or PX-junction (FIG. 6A). Of the four compounds tested, Compounds A03, A10 and B02 were shown not to significantly inhibit RAD54 in the range of concentrations from 0 to 200 µM (FIG. 6B). However, Compound A04 did have an inhibitory effect on the RAD54 branch migration activity ($IC_{50}$=2.6 µM) (FIG. 6C).

Thus among tested compounds, Compound B02 was identified as a specific inhibitor of human RAD51. Compounds A03 and A10 inhibited both RAD51/RecA family proteins, RAD51 and RecA. Compound A04 showed the broadest inhibitory spectrum by inhibiting all three tested proteins: RAD51, RecA and RAD54.

Example 6

Blockage of the RAD51-ssDNA Filament Formation at the Presynaptic Stage

To explore the mechanism how Compound B02 inhibits the homologous pair and strand exchange, three experiments were carried out.

Figure 11C:
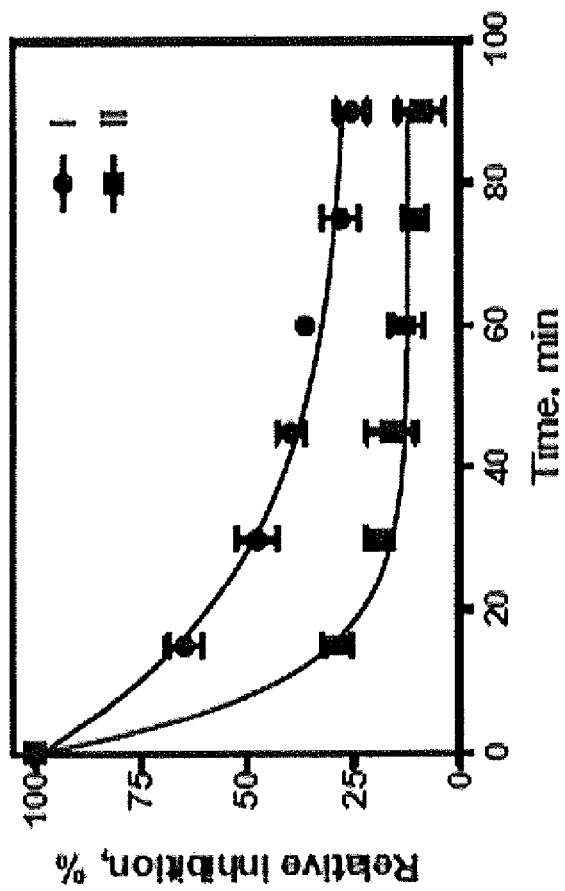

Firstly, the time course of D-loop formation was compared with different order of addition of Compound B02 and ssDNA (FIG. 11A). In Protocol (I), 20 µM Compound B02 was added after the filament formation; and then the samples were incubated for indicated times before the initiation of D-loop formation by addition of dsDNA. In Protocol (II), RAD51 was first incubated with 20 µM Compound B02 for indicated time; and then ssDNA was added and incubated for 15 min at 37° C. to form the filament before the initiation of D-loop formation by addition of dsDNA. The results show that, in both Protocols (I) and (II), the efficiency of D-loop formation decreased in the presence of Compound B02 (FIG. 11B, lane 1-7 and 8-14), while the efficiency of D-loop formation increased or keep stable in the absence of Compound B02 (data not shown). Furthermore, the relative inhibition (FIG. 11C), which was expressed as the ratio of the joint molecules with Compound B02 treatment to those without Compound B02 treatment, shown that in the presence of Compound B02 the efficiency of D-loop formation in Protocol II (FIG. 11B, lane 8-14) reduced much faster than that in Protocol I (FIG. 11B, lane 1-7).

The results suggest the Compound B02 can either block the assembly of the filaments if added before filament formation or disrupt the assembled filaments if added after the filament formation. However, a lower portion of filaments was disrupted if Compound B02 was added after the filament formation, owing to the high stability of nucleoprotein filaments.

Figure 12A:
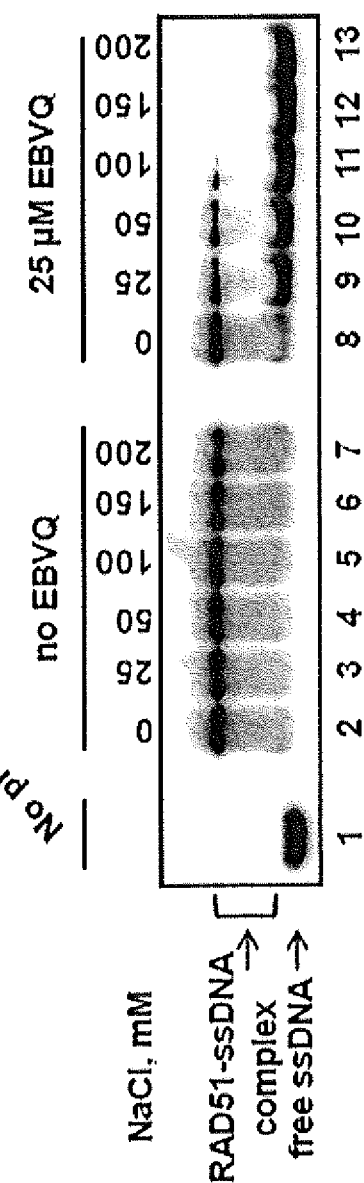
FIG. 12A-12B, illustrates the finding that Compound B02 inhibits ssDNA binding of RAD51.
Figure 12B:
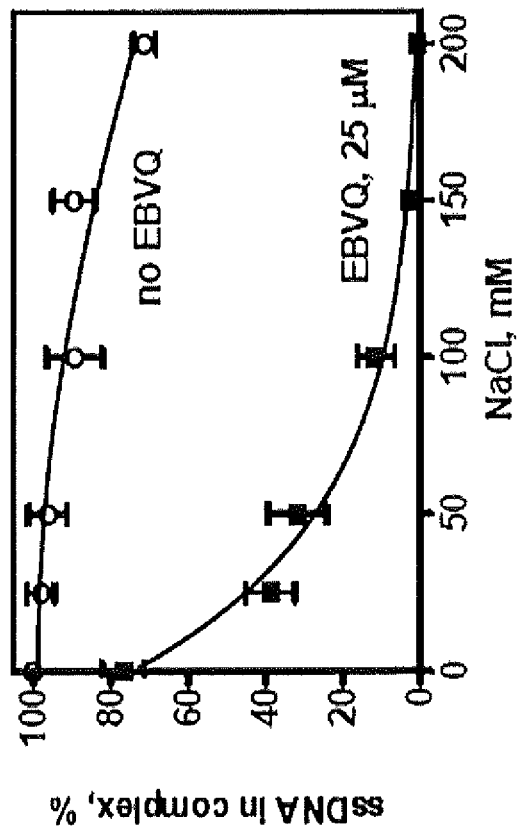

Secondly, the effect of Compound B02 on assembly of RAD51-ssDNA filaments was tested using ssDNA binding assay. In this assay, RAD51 (1 µM) was incubated with 25 µM Compound B02, which was comparable with $IC_{50}$ obtained from D-loop assay if 1 µM RAD51 was used (data was not shown). Then ssDNA (SEQ ID NO:6, 90 mer) (3 µM, nt) was added in the presence of indicated concentration of NaCl. The binding of ssDNA of RAD51 protein was impaired with the challenge of increasing concentration of NaCl. If Compound B02 could disrupt the RAD51-ssDNA filaments, more $^{32}$P-labeled free ssDNA dissociating from the filaments would be observed. The results (FIG. 12) show that without Compound B02, the ratio of ssDNA in complex decreased from 100% (0 mM NaCl) to 71% (200 mM NaCl), only 29% loss of filaments; while with Compounds B02, the ratio of ssDNA decreased from 80% (0 mM NaCl) down to almost 0% (200 mM NaCl), which means all the filaments were disrupted in the presence of 200 mM NaCl. Besides, even without NaCl challenge, there was still 20% loss of filaments in the presence of Compound B02. These results suggest that Compound B02 can disrupt the RAD51-ssDNA filaments.

Figure 13:
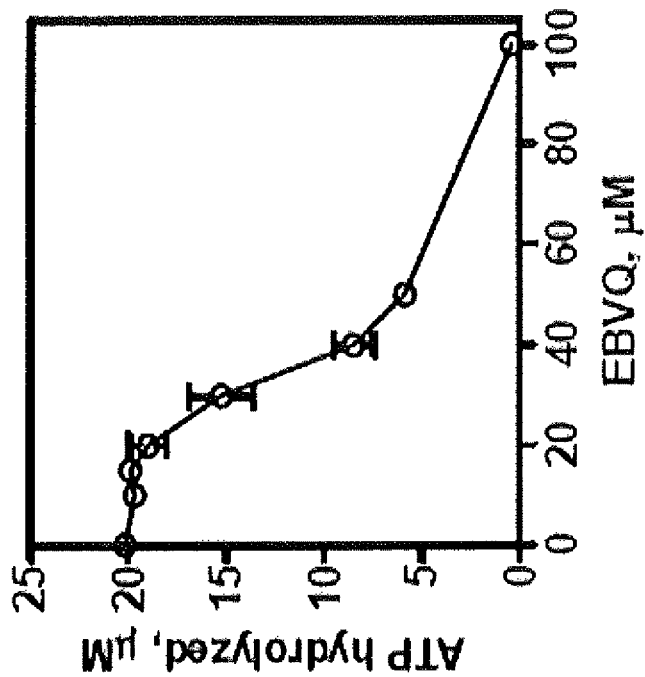
FIG. 13 is a graph illustrating inhibition of the DNA-dependent ATPase activity of RAD51 by Compound B02 in a concentration-dependent manner. RAD51 (1 µM) was incubated with Compound B02 in indicated concentration for 30 min in buffer containing 25 mM Tris-acetate (pH 7.5), 1 mM DTT, 100 µg/ml bovine serum albumin (BSA), 2 mM Mg(OAc)$_2$, 0.1 mM ATP and 10 µCi[γ-$^{32}$P]ATP(6000 Ci/mmole), then ssDNA (3 µM) (SEQ ID NO:6, 90 mer) was added to initiate ATP hydrolysis. After 1.5 h incubation, the samples were analyzed by PEI-TLC. Experiments were repeated at least three times; error bars represent standard error of the mean.

Thirdly, the effect of Compound B02 on the ATPase activity of RAD51 was tested by concentration titration of Compound B02. As illustrated in FIG. 13, Compound B02 can inhibit the ATPase activity of RAD51 with a concentration-dependent manner, and $IC_{50}$ is 37.6 µM. The DNA-dependent ATPase activity of RAD51 is correlative with the binding of DNA on the protein. Therefore, the inhibition of Compound B02 on ATPase activity of RAD51 also suggests that Compound B02 can disrupt the RAD51-ssDNA filaments.

Example 7

Disruption of the Binding of dsDNA on RAD51-ssDNA Filament

In the RAD51 protein, there are two specific DNA-binding sites: the primary DNA binding site and the secondary binding site (Sung et al., 2003, J. Biol. Chem. 278:42729-32). In the presynaptic stage of strand exchange, the RAD51-ssDNA filament was assembled by binding of ssDNA into primary binding site of RAD51. The search of DNA homology was done by reiterative binding and release of duplex DNA on and from the secondary binding site of RAD51 in RAD51-ssDNA filaments until the homology was located. So the secondary binding site is also indispensable for the strand exchange. DNA coaggregation assay was used to test the effect of Compound B02 on binding of duplex DNA on the secondary hinding site of RAD51.

Figure 14A:
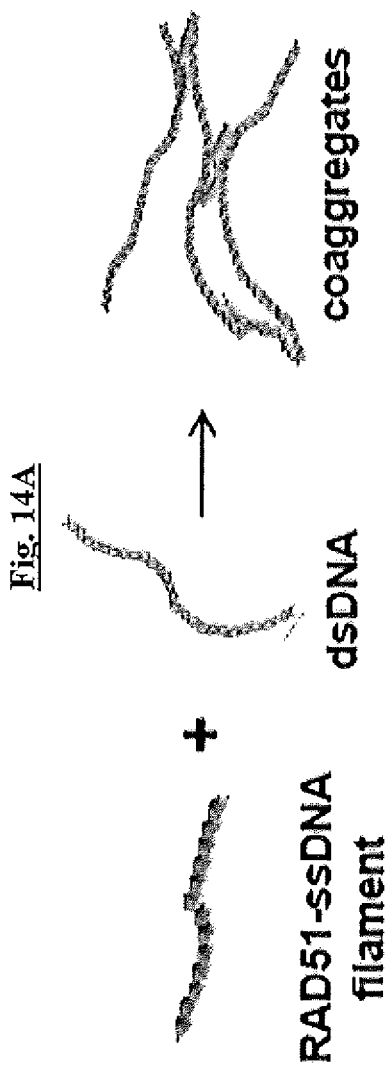
FIGS. 14A-14B, illustrate the inhibition by Compound B02 of the coaggregation of dsDNA with the RAD51-ssDNA filament.
Figure 14B:
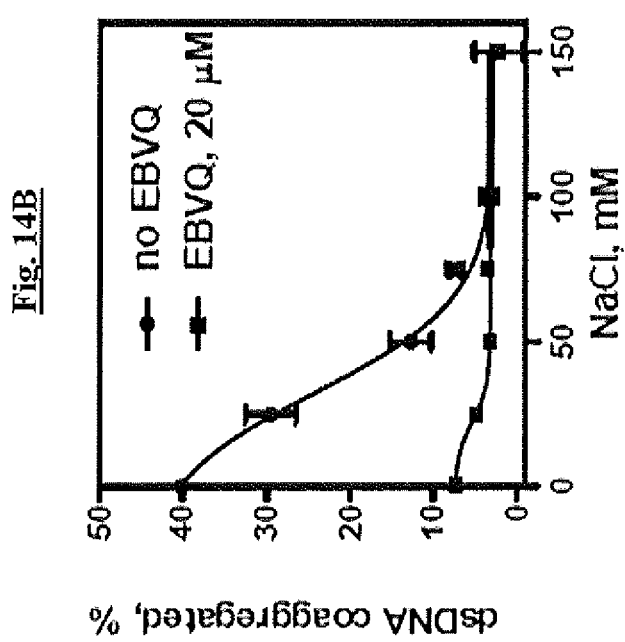

In this assay, the RAD51-ssDNA filament was assembled by incubation of 1 µM RAD51 with 3 µM ssDNA (SEQ ID NO:7, 94 mer). RAD51 primary binding site was saturated by ssDNA at this DNA concentration. Then the filament was mixed with 25 µM dsDNA (pUC19, linearized by BamHI) and challenged by NaCl in the absence or presence of 20 µM Compound B02. If Compound B02 can disrupt the binding of dsDNA on secondary binding site of RAD51, the DNA coaggregations will be more unstable in Compound B02 presence samples than in Compound B02 absence samples, and the percent of dsDNA in coaggregations (FIG. 14) will be lower in Compound B02 presence samples than in Compound B02 absence samples. As expected, much lower percent dsDNA in coaggregations was observed in Compound B02 presence samples. Even without the challenge of NaCl, the ratio of dsDNA coaggregations in Compound B02 presence samples was only 8%, which is ⅕ of that in Compound B02 absence samples. These results suggest that Compound B02 can disrupt not only the binding of ssDNA on primary binding site of RAD51 but also the binding of dsDNA on secondary site of RAD51, both of which are critical to the homologous recombination.

Example 8

Inhibition of HDR of a Chromosomal DSB

Figure 8A:
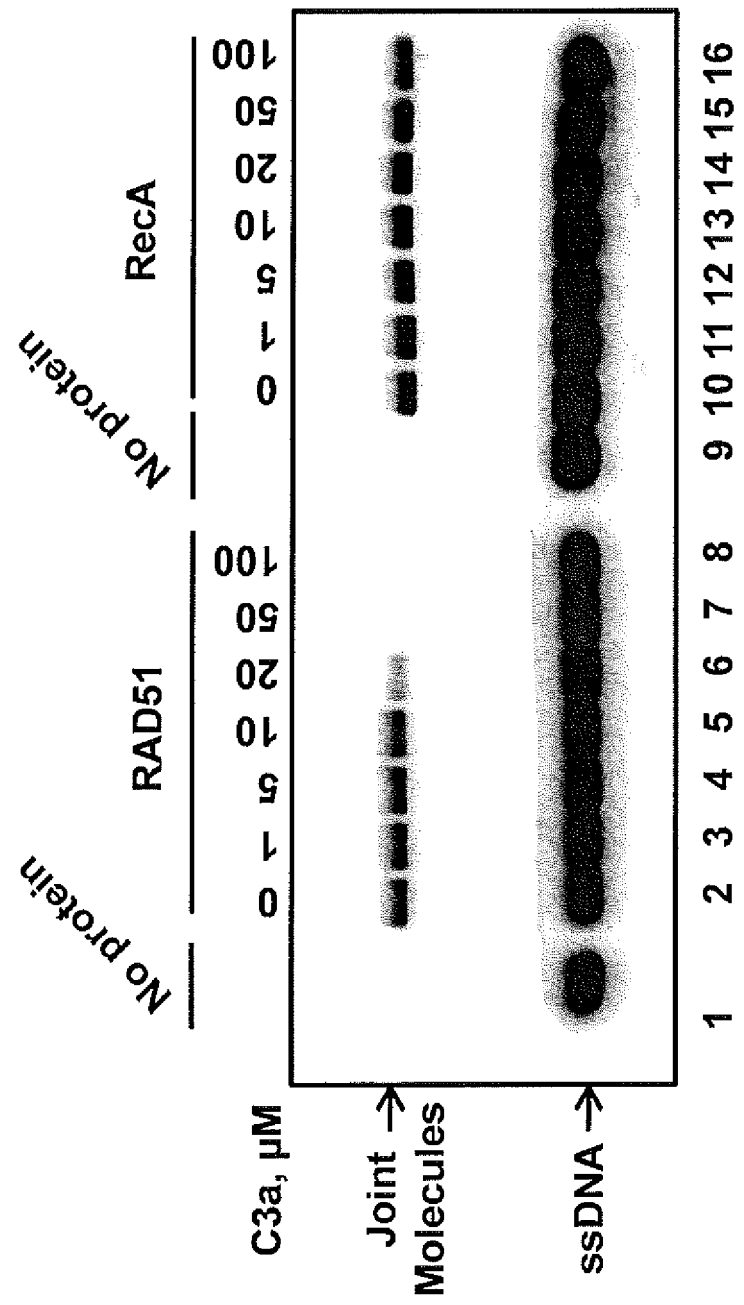
FIGS. 8A-8C, illustrates the effect of Compounds C3a and C3b on DNA strand exchange activity of RAD51 and RecA.
Figure 15A:
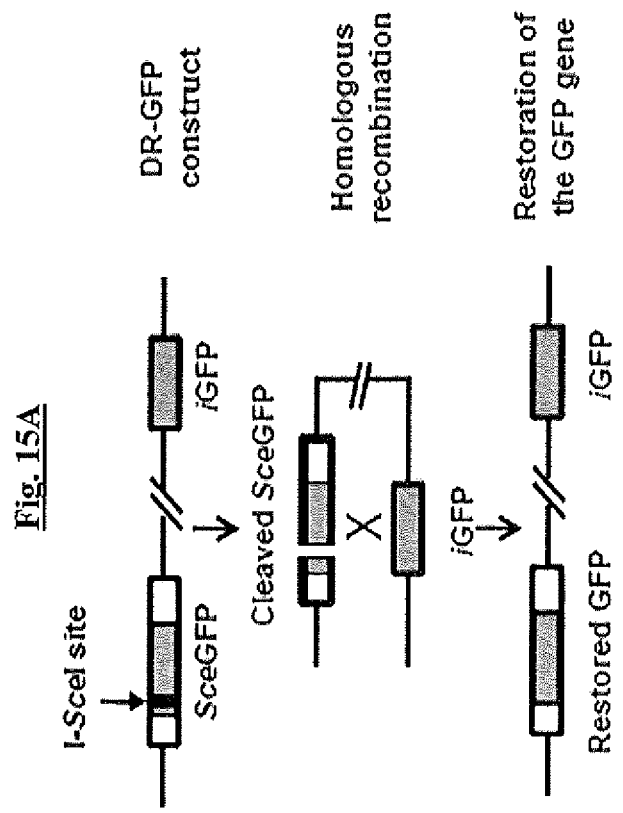
FIGS. 15A-15C, illustrates the finding that Compound B02 inhibits. DSB-induced homologous recombination in human cells.
Figure 15B:
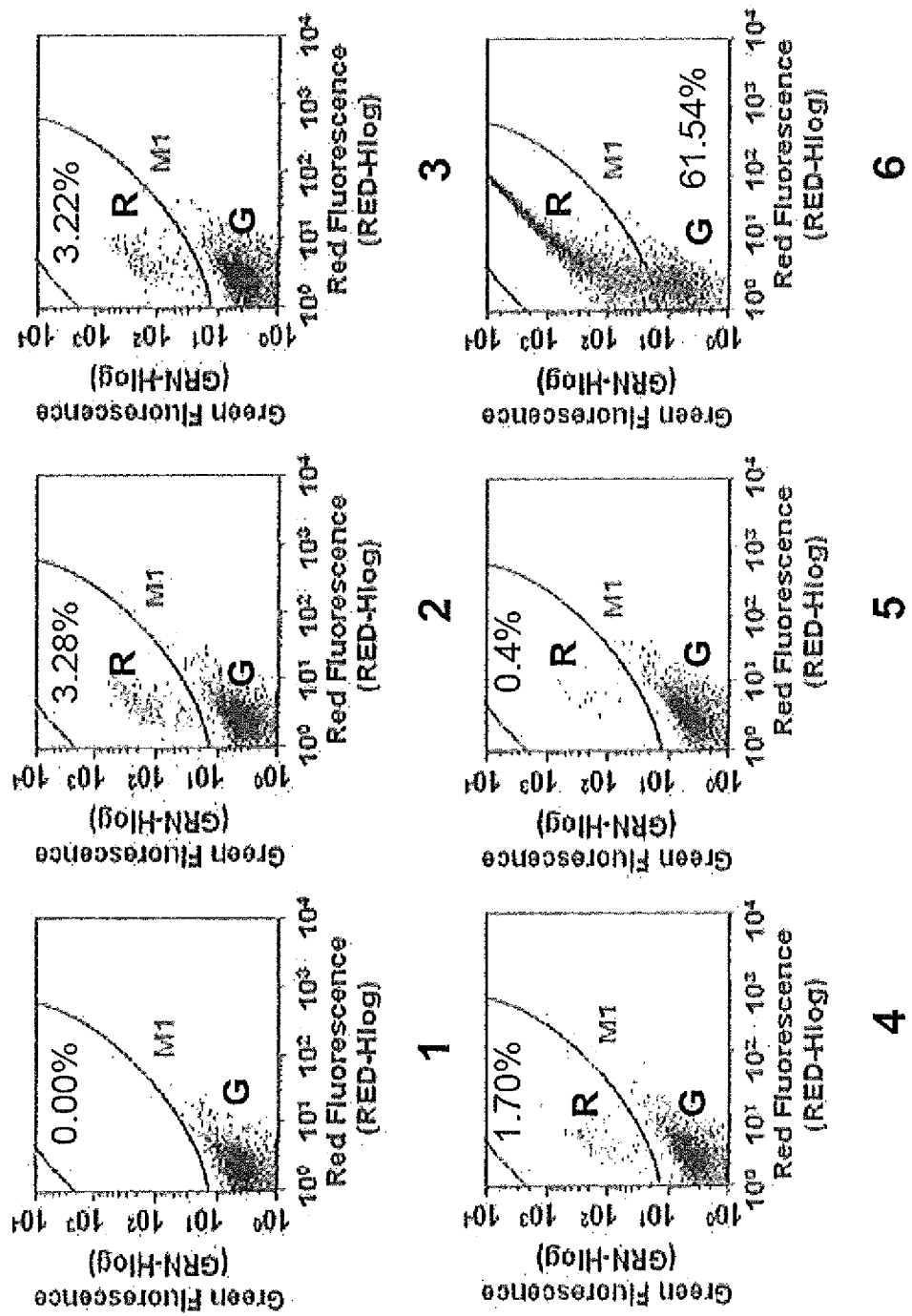
Figure 16A:
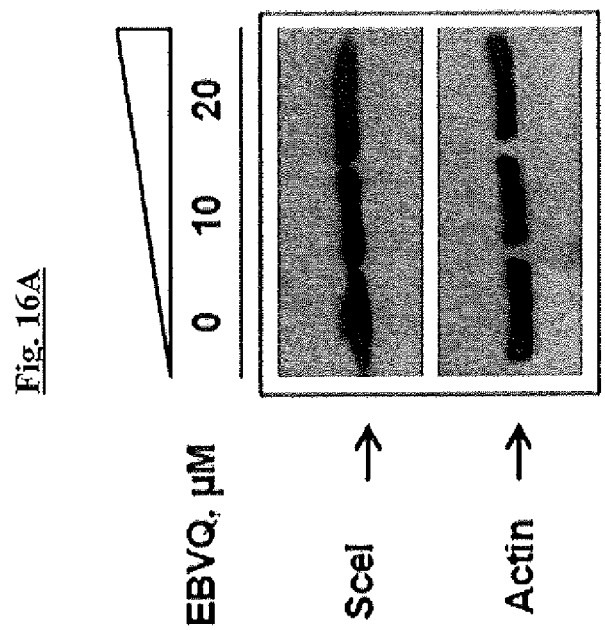
Figure 15C:
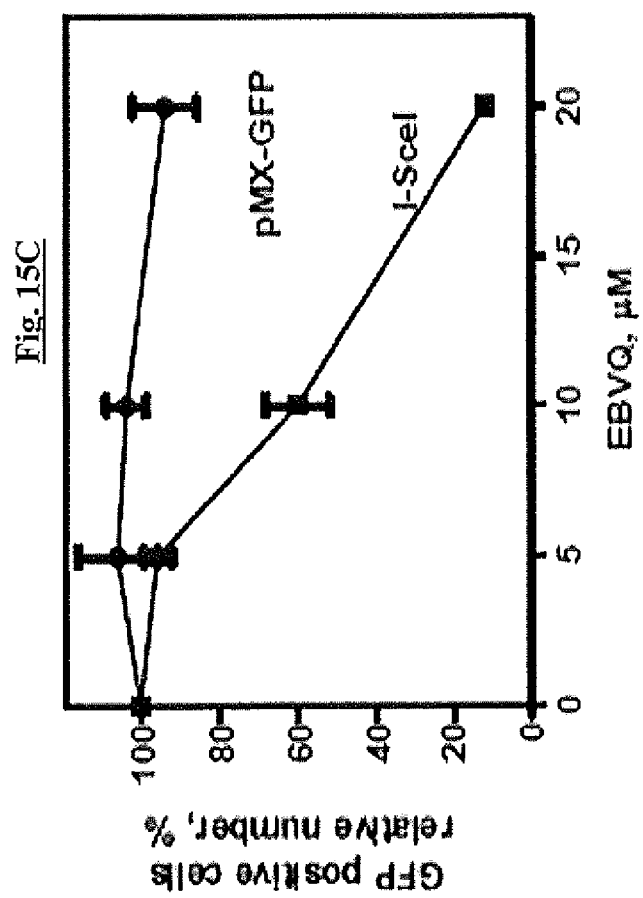

DR-GFP assay can be used to monitor HDR of chromosomal DSB by fusion a DR-GFP report gene construct in chromosome of cells. In DR-GFP construct (FIG. 15A), SceGFP gene, which encodes green fluorescent protein (GFP), was disabled by insertion of an 18-bp recognition site for I-SceI cleavage into SceGFP gene. A DSB can be generated by expressing of the transfected pCBASec plasmid, which encodes I-SceI endonuclease. Repair of the I-SceI induced DSB by recruitment of IGFP (an internal GFP gene fragment truncated at both ends) as a template (FIG. 8A) gives rise to a functional GFP gene. This HDR event can be scored by green fluorescence in individual cells, using flow cytometric analysis. Consequently the effect of Compound B02 on the HDR of a chromosome in cells can be clearly addressed. The pCBASec plasmid was transfected in DR-GFP 293 cells in the presence of 0 μM, 5 μM, 10 μM and 20 μM of Compound B02. To validate the gene transfection, the cells transfected with pMX-GFP, which encodes functional GFP protein, were used as a positive control. And notransfected parental cells were used as a negative control. Compound B02 can reduce the yield of GFP positive cells by a concentration-dependent manner. As shown in FIG. 15B, the yield of GFP positive cells decreased from 3.28% in non-treatment cells to 0.40% in the cells treated with 20 μM of Compound B02, an 8-fold reduction was observed, suggesting that as a RAD51 inhibitor, Compound B02 can efficiently disrupt the HDR promoted by RAD51. But this claim can be easily invalidated by two possibilities: (1) Compound B02 inhibits the transfection or expression of pCBASce, which just produces less DSB than that in the absence of Compound B02, and consequently less DSB repair will produce lower level of GFP positive cells; (2) Compound B02 inhibits the expression RAD51 in the cells. Recently published paper has reported a Histone deacetylase (HDAC) inhibitor, which indirectly inhibited HDR by reducing the expression of RAD51 (Adimaolan et al., 2007, Proc. Natl. Acad. Sci. USA). To exclude these possibilities, first the effect of Compound B02 on the plasmid transfection was tested. The pMX-GFP plasmid, which encodes the functional GFP protein, was used as a reporter. After transfection of pMX-GFP plasmid into DR-GFP 293 cells, the expression of functional GFP protein was monitored by flow cytometric analysis. The cells transfected with pMX-GFP plasmid, but without treatment of Compound B02 were used as a control. It was observed that Compound B02 has no inhibition to transfection in comparison to control cells. The ratio of GFP positive cells is comparable between the cells in control group (31.52%) and the cells with 20 μM Compound B02 (31.47%) (FIG. 15C). Furthermore, the expression of I-SceI protein in DR-GFP 293 cells was assessed with or without treatment of Compound B02 using western blot assay. The results show that Compound B02 did not affect the expression of I-SceI protein (FIGS. 16A & 16B). Next, a western blot assay was carried out to test the effect of Compound B02 on the expression of RAD51, the data show that the expression of RAD51 was comparable between the cells without treatment of Compound B02 and cells treated with 20 μM Compound B02 (FIGS. 16C and 16D). The results of the two experiments above suggest that the reduction of yield of GFP positive cells is attributed to the inhibition of Compound B02 on RAD51 protein, which is a key protein in the HDR of Chromosomal DSB.

Example 9

Sensitivity of MEF Cells to Double-Strand Break (DSB) Induced Agents

Figure 18:
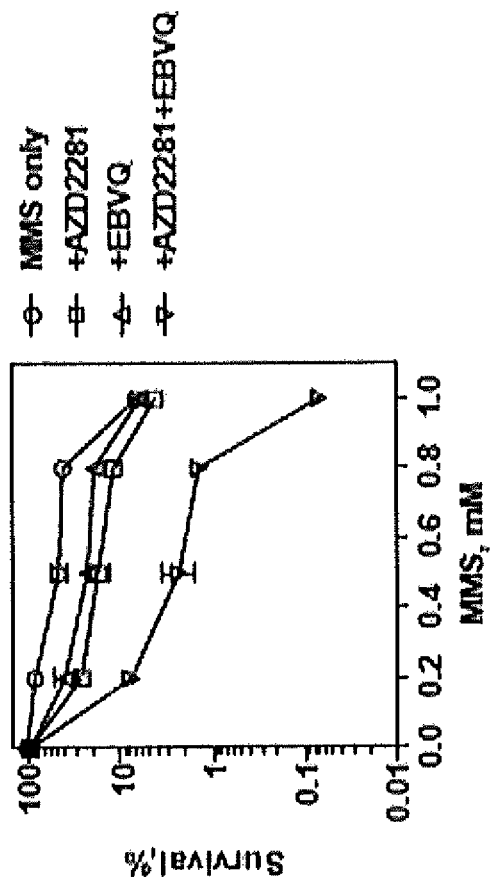
FIG. 18 is a graph illustrating the finding that cotreatment of MEF cells with a PARP-1 inhibitor AZD2281 and Compound B02 further increases cell sensitivity to DNA damaging agents. MEF cells were treated with MMS (○), and then some fractions of these cells were additionally treated with Compound B02 (5 µM) (Δ), AZD2281 (1 µM) (○), or with both Compound B02 (5 µM) and AZD2281 (1 µM) (□). Experiments were repeated at least three times; error bars represent standard deviation.
Figure 17C:
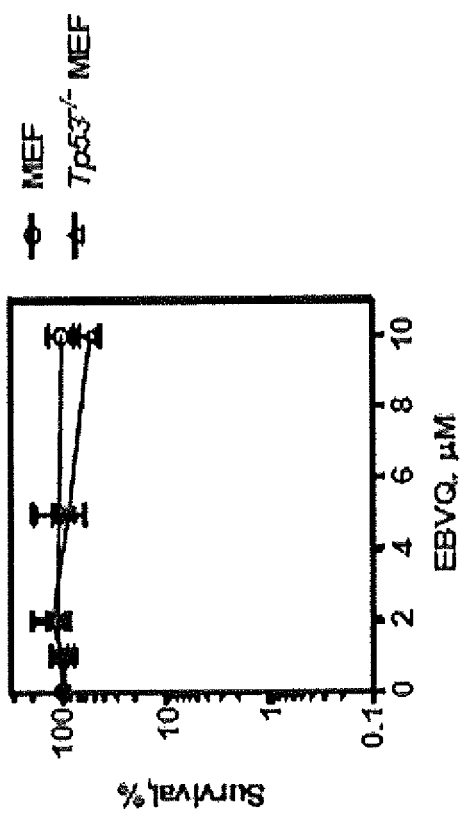

Based on the observation that Compound B02 can inhibit the homologous recombination in vitro, it is quite interesting to explore if Compound B02 has inhibition on homologous recombination in cell level. Herein the sensitivity of MEF cell lines (wide type and Tp53−/−) to the DNA cross-linking agents cisDDP and MMC in the absence and presence of Compound B02 was analyzed by using colongenic survival assay. Before this experiment, the toxicity of Compound B02 to the cell lines selected was first assessed. No decrease of cellular viability with the treatment up to 5 μM Compound B02 was observed. Therefore this concentration was selected for the colongenic survival assay. As shown in FIG. 17, in the presence of 5 μM Compound B02, both cell lines were more sensitive to the cisDDP and MMC, which suggest that Compound B02 may reduce the resistance of cells to DNA damage agents by inhibiting the DSB repair. Some SSB-induced agents such as MMS induce DNA damage. Failure to repair the SSB could produce stalled replication fork, and collapsing of the stalled replication fork could finally cause DSB. PARP-1 protein is a key protein in BER pathway, which is very important in SSB repair. Here to validate inhibition of Compound B02 to RAD51 protein in mammalian cells, the sensitivity of MEF cells to DNA damage agents MMS was tested. MEF cells were treated by MMS to induce the SSBs in the presence of 5 μM Compound B02 or 1 μM of a PARP-1 inhibitor, AZD2281 (olaparib or 4-[(3-[(4-cyclopropylcarbonyl)piperazin-4-yl]carbonyl)-4-fluorophenyl]methyl(2H) phthalazin-1-one) or both. The cells treated only with MMS were used as a control. The results show that in the presence of 1 μM AZD2281, the cells are more sensitive to MMS than that in the absence of AZD2281 (FIG. 18). The sensitivity enhancement may be attributed to that the treatment of AZD2280 inhibits the BER, which blocks the repair of the SSB induced by MMS. Additionally, if in the presence of both Compound B02 and AZD2282, the cells were more sensitive to MMS than that only in the presence of AZD2281, suggesting that not only the SSB repair was blocked, meanwhile the repair of DSB induced by the collapsing the stalled fork was also blocked, the data shows evidence that the Compound B02 inhibits the repair of DSB in the cells by inhibition of the RAD51 activity. Also the enhancement of sensitivity was observed in the cells with co-treatment of the MMS and Compound B02. This could happen because even in the non-treated cells there is certain amount of stalled fork which could collapse and induce DSH. The enhancement of sensitivity may response to the inhibition of Compound B02 to DSB repair.

Example 10

SAR Analysis of Compound B02

Figure 7A:
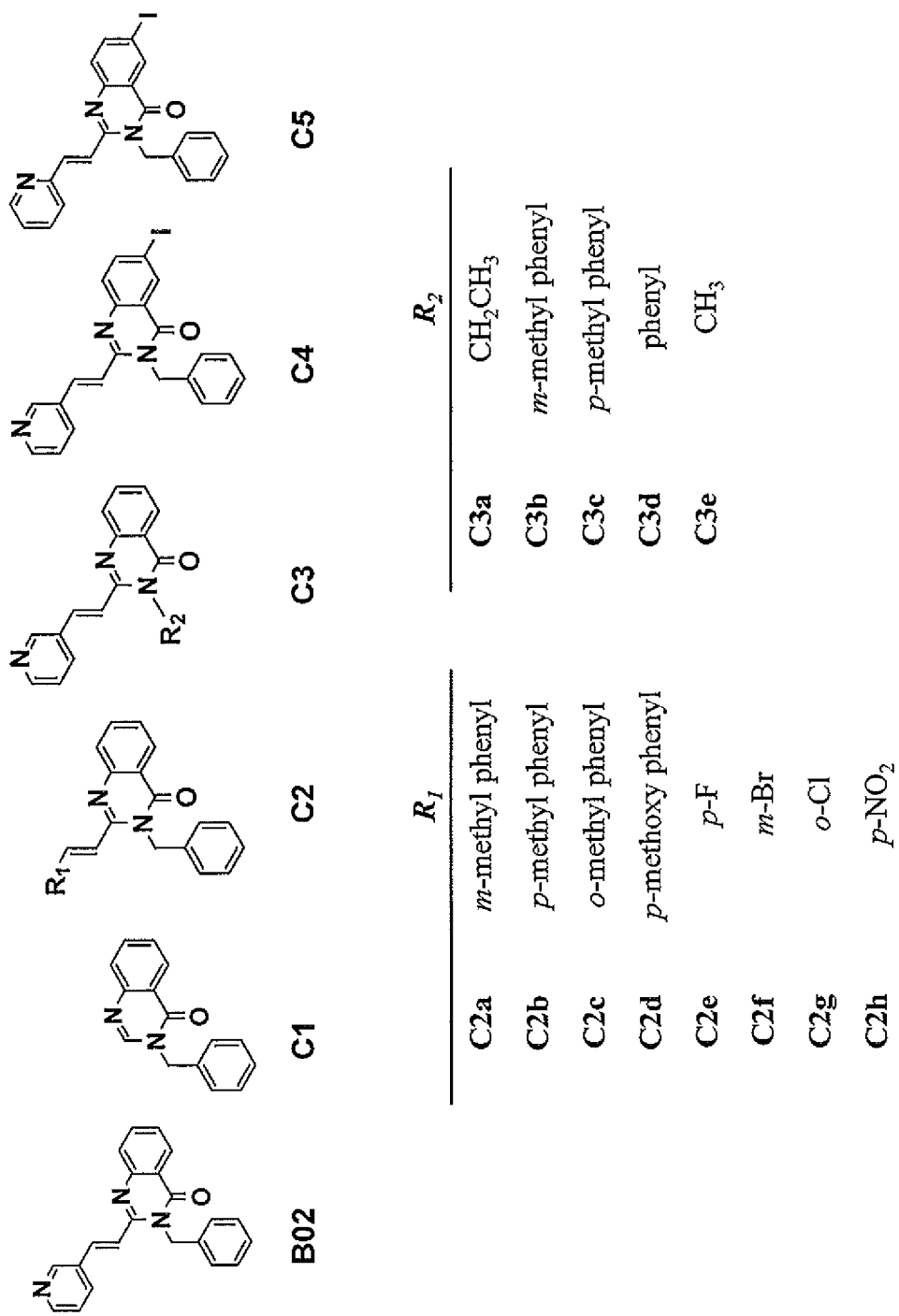
FIGS. 7A-7C, illustrates the analysis of Structure-Activity Relationship (SAR) of Compound B02.

For SAR analysis of Compound B02, a 16-compound library of B02 derivatives was selected (FIG. 7A). According to the structural features, the 16 compounds were sorted in 5 groups. In group 1 (compound C1): (E)-2-(pyridin-3-yl) vinyl was removed with (E)-2-(R$_1$-substituting group) vinyl; in group 3 (compounds C3a to C3e): benzyl was replaced by 6-iodo-quinazolin-4(3H)-one; in group 5 (compound C5): the core, quinazolin-4(3H)-one was replaced by 6-iodo-quinazolin-4(3H)-one, as well as (E)-2-(pyridin-3-yl) vinyl was replaced by (E)-2-(pyridin-2-yl) vinyl.

Figure 7B:
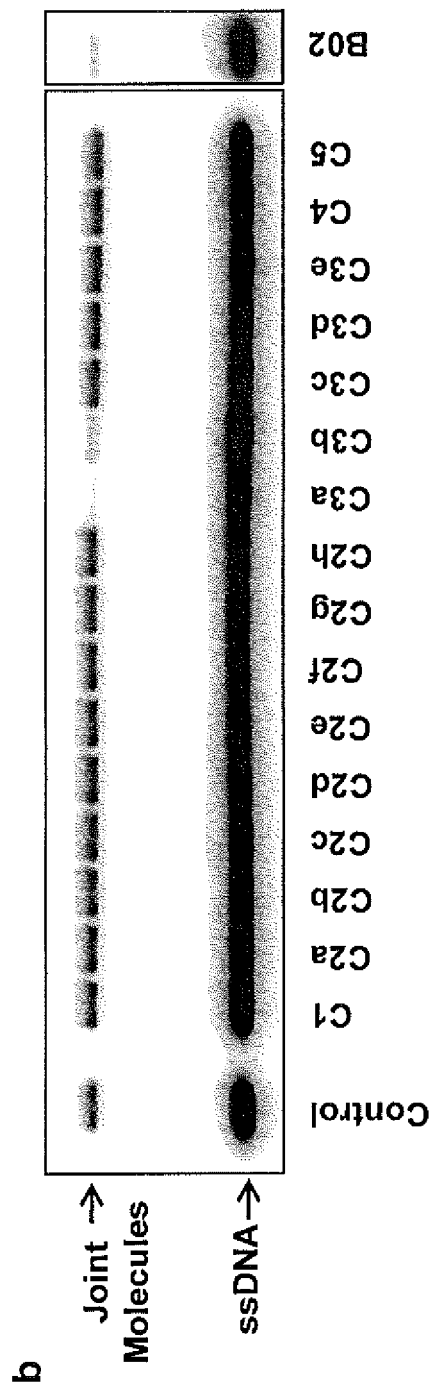
Figure 7C:
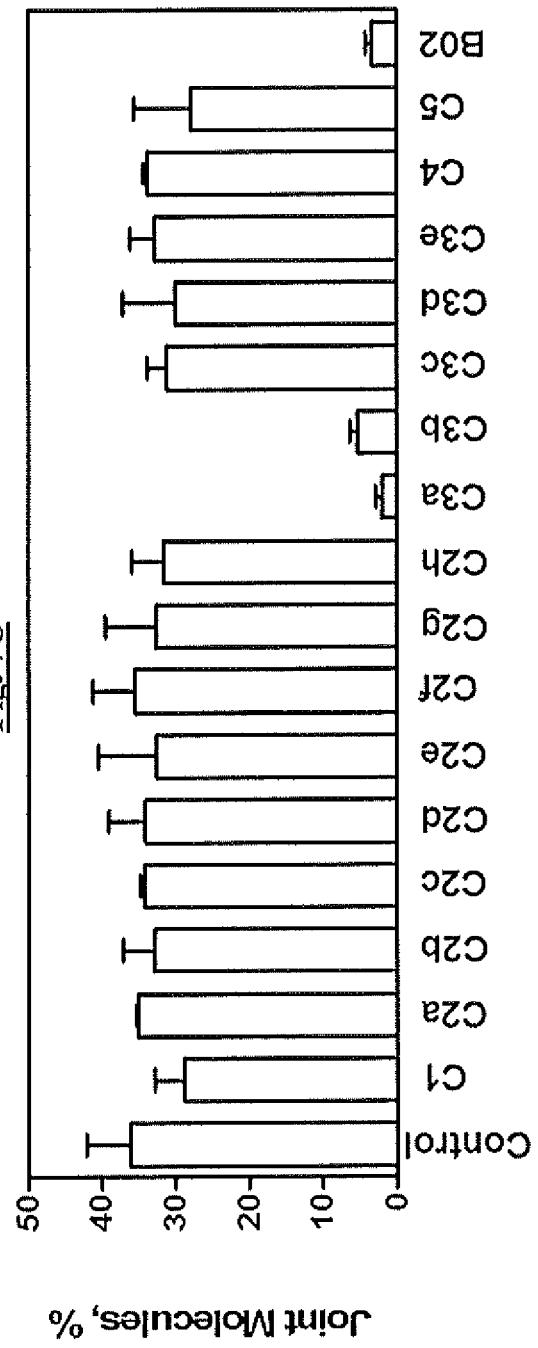

The inhibitory effect of these B02 derivatives (50 μM) on the DNA strand exchange activity of RAD51 was determined using the D-loop assay. The only position of BO2 that could tolerate modifications and still inhibit RAD51 was the benzyl (compound group 3) (FIG. 7B and 7C). Moreover, only compound C3a (R$_2$ ethyl) and compound C3b (R$_2$=m-methyl phenyl) retain the inhibitory effect, the substitutions of other groups (C3d, R$_2$=phenyl and C3e, R$_2$=methyl) or at the different positions (C3c, R$_2$=p-methyl phenyl) eliminates the inhibition, suggesting that the inhibition is tightly related to the size and the steric conformation of the substituting group. All other tested replacements in the groups 1, 2, 4, and 5 eliminated RAD51 inhibition. The high sensitivity of the RAD51 inhibition to B02 modifications suggests specific interactions between the inhibitor molecule and RAD51 protein.

Example 11

Inhibitor Optimization

Figure 8C:
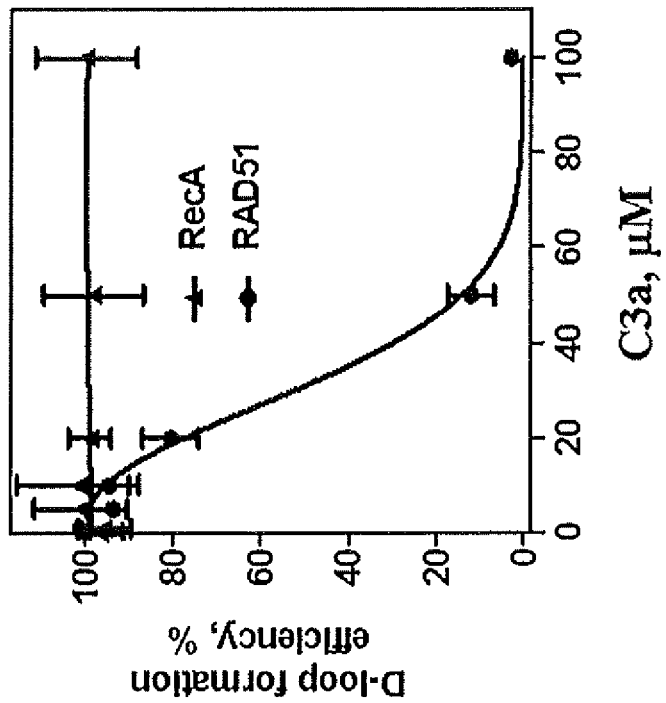
Figure 8B:
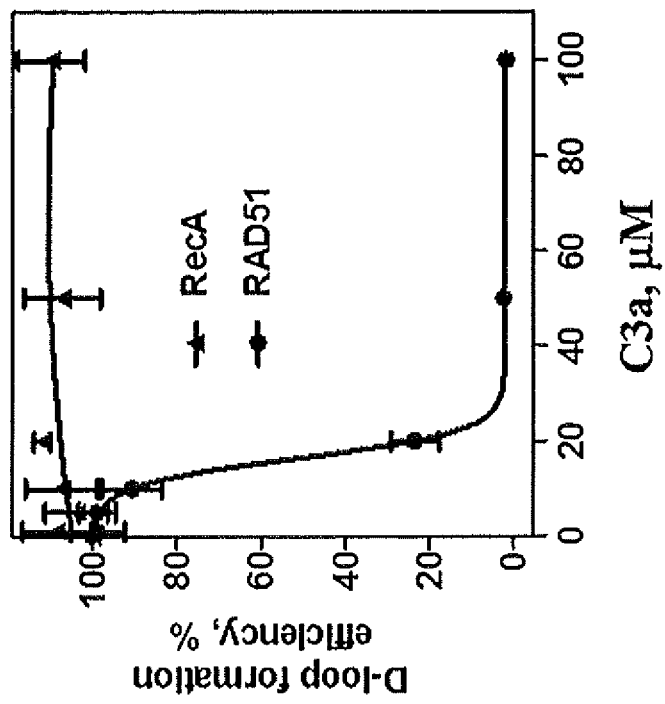
Figure 9:
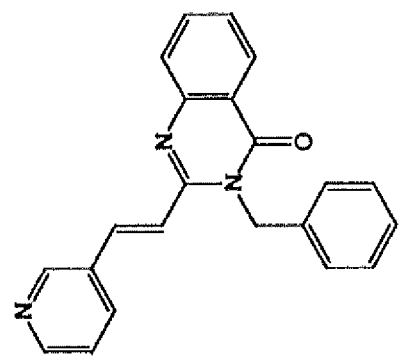
FIG. 9 is an illustration of the structure of (E)-3-benzyl-2-(2-(pyridin-3-yl) vinyl)quinazolin-4(3H)-one) (EBVQ or Compound B02).

From the library of B02 derivatives, two compounds (C3a and C3b) that inhibited RAD51 were identified (FIG. 7). For these two inhibitors, the IC$_{50}$ values of the RAD51 DNA strand exchange activity and their selectivity for RAD51 were determined using the D-loop assay (FIG. 8). The IC$_{50}$ for C3a and C3b are 15.3 μM and 27.3 μM, respectively (FIG. 8B 7 8C). To evaluate the selectivity of the inhibitors the effect of C3a and C3b on the DNA strand exchange activity of RecA were determined. The results show that compounds C3a and C3b in concentrations up to 100 μM do not inhibit RecA (FIG. 8; Table 2).

Thus, the current results demonstrate the feasibility and efficiency of the HTS approach for discovery of novel selective inhibitors of RAD51, a key protein of homologous recombination and the repair of DNA double strand breaks and interstrand crosslinks. Further experiments may include establishing the mechanism of specific RAD51 inhibition by selected small molecule compounds (B02, A03, A10) and examining the effect of these compounds on the RAD51-dependent homologous recombinations and DNA repair in human cells.

Example 12

Binding to RAD51 and Inhibition of Its Activities

Figure 19:
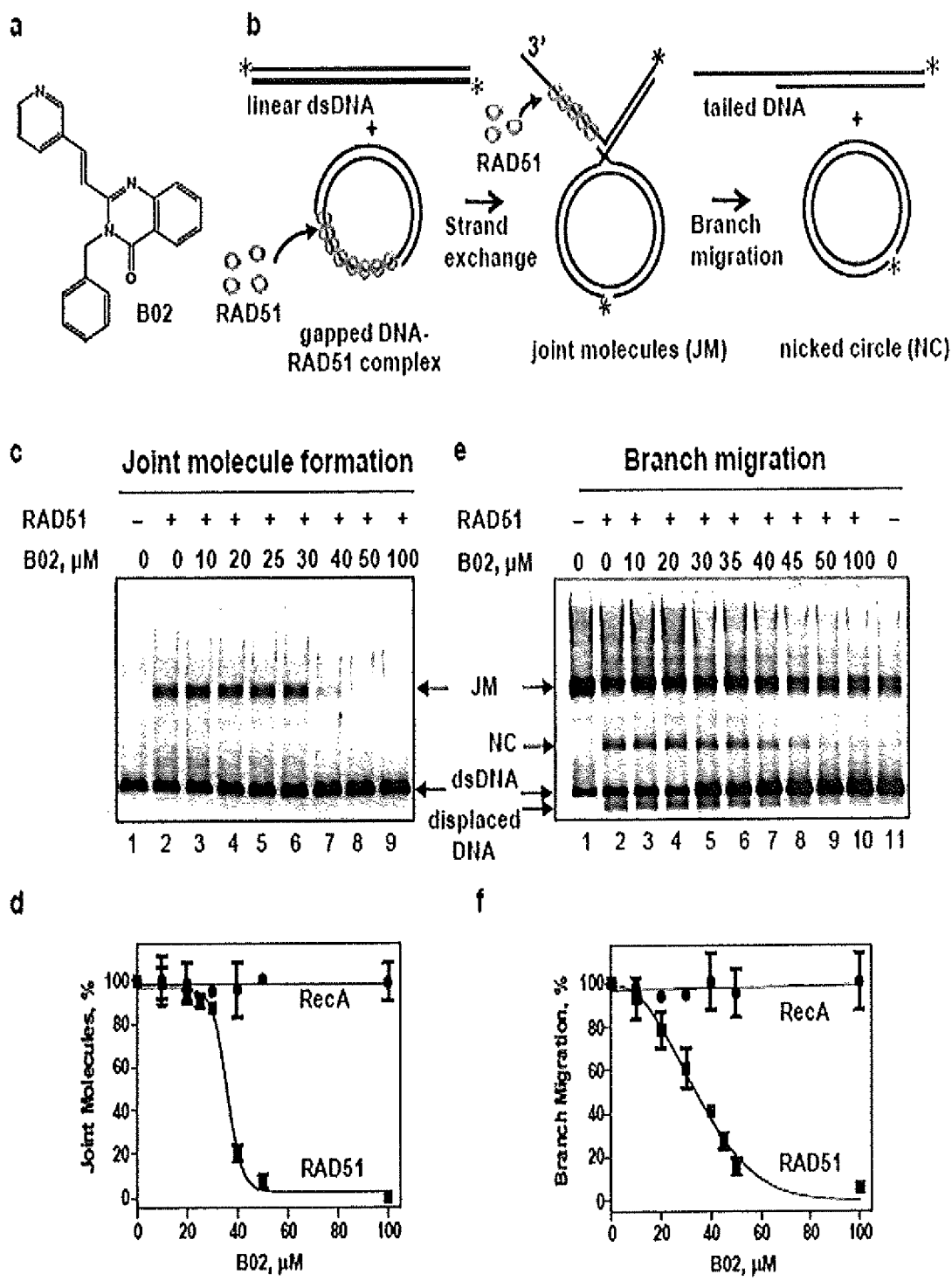
FIG. 19, comprising
Figure 20A:
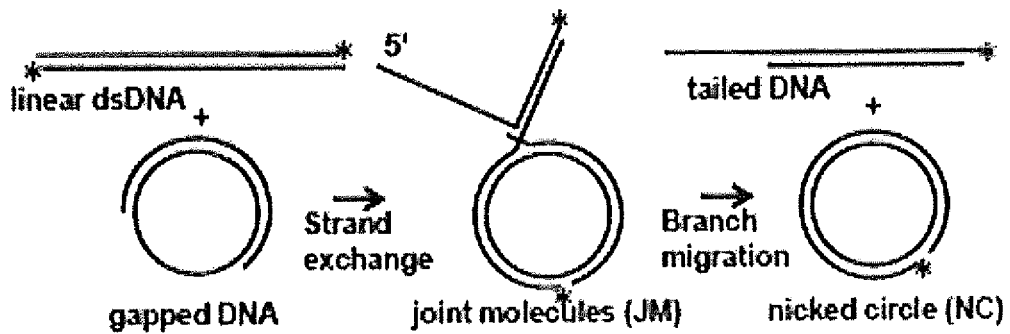
FIGS. 20A-20C, illustrates the finding that Compound B02 does not inhibit the DNA strand exchange and branch migration promoted by RecA.
Figure 20B:
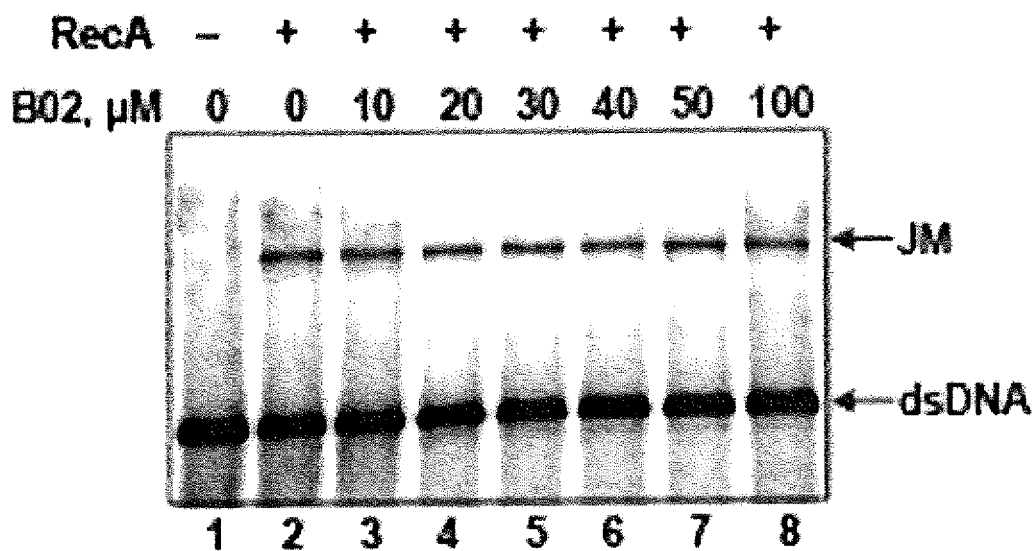
Figure 20C:
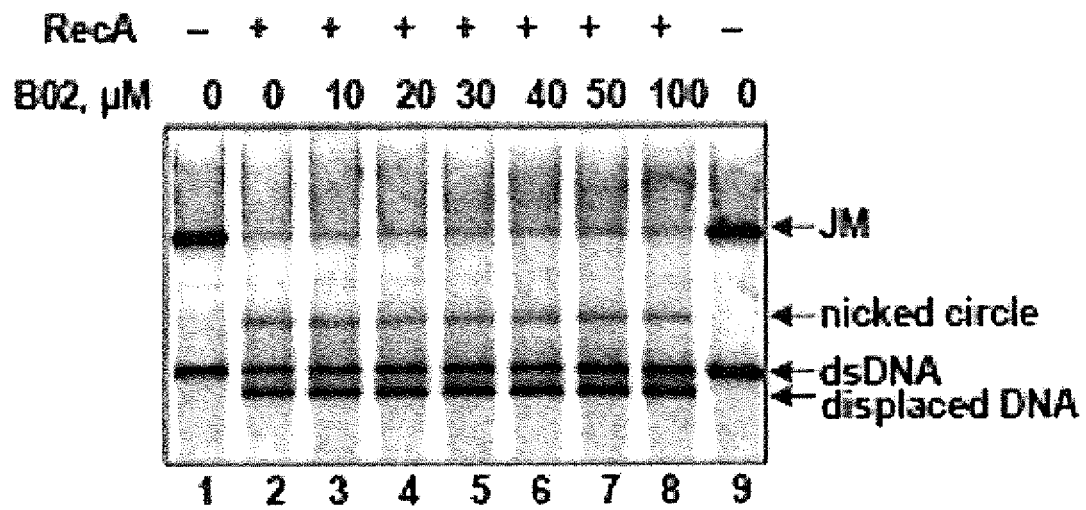
Figure 21:
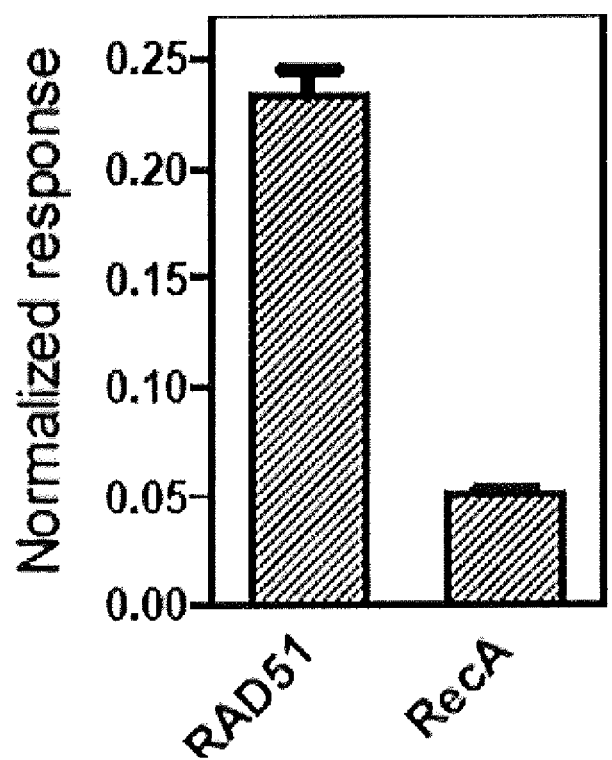
FIG. 21 illustrates the finding that Compound B02 binds directly to RAD51. Compound B02 (50 µM) was injected onto a sensor chip to which RAD51 or RecA had been immobilized. The running buffer S was supplemented with ATP (100 µM). Responses to Compound B02 were normalized to the theoretical maximum response of the surface (Rmax), assuming a 1:1 interaction. Experiments were repeated at least three times; error bars represent S.D.
Figure 22:
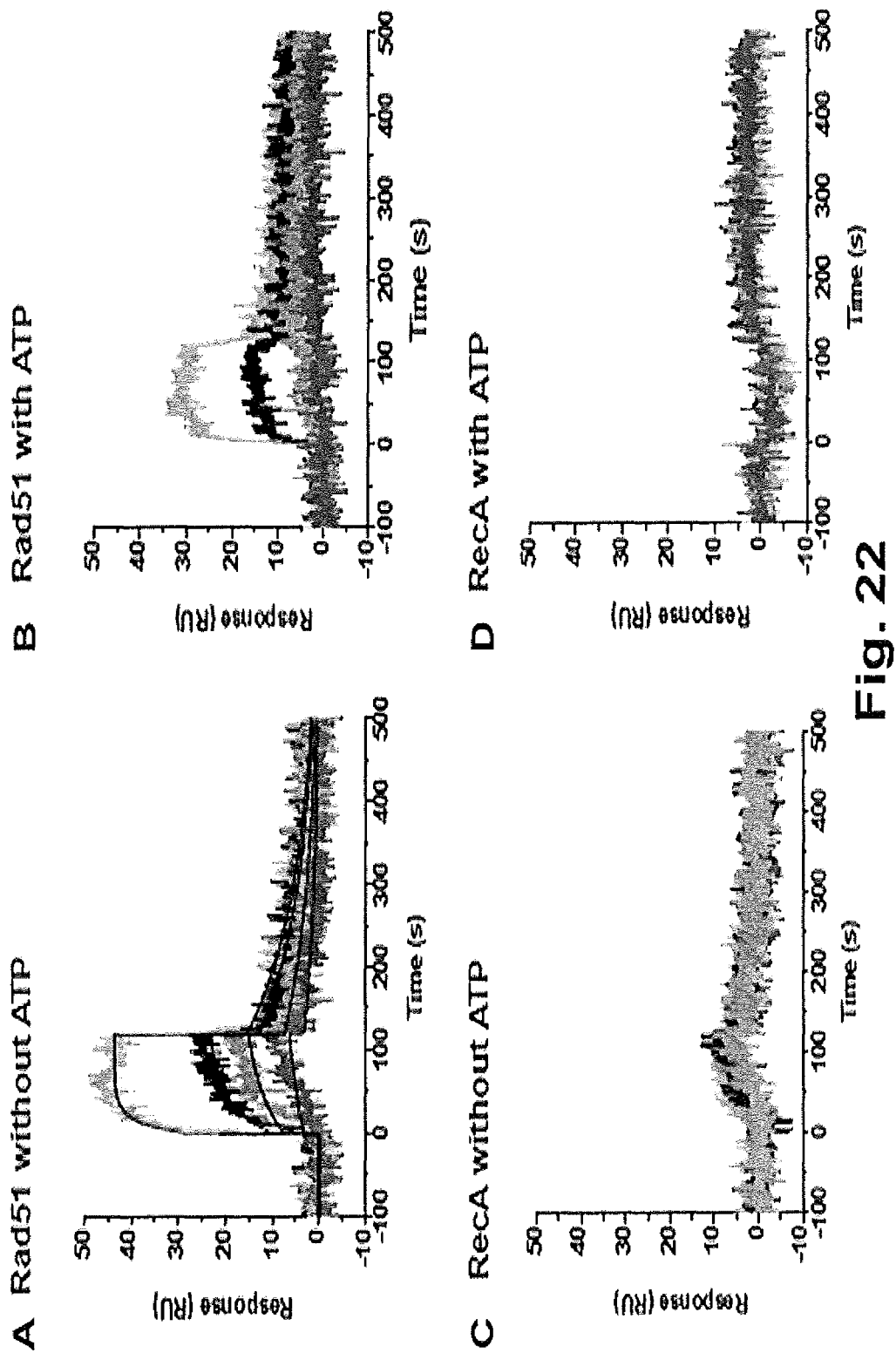
FIG. 22, comprising

RAD51 and its *E. coli* homologous RecA possess DNA strand exchange and DNA branch migration activities. The effect of B02 (FIG. 19A) on these activities of both proteins was examined. pBSK (+) gapped and linear dsDNA substrates that allow separate analysis of DNA strand exchange and branch migration promoted by RAD51/RecA were used (FIG. 19B). At the first step, RAD51/RecA promoted DNA strand exchange between gapped DNA and linear DNA substrates resulting in formation of joint molecules. Joint molecules were then purified and used as substrates for RAD51/RecA branch migration. In accord with previous data showing specific inhibition of RAD51 by B02 in the D-loop assay, B02 (10-100 μM) inhibited DNA strand exchange promoted by RAD51 (FIGS. 19C-19D), but not by RecA (FIGS. 19D & 20A). B02 (10-100 μM) was found to inhibit the DNA branch migration activity of RAD51 (FIGS. 19E-19F). The inhibition was specific, as B02 did not inhibit the branch migration activity of RecA (FIG. 19F & 20B). The IC$_{50}$ value of RAD51 inhibition by B02 was 35 μM for both DNA strand exchange and DNA branch migration. Next, it was tested whether RAD51 inhibition is caused by the direct interaction of B02 with RAD51. Using the surface plasmon resonance (SPR) technique, B02 (6.25-50 μM) was shown to bind to RAD51, but not to RecA (FIGS. 21-22). For B02 binding to RAD51 in the absence of ATP, kinetic values were as follows: k$_a$=4.5 (±0.3)×10$^3$ M$^{-1}$ s$^{-1}$; k$_d$=2.5 (±0.3)=10$^{-2}$ s$^{-4}$; K$_d$=5.6 μM. Using the ethidium bromide displacement assay B02 was shown not to bind DNA. Thus, B02 inhibited DNA strand exchange and branch migration activities through direct and specific binding to RAD51.

Example 13

Disruption of the RAD51 Foci Formation

Figure 23A:
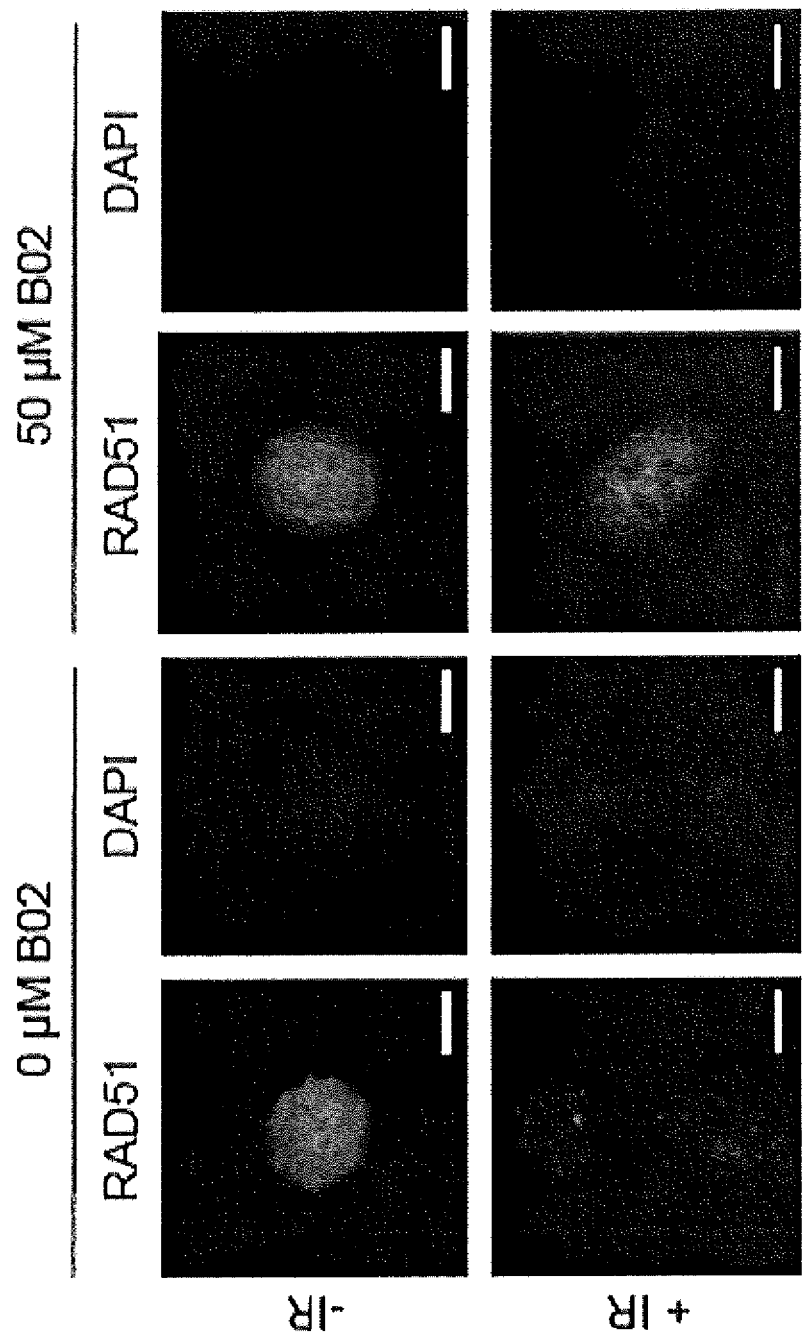
FIGS. 23A-23C, illustrates the finding that B02 disrupts the RAD51 fuel formation.
Figure 23C:
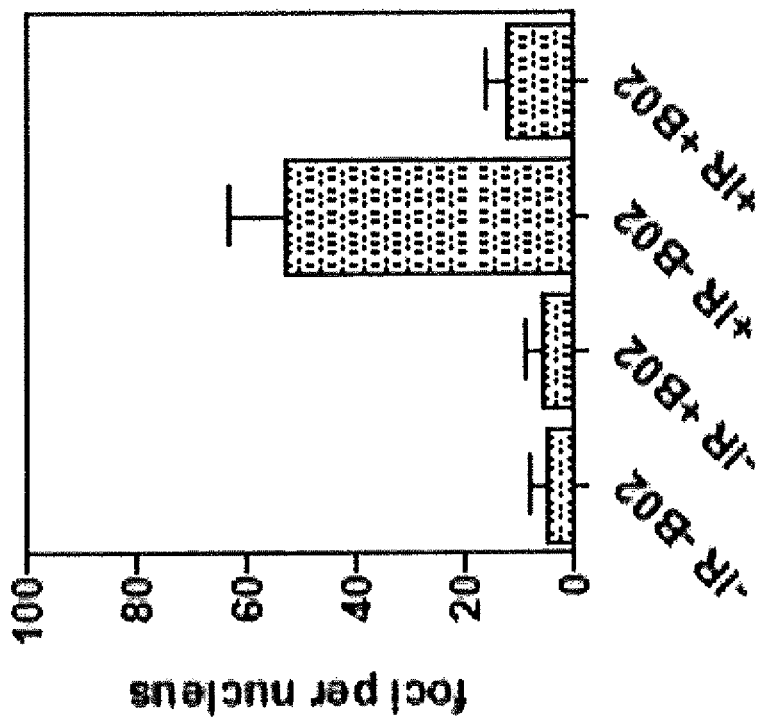
Figure 23B:
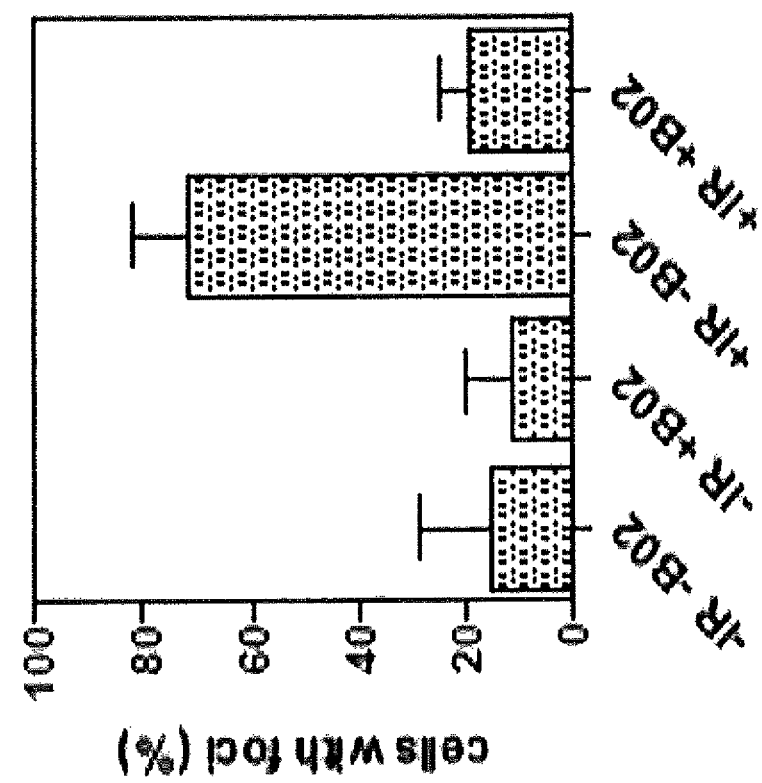

B02 was tested to determine whether it can inhibit RAD51 activities in the cell. In response to DNA damage, RAD51 accumulates in distinct nuclear structures, known as foci. Because RAD51 foci colocalize with ssDNA formed in the cell after DNA damage, it is thought that the foci represent RAD51 complexes with DNA repair intermediates. B02 was found to inhibit RAD51 foci formation induced in 293 human embryonic kidney (HEK) cells by IR. In the presence of B02 (50 μM), the fraction of cells with RAD51 foci (≥1 focus) was decreased in non-irradiated cells (15±13%) (FIGS. 23A-23B); the average number of RAD51 foci per nucleus decreased 4.4-fold, from 53±11 to 12±4 (FIG. 23C). At lower concentrations (20 μM), B02 also inhibited IR-induced RAD51 foci formation, however the inhibitory effect was smaller.

Example 14

Increase in Cell Sensitivity to DNA-Damaging Agents

Figure 24B:
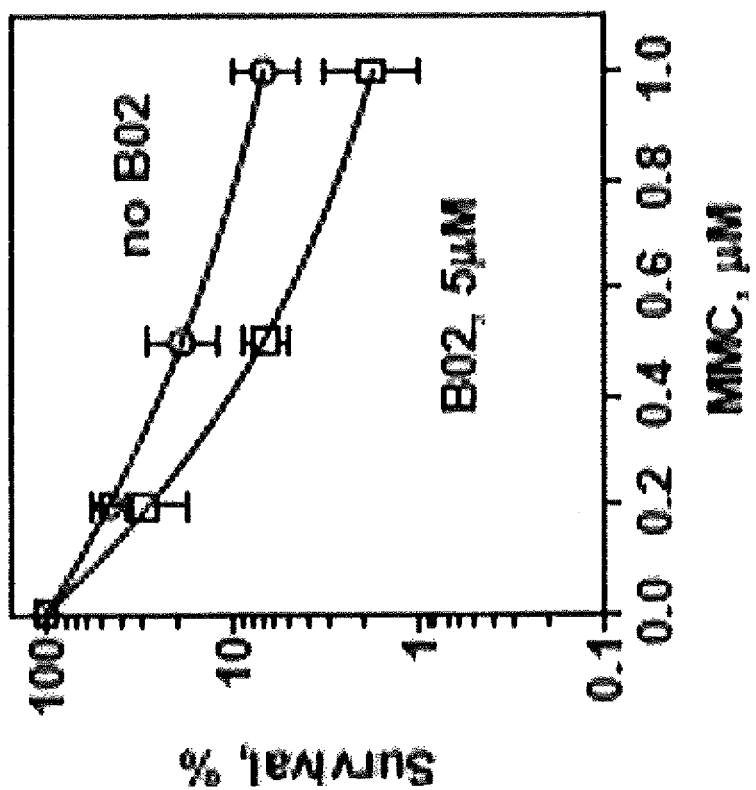
FIGS. 24A-24F, illustrates the finding that B02 increases cell sensitivity to DNA-damaging agents.
Figure 24A:
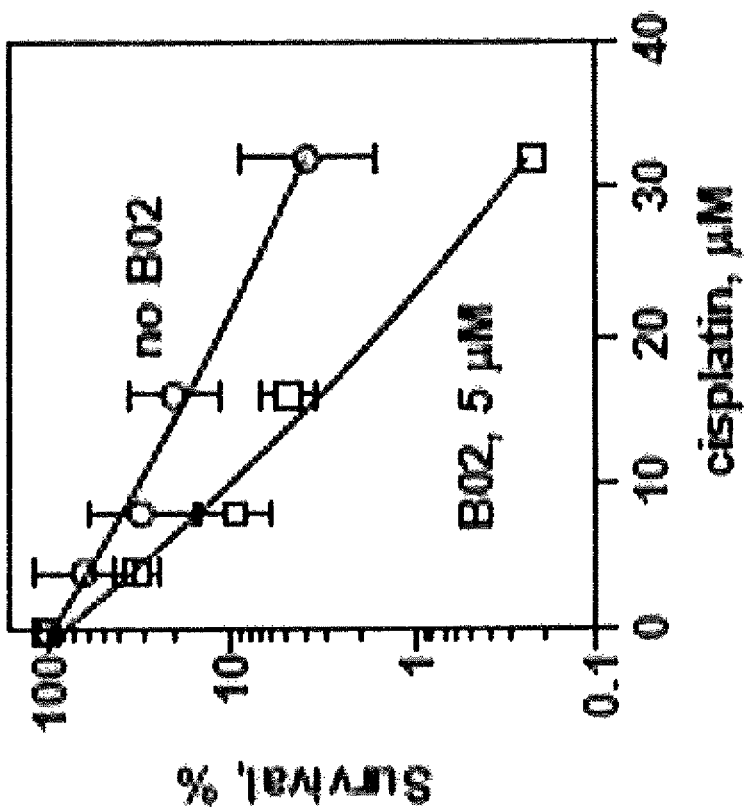
Figure 24D:
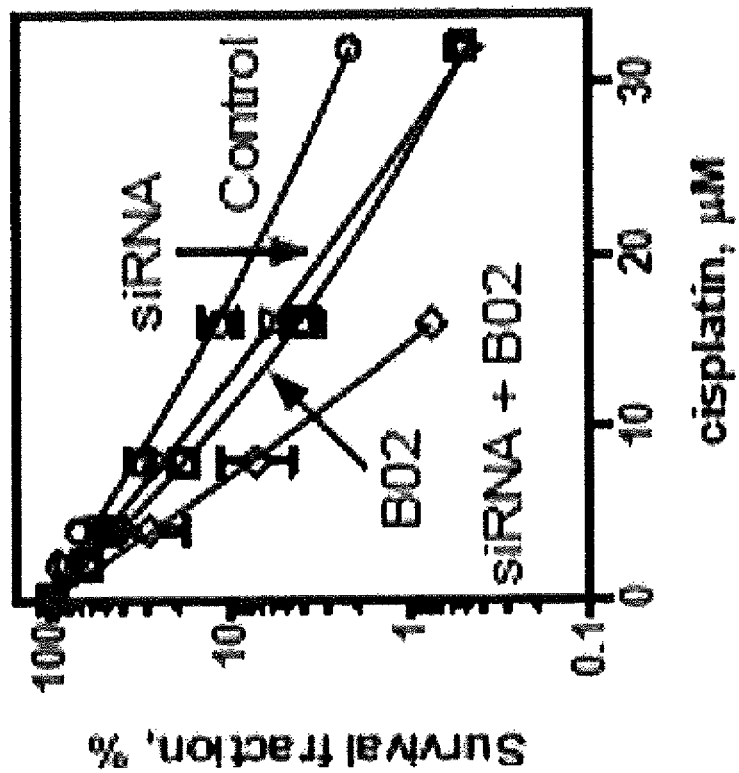
Figure 24C:
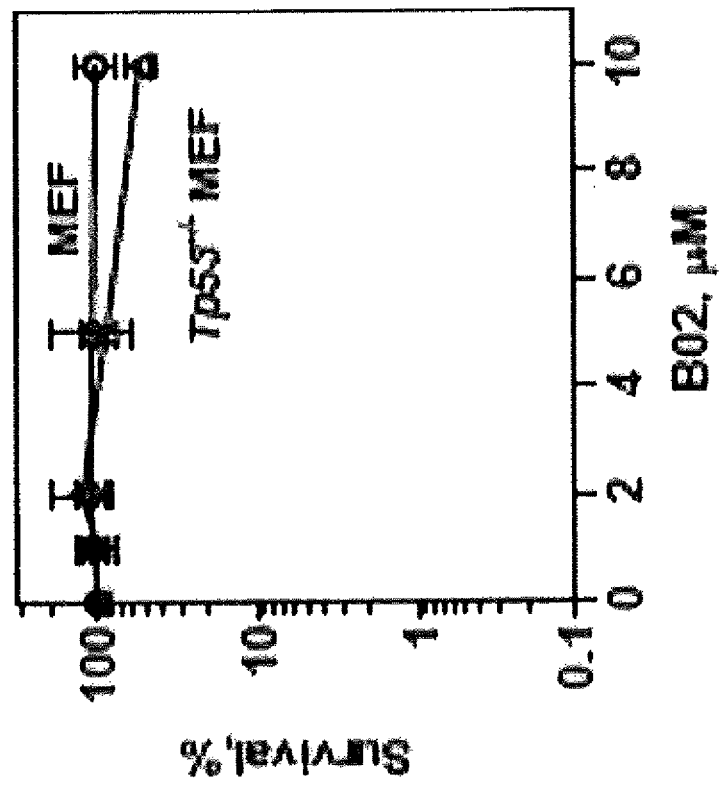
Figure 24F:
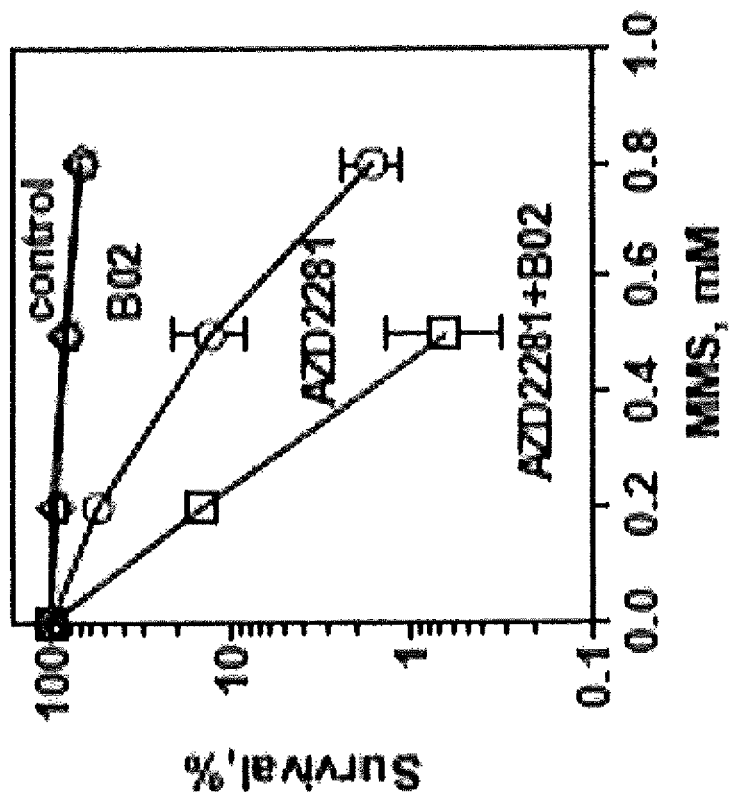
Figure 24E:
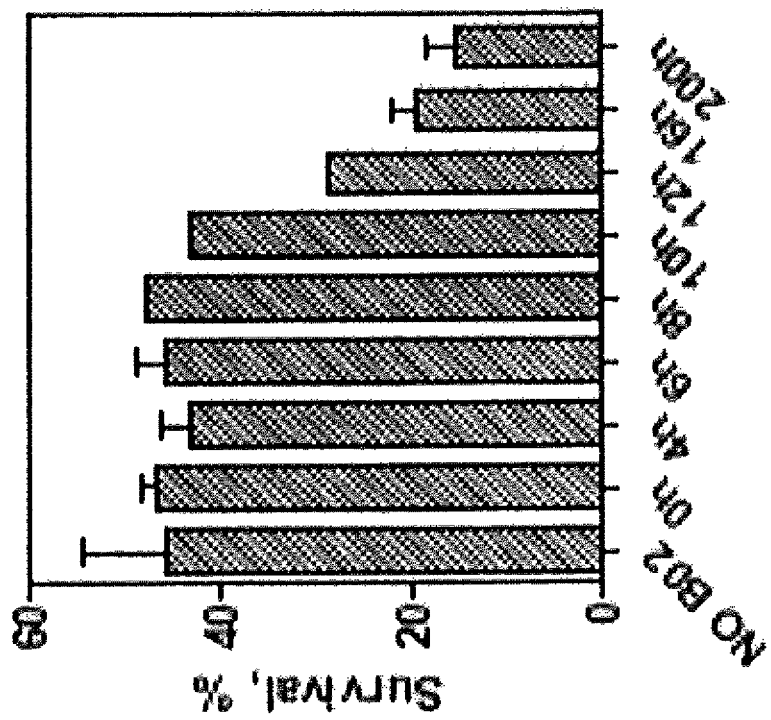
Figure 28B:
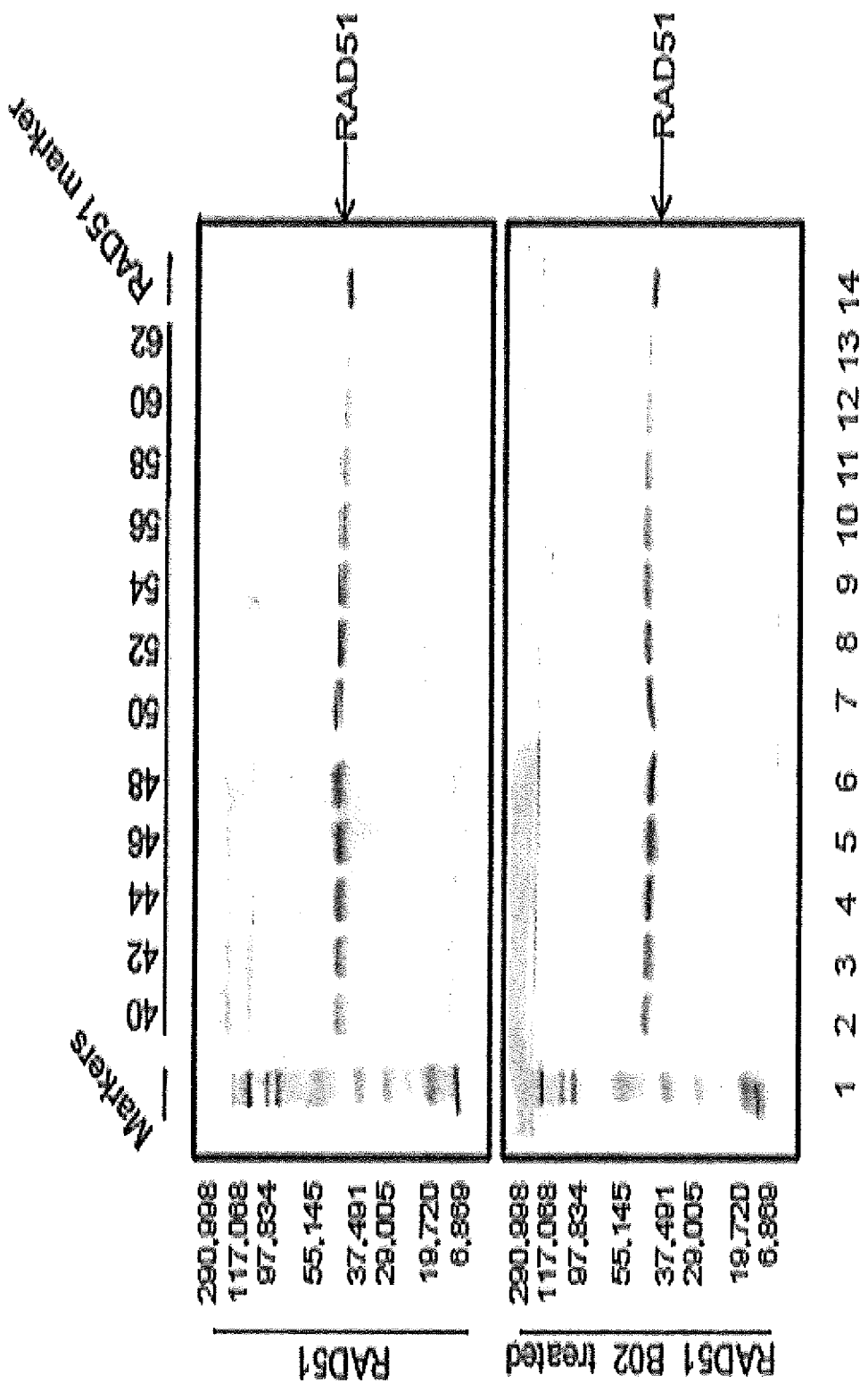

B02 was examined to determine whether it can enhance cell sensitivity to DSB- and ICL-inducing anticancer agents, cisplatin and MMC. Using the clonogenic survival assay it was found that in the presence of B02 (5 μM) mouse embryonic fibroblasts (MEF) became approximately 17- and five-fold more sensitive to cisplatin (32 μM) and MMC (1 μM), respectively (FIGS. 24A-24B). Because, p53 protein is commonly mutated in many human cancers, the effect of B02 on Tp53$^{-/-}$ MEF was also tested. It was found that the sensitivity of Tp53$^{-/-}$ MEF to cisplatin and MMC increased in the presence of B02 similarly to wild type cells (FIG. 25). In these experiments, 5 μM B02 was used, a concentration at which B02 alone did not have a substantial effect on the viability of wild type or Tp53$^{-/-}$ MEF (FIG. 24C). Inhibitory effect of B02 on cell survival observed in co-treatment experiments could be due to depletion of RAD51 that translocated to the sites of DNA damage. This hypothesis was tested using HEK cells in which the RAD51 expression level was decreased by siRNA (FIG. 26). The results showed that indeed the combination of specific RAD51 siRNA and B02 more strongly sensitized HEK cells to cisplatin than did each of these reagents alone (FIG. 24D). The minimum incubation time with B02 that was required for cells' sensitization for cisplatin was determined. These data indicate that 10-12 h of incubation was required to increase the sensitivity of HEK cells for cisplatin (FIG. 24E). After 16 h, the maximal sensitivity was reached. Thus, B02 causes cell sensitization to cisplatin and MMC, indicating the ability of B02 to inhibit RAD51-dependent DSB repair in the cell.

As described herein, the mechanism of RAD51 inhibition by B02 and its ability to inhibit RAD51 homologous recombination and DNA repair in cells was analyzed. B02 was found to bind to RAD51 and inhibit its DNA strand exchange and branch migration activities with high specificity, as it does not affect *E. coli* RecA, a demonstrated that B02 can inhibit RAD51-dependent HR events in the cell and promote cell killing by cytotoxic DSB and ICL-inducing agents.

Because the RAD51-ssDNA filament plays a critical role in HR, its formation is tightly regulated by various factors that either enhance or inhibit RAD51 binding to ssDNA. These data demonstrated that B02 also inhibits RAD51 filament formation. These results showed that B02 impairs RAD51 filament formation by targeting protein-DNA interactions. The filament formation involves binding ssDNA to the RAD51 primary site. Using a coaggregation assay, it was found that B02 also inhibits dsDNA binding to the secondary RAD51 site, which normally occurs during the search for homology.

To address of whether B02 inhibits RAD51-depending HR and DNA repair in the cell, several cell-based assays were carried out. First, it was found that B02 inhibited formation of RAD51 foci in response to IR, which is thought to reflect RAD51 accumulation at the sites of damaged DNA and formation of RAD51-DNA complexes during recombinational DNA repair. Then, using a chromosomally integrated GFP reporter, it was shown that B02 decreased, up to eightfold, the frequency of DSB-induced HR in human cells. It was also demonstrated that B02 increased cell sensitivity to ICL- and DSB-inducing agents, cisplatin and MMC. Finally, it was found that a combination of B02 with PARP1 inhibitor AZD2281 increased cell sensitivity to an alkylating agent (MMS) to a greater extent than does AZD2281 alone. The finding that PARP1 inhibitors enhance the effect of B02 on cell sensitivity to DNA damage is consistent with inhibition of HR by B02. In the co-treatment experiments, B02 showed activity at lower concentrations (5 µM) than in other biological assays, likely due to the depletion of RAD51 that accumulates at the sites of DNA damage. Indeed, it was found that depletion of RAD51 with siRNA had an additive effect with B02 treatment. Moreover, RAD51 is not a canonical enzymes; the DNA strand exchange assay requires rather high RAD51 concentrations (stoichiometric relative to DNA substrates). Concerning RAD51 foci formation, it is worth nothing that each RAD51 focus involves thousands of RAD51 monomers, therefore a decrease in their number in each focus may not have been readily detectable by immunostaining and required higher B02 concentrations (20-50 µM). Overall, these results demonstrated that B02 inhibits RAD51-dependent HR and DSB repair in mammalian cells (FIG. 27).

Because small-molecule inhibitors may be applied in a cell cycle and in a concentration dependent manner, they are especially useful for analysis of proteins essential for cell viability, like RAD51. By applying B02 for different periods of time after DNA damage by cisplain, a maximal time for which DNA repair can be delayed before the cells start dying was determined.

These results indicated that a combination of inhibitors that target alternative DNA repair pathways, e.g., RAD51-dependent and PARP1-dependent DNA repair, can be especially efficient for sensitizing cancer cells for radio- and chemotherapeutic agents. Targeting RAD51 may represent an important strategy to specifically eradicate cancer cells. Consistent with the compensatory role that HR may play in cancer cells, RAD51 was found to be overexpressed in many tumors.

These results demonstrate that B02 inhibitor of RAD51 can efficiently suppress DSB dependent HR in the cell. The inhibitor can be used for the analysis of RAD51 cellular functions and for development of novel anticancer therapies.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A pharmaceutical composition comprising a pharmaceutically acceptable carrier and a compound of Formula (1):

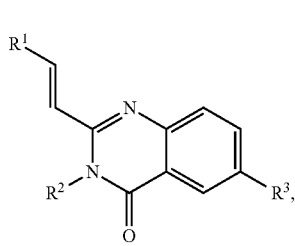
(1)

wherein:
R¹ is pyridinyl;
R² is selected from the group consisting of $C_1$-$C_6$ alkyl, —($C_1$-$C_6$)alkylene-phenyl, and —($C_1$-$C_6$)alkylene-phenyl wherein the phenyl is substituted with a $C_1$-$C_6$ alkyl;
R³ is H or a salt thereof.

2. The pharmaceutical composition of claim 1, wherein R2 is methyl, ethyl, n-propyl, isopropyl, benzyl, benzyl substituted on the phenyl ring with a C1-C6 alkyl.

3. A pharmaceutical composition comprising a compound selected from the group consisting of:

(E)-3-benzyl-2-(2-(pyridine-3-yl)vinyl)quinazolin-4(3H)-one(1a)

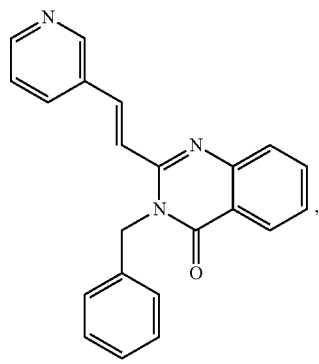
(1a)

(E)-3-ethyl-2-(2-(pyrindin-3-yl)vinyl)quinazolin-4(3H)-one(1b)

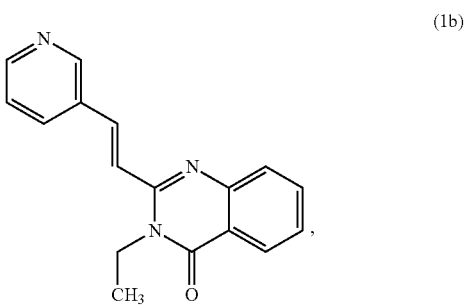 [SMILES: CCn1c(/C=C/c2cccnc2)nc2ccccc2c1=O]
(1b)

and salts thereof and any mixtures thereof.

4. The pharmaceutical composition of claim 1, further comprising a chemotherapeutic agent.

5. The pharmaceutical composition of claim 4, wherein the agent is selected from the group consisting of an alkylating agent, antimetabolite, anthracycline, plant alkaloid, plant terpenoid, topoisomerase inhibitor, antineoplastic agent, and any combinations thereof.

6. The pharmaceutical composition of claim 3, further comprising a chemotherapeutic agent.

7. The pharmaceutical composition of claim 6, wherein the agent is selected from the group consisting of an alkylating agent, antimetabolite, anthracycline, plant alkaloid, plant terpenoid, topoisomerase inhibitor, antineoplastic agent, and any combinations thereof.

* * * * *